(12) United States Patent
Gold et al.

(10) Patent No.: US 6,207,816 B1
(45) Date of Patent: *Mar. 27, 2001

(54) HIGH AFFINITY OLIGONUCLEOTIDE LIGANDS TO GROWTH FACTORS

(75) Inventors: Larry Gold; Neboisa Janjic; Nikos Pagratis, all of Boulder, CO (US)

(73) Assignee: NeXstar Pharmaceuticals, Inc., Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 08/973,124

(22) PCT Filed: May 30, 1996

(86) PCT No.: PCT/US96/08014

§ 371 Date: May 11, 1998

§ 102(e) Date: May 11, 1998

(87) PCT Pub. No.: WO96/38579

PCT Pub. Date: Dec. 5, 1996

Related U.S. Application Data

(63) Continuation-in-part of application No. 08/465,594, filed on Jun. 5, 1995, now Pat. No. 5,846,713, and a continuation-in-part of application No. 08/465,591, filed on Jun. 5, 1995, now Pat. No. 5,837,834, and a continuation-in-part of application No. 08/479,725, filed on Jun. 7, 1995, now Pat. No. 5,674,685, and a continuation-in-part of application No. 08/479,783, filed on Jun. 7, 1995, now Pat. No. 5,668,264, and a continuation-in-part of application No. 08/618,693, filed on Mar. 20, 1996, now Pat. No. 5,723,594, which is a continuation-in-part of application No. 08/458,423, filed on Jun. 2, 1995, now Pat. No. 5,731,144, which is a continuation-in-part of application No. 08/458,424, filed on Jun. 2, 1995, now Pat. No. 5,731,424.

(51) Int. Cl.[7] ............... C07H 21/02; C07H 21/04; C12Q 1/68; C12P 19/34

(52) U.S. Cl. ............... 536/24.1; 536/25.4; 435/6; 435/91.2

(58) Field of Search ............... 435/6, 91.2; 536/24.31, 536/25.4; 935/77, 78

(56) References Cited

U.S. PATENT DOCUMENTS

| | | | |
|---|---|---|---|
| 5,270,163 | 12/1993 | Gold et al. | 435/6 |
| 5,459,015 | 10/1995 | Janjic et al. | 435/6 |
| 5,668,264 * | 9/1997 | Janjic et al. | 536/23.1 |
| 5,674,685 * | 10/1997 | Janjic et al. | 435/6 |
| 5,837,834 * | 11/1998 | Pagratis et al. | 536/23.1 |
| 5,846,713 * | 12/1998 | Pagratis et al. | 435/6 |

FOREIGN PATENT DOCUMENTS

| | | |
|---|---|---|
| 2 183 661 A | 6/1987 | (GB). |
| WO89/06694 | 7/1989 | (WO). |
| WO92/14843 | 9/1992 | (WO). |

OTHER PUBLICATIONS

Robertson and Joyce (1990) Nature 344:467.
Shah et al. (1992) Lancet 339:213.
Thiesen and Bach (1990) Nucleic Acids Research 18:3203.
Artega et al. (1993) J. Clin. Invest. 92:2569.
Arteaga et al. (1990) Cell Growth & Differentiation 1:367.
Barral et al. (1993) Proc. Natl. Acad. Sci USA 90:3442.
Ellington and Szostak (1990) Abstract of papers presented at the 1990 meeting on RNA Processing, Cold Spring Harbor Laboratory, Cold Spring Harbor, NY, p. 84.
Joyce (1989) Gene 82:83.
Joyce and Inoue (1989) Nucleic Acids Research 17:711.
Kinzler and Vogelstein (1989) Nucleic Acids Research 17:3645.
Kramer et al. (1974) J. Mol. Biol. 89:719.
Levisohn and Spiegelman (1968) Proc. Natl. Acad. Sci. USA 60:866.
Levisohn and Spiegelman (1969) Proc. Natl. Acad. Sci. USA 63:805.
Oliphant et al. (1986) Gene 44:177.
Oliphant and Struhl (1987) Methods in Enzymology 155:568.
Oliphand and Struhl (1988) Nucleic Acids Research 16:7673.
Oliphant et al. (1989) Mol. Cell. Biol. 9:2944.
Szostak, "Structure and Activity of Ribozymes," in *Redesigning the Molecules of Life*, (S.A. Benner ed.) Springer–Verlag Berlin Heidelberg, pp. 87–113, (1988).

* cited by examiner

*Primary Examiner*—Stephanie Zitomer
(74) *Attorney, Agent, or Firm*—Swanson & Bratschun LLC

(57) ABSTRACT

Methods are described for the identification and preparation of high-affinity nucleic acid ligands to TGFβ, PDGF and hKGF. Included in the invention are specific RNA and ssDNA ligands to TGFβ1 and PDGF identified by the SELEX method. Also included in the invention are specific RNA ligands to hKGF identified by the SELEX method. Further included are RNA ligands that inhibit the interaction of TGFβ1 and hKGF with their receptors and DNA ligands that inhibit the interaction of PDGF with its receptor.

8 Claims, 19 Drawing Sheets

SEQ ID NO: 171

```
            A C C
           C   A
          G     T
         A       C
        G         A
       G    C      T
      C    A  A   C  A
     C    T    G G    C
     A   C            G-C
     C-G              G-C
     G-G              A-T
                      C-G
                      A-T
                   5'C-G[3'T]
          36t
                              SEQ ID NO: 173
```

```
                        G C
                       C   A
                      A     A
                     G       G
                    C         C
                   T    G      T
                  C    A  A   T
                 G    C    A G
                A    T      T T
               C    G        A
        5'    T    C          
        [3'T]A    G-C
             T    G-C
                  G-C
                  T A
                   A
          41t
                              SEQ ID NO: 174
```

FIGURE 4

```
         T T
        C   T
       T     T
      G       A
     C    T    C
    T    G      T
   G    G  A   G
  T    C    C A
 T    G      T
C    C        
 G-C
 G-C
 G-C
5'TGGGAG-CG[3'T]
    20t
                SEQ ID NO: 172
```

$K_d = 0.065$ nM

SEQ ID NO: 175

$K_d = 0.097$ nM

SEQ ID NO: 176

HIGH AFFINITY OLIGONUCLEOTIDE LIGANDS TO GROWTH FACTORS

RELATEDNESS OF THE APPLICATION

This application is a 35 U.S.C. §371 national phase application of PCT/US96/08014, filed May 30, 1996, a continuation-in-part of U.S. Application Ser. No. 08/465, 594, filed Jun. 5, 1995, now U.S. Pat. No. 5,846,713, a continuation-in-part of 08/465,591, filed Jun. 5, 1995, now U.S. Pat. No. 5,837,834, a continuation-in-part of U.S. Application Ser. No. 08/479,725, filed Jun. 7, 1995, now U.S. Pat. No. 5,674,685, a continuation-in-part of U.S. Application Ser. No. 08/479,783, filed Jun. 7, 1995, now U.S. Pat. No. 5,668,264, and a continuation-in-part of U.S. Application Ser. No. 08/618,693, filed Mar. 20, 1996, now U.S. Pat. No. 5,723,594. which is a CIP of U.S. Application Ser. No. 08/458,423, filed Jun. 2, 1995, now U.S. Pat. No. 5,731,144, and which is a CIP of U.S. Application Ser. No. 08/458,424, filed Jun. 2, 1995, now U.S. Pat. No. 5,731,424.

FIELD OF THE INVENTION

Described herein are methods for identifing and preparing high-affinity nucleic acid ligands to TGFβ, PDGF, and hKGF. The method utilized herein for identifying such nucleic acid ligands is called SELEX, an acronym for Systematic Evolution of Ligands by EXponential enrichment. This invention includes high affinity nucleic acid ligands of TGFB, PDGF, and hKGF. Further disclosed are RNA and DNA ligands to TGFβ1 and PDGF and RNA ligands to hKGF. Also included are oligonucleotides containing nucleotide derivatives chemically modified at the 2'-positions of pyrimidines. Additionally disclosed are RNA ligands to TGFβ1 and hKGF containing 2'-$NH_2$-modifications or 2'-F-modifications and RNA ligands to PDGF containing 2'-F modifications. This invention also includes high affinity nucleic acid inhibitors of TGFβ1, PDGF, and hKGF. The oligonucleotides of the present invention are useful as pharmaceuticals or diagnostic agents.

BACKGROUND OF THE INVENTION

TGFβ

The transforming growth factor –β (TGFβ) polypeptides influence growth, differentiation, and gene expression in many cell types. The first polypeptide of this family that was characterized, TGFβ1 has two identical 112 amino acid subunits which are covalently linked. TGFβ1 is a highly conserved protein with only a single amino acid difference distinguishing human from mice forms. There are two other members of the TGFβ gene family that are expressed in mammals. TGFβ2 is 71% homologous to TGFβ1(de Martin et al., (1987) *EMBO J.* 6:3673–3677), whereas TGFβ3 is 80% homologous to TGFβ1 (Derynck et al., (1988) *EMBO J* 7:3737–3743). The structural characteristics of TGFβ1 as determined by nuclear magnetic resonance (Archer et al., (1993) *Biochemistry* 32:1164–1171) agree with the crystal structure of TGFβ2 (Daopin et al., (1992) *Science* 257:369–374; Schluneggr and Grutter (1992) *Nature* 38:430–434).

Even though the TGFβ's have similar three dimensional structures, they are by no means physiologically equivalent. There are at least three different extracellular receptors, type I, II and III, involved in transmembrane signaling of TGFβ to cells carrying the receptors. For reviews, see Derynck (1994) *TIBS* 19:548–553 and Massague (1990) *Annu. Rev. Cell Biol* 6:597–641. In order for TGFβ2 to effectively interact with the type II TGFβ receptor, the type III receptor must also be present (Derynck (1994) *TIBS* 19:548–553). Vascular endothelial cells lack the type III receptor. Instead endothelial cells express a structurally related protein called endoglin (Cheifetz et al., (1992) *J. Biol. Chem.* 267:19027–19030), which only binds TGFβ1 and TGFβ3 with high alnnity. Thus, the relative potency of the TGFβ's reflect the type of receptors expressed in a cell and organ system.

In addition to the regulation of the components in the multifactorial signaling pathway, the distribution of the synthesis of TGFβ polypeptides also affects physiological function. The distribution of TGFβ2 and TGFβ3 is more limited (Derynck et al., (1988) *EMBO J* 7:3737–3743) than TGFβ1, e.g., TGFβ3 is limited to tissues of mesenchymal origin, whereas TGFβ1 is present in both mesenchymal and epithelial cells.

TGFβ1 is a multifunctional cytokine critical for tissue repair. High concentrations of TGFβ1 are delivered to the site of injury by platelet granules (Assoian and Sporn, (1986) J Cell Biol. 102:1217–1223.). TGFβ1 initiates a series of events that promote healing including chemotaxis of cells such as leukocytes, monocytes and fibroblasts, and regulation of growth factors and cytokines involved in angiogenesis, cell division associated with tissue repair and inflammatory responses. TGFβ1 also stimulates the synthesis of extracellular matrix components (Roberts et aL, (1986) *Proc. Natl. Acad Sci USA* 83:4167–4171; Sporn et al., (1983) *Science* 219:1329–1330; Massague, (1987) *Cell* 49:437–438) and most importantly for understanding the pathophysiology of TGFβ1, TGFβ1 autoregulates its own synthesis (Kim et al., (1989) *J Biol Chem* 264:7041–7045).

A number of diseases have been associated with TGFβ1 overproduction. Fibrotic diseases associated with TGFβ1 overproduction can be divided into chronic conditions such as fibrosis of kidney, lung and liver and more acute conditions such as dermal scarring and restenosis. Synthesis and secretion of TGFβ1 by tumor cells can also lead to immune suppression such as seen in patients with aggressive brain or breast tumors (Arteaga et al., (1993) *J Clin Invest* 92: 2569–2576). The course of Leishmanial infection in mice is drastically altered by TGFβ1 (Barral-Netto et al., (1992) *Science* 257:545–547). TGFβ1 exacerbated the disease, whereas TGFβ1 antibodies halted the progression of the disease in genetically susceptible mice. Genetically resistant mice became susceptible to Leishmanial infection upon administration of TGFβ1.

The profound effects of TGFβ1 on extracellular matrix deposition have been reviewed (Rocco and Ziyadeh, (1991) in Contemporary Issues in Nephrology v23, Hormones, autocoids and the kidney. ed. Jay Stein, Churchill Livingston, New York pp391–410; Roberts et al., (1988) *Rec. Prog. Hormone Res.* 44:157–197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGFβ1 has profound effects on the kidney. The accumulation of mesangial matrix in proliferative glomerulonephritus (Border et al., (1990) *Kidney Int.* 37:689–695) and diabetic nephropathy (Mauer et al., (1984) *J. Clin Invest.*74:1143–1155) are clear and dominant pathological features of the diseases. TGFβ1 levels are elevated in human diabetic glomerulosclerosis (advanced neuropathy) (Yamamoto et al., (1993) *Proc. Natl. Acad. Sci.* 90:1814–1818). TGFβ1 is an important mediator in the genesis of renal fibrosis in a number of animal models (Phan et al., (1990) *Kidney Int.* 37:426; Okuda et al., (1990) *J. Clin Invest.* 86:453). Suppression of experimentally induced glomerulonephritus in rats has been demonstrated by antiserum against TGFβ1 (Border et al., (1 990) *Nature* 346:371) and by an extracellular matrix protein, decorin, which can bind TGFβ1 (Border et al., (1992) *Nature* 360:361–363).

Too much TGFβ1 leads to dermal scar-tissue formation. Neutralizing TGFβ1 antibodies injected into the margins of healing wounds in rats have been shown to inhibit scarring without interfering with the rate of wound healing or the tensile strength of the wound (Shah et al, (1992) *Lancet* 339:213–214). At the same time there was reduced angiogenesis, reduced number of macrophages and monocytes in the wound, and a reduced amount of disorganized collagen fiber deposition in the scar tissue.

TGFβ1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGFβ1 gene, TGFβ1 gene expression was associated with both extracellular matrix synthesis and hyperplasia (Nabel et al., (1993) *Proc. Natl. Acad. Sci USA* 90–10759–10763). The TGFβ1 induced hyperplasia was not as extensive as that induced with PDGF-BB, but the extracellular matrix was more extensive with TGFβ1 transfectants. No extracellular matrix deposition was associated with FGF-1 (a secreted form of FGF) induced hyperplasia in this gene transfer pig model (Nabel (1993) *Nature* 362:844–846).

There are several types of cancer where TGFβ1 produced by the tumor may be deleterious. MATLyLu rat cancer cells (Steiner and Barrack, (1992) Mol. Endocrinol. 6:15–25) and MCF-7 human breast cancer cells (Arteaga et al., (1993) *Cell Growth and Differ.* 4:193–201) became more tumorigenic and metastatic after transfection with a vector expressing the mouse TGFβ1. In breast cancer, poor prognosis is associated with elevated TGFβ (Dickson et al., (1987) *Proc. Natl. Acad Sci. USA* 84:837–841; Kasidetal., (1987) *Cancer Res.* 47:5733–5738; Daly et al., (1990) *J Cell Biochem* 43:199–21 1; Barrett-Lee et aL, (1990) *Br. J Cancer* 61:612–617; King et al., (1989) *J Steroid Biochem* 34:133–138; Welch et al., (1990) *Proc. Natl. Acad Sci.* 87:7678–7682; Walker et aL., (1992) *Eur J Cancer* 238: 641–644) and induction of TGFβ1 by tamoxifen treatment (Butta et al., (1992) *Cancer* Res 52:4261–4264) has been associated with failure of tamoxifen treatment for breast cancer (Thompson et al., (1991) *Br. J Cancer* 63:609–614). Anti TGFβ1antibodies inhibit the growth of MDA-231 human breast cancer cells in athymic mice (Arteaga et al., (1993) *J Clin Invest* 92: 2569–2576), a treatment which is correlated with an increase in spleen natural killer cell activity. CHO cells transfected with latent TGFβ1 also showed decreased NK activity and increased tumor growth in nude mice (Wallick et al., (1990) *J Exp Med* 172:1777–1784). Thus, TGFβ1 secreted by breast tumors may cause an endocrine immune suppression.

High plasma concentrations of TGFβ1 have been shown to indicate poor prognosis for advanced breast cancer patients (Anscher et al. (1993) *N Engl J Med* 328:1592–8). Patients with high circulating TGFβ before high dose chemotherapy and autologous bone marrow transplantation are at high risk for hepatic veno-occlusive disease (15–50% of all patients with a mortality rate up to 50%) and idiopathic interstitial pneumonitis (40–60% of all patients). The implication of these findings is 1) that elevated plasma levels of TGFβ1can be used to identify at risk patients and 2) that reduction of TGFβ1 could decrease the morbidity and mortality of these common treatments for breast cancer patients.

PDGF

Platelet-derived growth factor (PDGF) was originally isolated from platelet lysates and identified as the major growth-promoting activity present in serum but not in plasma. Two homologous PDGF isoforms have been identified, PDGF A and B, which are encoded by separate genes (on chromosomes 7 and 22). The most abundant species from platelets is the AB heterodimer, although all three possible dimers (AA, AB and BB) occur naturally. Following translation, PDGF dimers are processed into ≈30 kDa secreted proteins. Two cell surface proteins that bind PDGF with high affinity have been identified, α and β (Heldin et al., *Proc. Natl. Acad. Sci.*, 78: 3664 (1981); Williams et al., *Proc. Natl. Acad. Sci.*, 79: 5867 (1981)). Both species contain five immunoglobulin-like extracellular domains, a single transmembrane domain and an intracellular tyrosine kinase domain separated by a kinase insert domain. The functional high affinity receptor is a dimer and engagement of the extracellular domain of the receptor by PDGF results in cross-phosphorylation (one receptor tyrosine kinase phosphorylates the other in the dimer) of several tyrosine residues. Receptor phosphorylation leads to a cascade of events that results in the transduction of the mitogenic or chemotactic signal to the nucleus. For example, in the intracellular domain of the PDGF β receptor, nine tyrosine residues have been identified that when phosphorylated interact with different src-homology 2 (SH2) domain-containing proteins including phospholipase C-g, phosphatidylinositol 3'-kinase, GTPase-activating protein and several adapter molecules like Shc, Grb2 and Nck (Heldin, *Cell,* 80: 213 (1995)). In the last several years, the specificities of the three PDGF isoforms for the three receptor dimers (αα, αβ, and ββ) has been elucidated. The a-receptor homodimer binds all three PDGF isoforms with high affinity, the β-receptor homodimer binds only PDGF BB with high affinity and PDGF AB with approximately 10-fold lower affmity, and the αβ-receptor heterodimer binds PDGF BB and PDGF AB with high affinity (Westermark & Heldin, *Acta Oncologica*, 32: 101 (1993)). The specificity pattern results from the ability of the A-chain to bind only to the a-receptor and of the B-chain to bind to both α and β-receptor subunits with high affinity.

The earliest indication that PDGF expression is linked to malignant transformation came with the finding that the amino acid sequence of the PDGF-B chain is virtually identical to that of p28$^{sis}$, the transforming protein of the simian sarcoma virus (SSV) (Waterfield et al. *Nature,* 304: 35 (1983); Johnsson et al., *EMBO J.,* 3: 921 (1984)). The transforming potential of the PDGF-B chain gene and, to a lesser extent, the PDGF-A gene was demonstrated soon thereafter (Clarke et al., *Nature,* 308: 464 (1984); Gazit et al., *Cell,* 39: 89 (1984); Beckmann et al., *Science,* 241: 1346; Bywater et al., *Mol. Cell. Biol.,* 8: 2753 (1988)). Many tumor cell lines have since been shown to produce and secrete PDGF, some of which also express PDGF receptors (Raines et al., *Peptide Growth Factors and Their Receptors*, Springer-Verlag, Part I, p 173 (1990)). Paracrine and, in some cell lines, autocrine growth stimulation by PDGF is therefore possible. For example, analysis of biopsies from human gliomas has revealed the existence of two autocrine loops: PDGF-B/β-receptor in tumor-associated endothelial cells and PDGF-A/α-receptor in tumor cells (Hermansson et al., *Proc. Natl. Acad. Sci.,* 85: 7748 (1988); Hermansson et al., *Cancer Res.,* 52: 3213 (1992)). The progression to high grade glioma was accompanied by the increase in expression of PDGF-B and the β-receptor in tumor-associated endothelial cells and PDGF-A in glioma cells. Increased expression of PDGF and/or PDGF receptors has also been observed in other malignancies including fibrosarcoma (Smits et al., *Am. J. Pathol.,* 140: 639 (1992)) and thyroid carcinoma (Heldin et al., *Endocrinology,* 129: 2187 (1991)).

In view of its importance in proliferative disease states, antagonists of PDGF may find usefilm clinical applications. Currently, antibodies to PDGF (Johnsson et al., (1985) *Proc. Natl. Acad. Sci., U. S. A.* 82: 1721–1725; Ferns et al., (1991) *Science* 253: 1129–1132; Herrenet al., (1993) *Biochimica et Biophysica Acta* 1173, 194–302) and the soluble PDGF receptors (Herrenet al., (1993) *Biochimica et Biophysica Acta* 1173: 294–302; Duanet al., (1991) *J. Biol. Chem.* 266: 413–418; Tiesman et al., (1993) *J. Biol. Chem.* 268: 9621–9628) are the most potent and specific antagonists of PDGF. Neutralizing antibodies to PDGF have been shown to revert the SSV-transformed phenotype (Johnsson et al., (1985) *Proc. Natl. Acad. Sci. U.S.A.* 82: 1721–1725) and to inhibit the development of neointimal lesions following arterial injury (Ferns et al., (1991) *Science* 253: 1129–1132). Other inhibitors of PDGF such as suramin (Williams et al., (1984) *J. Biol. Chem.* 259: 5287–5294; Betsholtz et al., (1984) *Cell* 39 447–457), neomycin (Vassbotn et al., (1992) *J. Biol. Chem.* 267 15635–15641) and peptides derived from the PDGF amino acid sequence (Engstrom et al., 1992) *J. Biol. Chem.* 267: 16581–16587) have been reported, however, they are either too toxic or lack sufficient specificity or potency to be good drug candidates. Other types of antagonists of possible clinical utility are molecules that selectively inhibit the PDGF receptor tyrosine kinase (Buchdunger et al., (1995) *Proc. Natl. Acad. Sci., U.S.A.* 92: 2558–2562; Kovalenko et al, (1994) *Cancer Res.* 54: 6106–6114).

hKGF a) Biochemical Properties of hKGF

Human Keratinocyte Growth Factor (hKGF) is a small (26–28KD) basic heparin-binding growth factor and a member of the FGF family. hKGF is a relatively newly identified molecule, which is also known as FGF-7 (Finch et al., (1989) *Science* 245:752–755). It is a growth factor specific for epithelial cells (Rubin et al., (1989) *Proc Natl Acad Sci USA* 86:802–806), and its main function is in development/morphogenesis (Werner et al., (1994) *Science* 266:819–822) and in wound healing (Werner et al., (1992) *Proc Natl Acad Sci USA* 89:6896–6900). The major in vivo source of hKGF is stromal fibroblasts (Finch et al., (1989) *Science* 245:752–755). Microvascular endothelial cells (Smola et al., (1993) *J Cell Biol* 122:417–429) and very recently, activated intraepithelial gd T cells (Boismenu et al., (1994) *Science* 266:1253–1255) have also been shown to synthesize hKGF. hKGF expression is stimulated in wounds (Werner et al., (1992) *Proc Natl Acad Sci USA* 89:6896–6900). Several cytokines are shown to be hKGF inducers (Brauchle et al., (1994) *Oncogene* 9:3199–3204), with IL-1 the most potent one (Brauchle et al., (1994) *Oncogene* 9:3199–3204; Chedid et al., (1994) *J Biol Chem* 269:10753–10757). Unlike bFGF, hKGF has a signal peptide and thus is secreted by producing cells (Finch et al., (1989) *Science* 245:752–755). hKGF can be overexpressed in *E. coli* and the recombinant protein (~19–21 KD) is biologically active (Ron et al., (1993) *J Biol Chem* 268:2984–2988). The *E. coli* derived recombinant protein is 10 times more mitogenic than the native protein (Ron et al., (1993) *J Biol Chem* 268:2984–2988). This difference may be due to glycosylation. The native protein has a potential Asn glycosylation site (Ron et al., (1993) *J Biol Chem* 268:2984–2988).

The hKGF bioactivity is mediated through a specific cell surface receptor (Miki et al., (1991) *Science* 251:72–75). The hKGF receptor is a modified FGF receptor resulting from alternative splicing of the C-terminal extracellular region of the FGF-R2 (Miki et al., (1992) *Proc Natl Acad Sci USA* 89:246–250). NIH/3T3 cells transfected with the hKGF receptor express high affinity (-200 pM) binding sites for hKGF (Miki et al., (1992) *Proc Natl Acad Sci USA* 89:246–250). The approximate number of specific binding sites per NIH/3T3 cell is about 500,000 (D. Bottaro and S. Aaronson, personal communication). The hKGF receptor binds hKGF and aFGF with similar affinities, and bFGF with about 20 fold less affinity (Miki et al., (1991) *Science* 251:72–75; Miki et al., (1992) *Proc Natl Acad Sci USA* 89:246–250). A variant ofthe hKGF receptor has been found to be an amplified gene (i.e., one gene, multiple copies), designated K-SAM, in a human stomach carcinoma cell line (Hattori et al., (1990) *Proc Natl Acad Sci USA* 87: 5983–5987).

Heparin has been reported to be an inhibitor of hKGF bioactivity (Ron et al., (1993) *J Biol Chem* 268:2984–2988). This is in contrast to the agonistic effect of heparin for aFGF (Spivak-Kroixman et al., (1994) *Cell* 79:1015–1024).

b) Role of hKGF in Human Disease

The recombinant hKGF molecule has been available only since 1993. Therefore, there is limited information on the role of hKGF in human disease. The published literature, however, contains evidence that strongly suggests a role for hKGF in at least two human diseases, namely psoriasis and cancer. hKGF has also been implicated in inflammatory bowel disease (P. Finch, personal communication).

Psoriasis

Psoriasis is a skin disorder which can be debilitating (Greaves et al., (1995) *N Eng J Medicine* 332: 581–588), characterized by hyperproliferation of the epidermis and incomplete differentiation of keratinocytes, together with dermal inflammation (Abel et al., (1994) *Scientific American Medicine* III-1 to III-18; Greaves et al., (1995) *N Eng J Medicine* 2:581–588). There is not yet an effective treatment for psoriasis (Anonymous, (1993) Drug & Market Development 4:89–101; Abel et al., (1994) *Scientific American Medicine* III-1 to III-18; Greaves et al., (1995) *N Eng J Medicine* 2:581–588). Psoriasis occurs in 0.5 to 2.8 percent of the population with the highest incidence in Scandinavia. In the US in 1992, it was estimated that 4–8 million people affected with psoriasis spent about $600 million for various drugs and related therapies, none of which is very effective. Most of the expenditure was made by about 400,000 patients with severe psoriasis spending $1,000–1,500 annually on treatment. There are about 200,000 new cases of psoriasis every year.

The basic cause of the disorder is not known, but it results from a primary or secondary defect in the mechanisms that regulate epidermal keratinocyte cell division (Abel et al., (1994) *Scientific American Medicine* III-1 to III-18). Psoriasis responds to steroids and cyclosporine and in that sense is characterized as an immune disease (Abel et al., (1994) *Scientific American Medicine III*-1 to III-18). Since hKGF is the primary specific growth factor for keratinocytes, its overexpression and deregulation are primary candidates as the cause of for, keratinocyte hyperproliferation in psoriasis. The demonstration that the immune system is a prime regulator of hKGF release (Boismenu et al., (1994) *Science* 266: 1253–1255; Brauchle et al., (1994) *Oncogene* 9: 3199–3204; Chedid et al., (1994) *J Biol Chem* 269: 10753–10757) strengthens the notion that hKGF deregulation is the cause of psoriasis. Furthermore, application of hKGF in porcine wounds creates a histological appearance resembling psoriasis (Staiano-Coico et al., (1993) *J Ex Med* 178:865–878); keratinocyte derived hKGF in transgenic mice causes pathology reminiscent to psoriasis (Guo et al., (1993) *EMBO J* 12: 973–986); in situ hybridization experiments demonstrated a moderate and a strong upregulation of hKGF and hKGF receptors respectively in psoriasis (P. Finch, personal communication). In situ hybridization experiments also demonstrated involvement of hKGF in another immune disease namely, inflammatory bowel disease (P. Finch, personal communication).

Cancer

It is well established in the literature that deregulation of the expression of growth factors and growth factor hKGF and/or its receptor is expected to be the transformation event in some human cancers. The transforming ability of the hKGF system has been demonstrated in vitro (Miki et al., (1991) *Science* 251:72–75). In another study, carcinoma cell-lines have been found to express the hKGF receptor and to respond to hKGF but not to aFGF, while sarcoma cell-lines do not express hKGF receptors and respond to aFGF but not to hKGF (Ishii et al., (1994) *Cancer Res* 54:518–522).

Gastrointestinal Cancer

Several poorly differentiated stomach cancers have an amplified gene, designated K-sam, which is an isoform of the hKGF-receptor (Katoh et al., (1992) *Proc Natl Acad Sci USA* 89:2960–2964). In vivo administration of hKGF to rats causes proliferation of pancreatic ductal epithelial cell (Yi et al., (1994) *Am J Pathol* 145:80–85), hepatocytes, and epithelial cells throughout the gastrointestinal tract (Housley et al., (1994) *J Clin Invest* 94:1764–1777).

Lung Cancer

Administration of hKGF to rats causes type II pneumocyte hyperplasia similar to the bronchoalveolar cell variant of lung carcinoma (Ulich et al., (1994) *J Clin Invest* 93:1298–1306).

Breast Cancer

In vivo, hKGF causes mammary duct dilation and rampant epithelial hyperplasia, both of which are common features of breast cancers (Ulich et al., (1994) *Am J Pathol* 144:862–868; Yi et al., (1994) *Am J Pathol* 145:1015–1022). However, the ductal epithelium of breastfeeding rats is resistant to the growth promoting effects of hKGF and this is of interest in regard to epidemiological observations that pregnancy in women decreases susceptibility to breast cancer and that dairy cows almost never develop breast cancer (Kuzma, 1977, *Breast in Pathology*, Mosby Co.). There is additional supporting evidence implicating hKGF in breast cancer. hKGF mRNA has been detected recently in normal human breast tissue and in 12 of 15 breast tumor samples tested (Koos et al., (1993) *J Steroid Biochem Molec Biol* 45:217–225). The presence of hKGF mRNA in breast tumors considered in conjunction with the observation that hKGF is present in nonneoplastic mammary glands and that hKGF causes rampant proliferation of mammary epithelium suggests that hKGF may be an autocrine or paracrine growth factor important in the regulation of the growth of normal and neoplastic mammary epithelium (Ulich et al., (1994) *Am J Pathol* 144:862–868). Infiltrating ductal mammary adenocarcinoma is characteristically enveloped by a desmoplasmic stroma that has been postulated to represent a defensive host response to the carcinoma (Ulich et al., (1994) *Am J Pathol* 144:862–868). Since hKGF is stroma derived it is possible that the desmoplasmic stroma contributes rather than inhibits the growth of the tumor.

Prostate Cancer

The growth promoting effect of androgens on prostate tumors appears to be mediated through hKGF (Yan et al., (1992) *Mol Endo* 6:2123–2128), as androgens induce the expression of hKGF in prostate stroma cells. Prostate tumors that are androgen dependent in vivo, are androgen independent in vitro, but hKGF dependent (Yan et al., (1992) *Mol Endo* 6:2123–2128). In agreement with the role of hKGF as andromedin is the observation that hKGF functions in epithelial induction during seminal vesicle development, a process that is directed by androgen (Alarid et al., (1994) *Proc Natl Acad Sci USA* 91:1074–1078). Furthermore, hKGF causes aberrant activation of the androgen receptor, thus probably contributing to the failure of androgen ablation therapy in prostate cancer (Culig et al., (1994) *Cancer Res* 54:5474–5478). Based on this information, it is possible that genetic alterations cause hKGF to escape androgen regulation and thus convert the androgen dependent tumor into an androgen independent, highly malignant tumor. Such tumors would still be able to express the androgen regulated marker PSA, as hKGF also causes the aberrant activation of the androgen receptor. It is also likely that hKGF might be responsible for Benign Prostate Hypertrophy (BPH), a common health problem in older men (D. Bottaro, personal communication).

d) hKGF Competitors

To date, a monoclonal antibody and a short hKGF-receptor derived peptide (25-mer) have been described as hKGF competitors (Bottaro et al., (1993) *J Biol Chem* 268:9180–9183). The monoclonal antibody, designated 1G4, has a Kd of 200 pM for hKGF. The short peptide inhibits hKGF binding to the cell surface of NIH/3T3 cells expressing the human receptor with a Ki of about 1–5 $\mu$M. Bottaro et al. (WO 94/25057) provide hKGF-receptor peptides which inhibit binding between hKGF and its receptor. Also provided is a method of assaying test compounds for the ability to inhibit hKGF receptor-mediated cell proliferation.

e) Assaying for Receptor-Growth Factor Interaction

Blocking the interaction of growth factors and lymphokines with their cell surface receptor using antagonists has been an approach for disease treatment. The discovery of such antagonists requires the availability of biochemical assays for the receptor-growth factor or lymphokine interaction. A classic assay has been the competitive inhibition of radiolabeled growth factor or lymphokine (tracer) to its cell surface receptor. These types of assays utilize cell lines that express the relevant receptor on their surface and determines the amount of cell bound tracer in the presence of various concentrations of potential antagonists. Additionally, other assays utilize membrane extracts from cell lines that express the relevant receptor, and tracer binding is followed by filter binding (see Nenquest Drug Discovery System: Human Tumor Necrosis Factor-Alpha, NEN Research Products, E. I. DuPont de Nemours & Co. (Inc.), Boston, Mass.) or by immobilizing the membrane extracts onto solid supports (Urdal et al., (1988) *J Biol Chem* 263:2870–2877; Smith et al., (1991) *Bioch Bioph Res Comm* 176:335–342). Receptor induced electrophoretic mobility shift of tracer has been applied to identify the presence and size of cell surface receptors by crosslinking the receptor to the tracer and then analyzing on denaturing gels (for example see Kull et al., (1985) *Proc natl Acad Sci USA* 82:5756–5760; Hohmann et al., (1989) *J Biol Chem* 264:14927–14934; Stauber et al., (1989) *J Biol Chem* 264:3573–3576). The use of native gels and non-crosslinked complexes has not been described for growth factors or lymphokines and their receptors, but has been widely applied to study nucleic acid protein interactions (Sambrook et al., (1989) *Molecular Cloning: A Laboratory Manual*, Cold Spring Harbor Laboratory, Cold Spring Harbor, N.Y.).

Screening of various cancer cell lines for the presence of hKGF receptors by PCR, revealed that all carcinoma cell lines express hKGF receptor MRNA while sarcoma cell lines do not. The presence of MRNA does not necessarily mean that hKGF receptor will be present on the surface of these cells. For hKGF, only cell based assays have been described using Balb/MK keratinocytes (Weissman, (1983) *Cell* 32: 599–606) or NIH/3T3 cells transfected with the hKGF receptor (Miki, (1992) *Proc. Natl. Acad. Sci. USA* 89:246–250).

SELEX

A method for the in vitro evolution of nucleic acid molecules with highly specific binding to target molecules has been developed. This method, Systematic Evolution of Ligands by EXponential enrichment, termed SELEX, is described in United States patent application Ser. No. 07/536,428, entitled "Systematic Evolution of Ligands by Exponential Enrichment," now abandoned, United States patent application Ser. No. 07/714,131, filed Jun. 10, 1991, entitled "Nucleic Acid Ligands," now U.S. Pat. No. 5,475,096, United States patent application Ser. No. 07/931,473, filed Aug. 17, 1992, entitled "Methods for Identifying Nucleic Acid Ligands," now U.S. Pat. No. 5,270,163 (see also WO 91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplfing the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, United States patent application Ser. No. 07/960,093, filed Oct. 14, 1992, entitled "Method for Selecting Nucleic Acids on the Basis of Structure," describes the use of SELEX in conjunction with gel electrophoresis to select nucleic acid molecules with specific structural characteristics, such as bent DNA. United States patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. United States patent application Ser. No. 08/134,028, filed Oct. 7, 1993, entitled "High-Affinity Nucleic Acid Ligands That Discriminate Between Theophylline and Caffeine," describes a method for identifying highly specific nucleic acid ligands able to discriminate between closely related molecules, termed "Counter-SELEX." United States patent application Ser. No. 08/143,564, filed Oct. 25, 1993, entitled "Systematic Evolution of Ligands by EXponential Enrichment: Solution SELEX," now abandoned (see U.S. Pat. No. 5,567,588), describes a SELEX-based method which achieves highly efficient partitioning between oligonucleotides having high and low affinity for a target molecule. United States patent application Ser. No. 07/964,624, filed Oct. 21, 1992, entitled "Nucleic Acid Ligands to HIV-RT and HIV-1 Rev," now issued as U.S. Pat. No. 5,496,938, describes methods for obtaining improved nucleic acid ligands after SELEX has been performed. United States patent application Ser. No. 08/400,440, filed Mar. 8, 1995, entitled "Systematic Evolution of Ligands by EXponential Enrichment: Chemi-SELEX," now issued as U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in United States patent application Ser. No. 08/117,991, filed Sep. 8, 1993, entitled "High Affinity Nucleic Acid Ligands Containing Modified Nucleotides," now abandoned (see, U.S. Pat. No. 5,660,985), that describes oligonucleotides containing nucleotide derivatives chemically modified at the 5- and 2'-positions of pyrimidines. United States patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). United States patent application Ser. No. 08/264,029, filed Jun. 22, 1994, entitled "Novel Method of Preparation of Known and Novel 2'-Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide fimctional units as described in United States patent application Ser. No. 08/284,063, filed Aug. 2, 1994, entitled "Systematic Evolution of Ligands by Exponential Enrichment: Chimeric SELEX", now U.S. Pat. No. 5,637,459, and United States patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing nucleic acid ligands to transforming growth factor beta (TGFβ), platelet-derived growth factor (PDGF), and human keratinocyte growth factor (hKGF), and homologous proteins, and the nucleic acid ligands so identified and produced. For the purpose of this application, TGFβ includes human TGFβ1, TGFβ2, and TGFβ3 and TGFβ's that are substantially homologous thereto. By substantially homologous it is meant a degree of amino acid sequence identity of 70% or more. For the purposes of this application, PDGF refers to PDGF AA, AB, and BB isoforms and homologous proteins. Specifically included in the definition are human PDGF AA, AB and BB isoforms. In particular, RNA sequences are provided that are capable of binding specifically to TGFβ1, PDGF, and hKGF. Also provided are ssDNA sequences that are capable of binding specifically to TGFβ and PDGF. Specifically included in the invention are the RNA ligand sequences shown in Tables 3, 13, 16, and 23 (SEQ ID NOS:12–42, 128–170, 189–262, 272–304). The RNA ligand sequences of TGFβ shown in Table 3 include both pre and post SELEX modifications. Also included in the invention are ssDNA ligands of TGFβ and PDGF shown in Tables 6, 8, 9, and FIGS. 3, 4, and 9 (SEQ ID NOS:55–89, 93–124, 171–176). Also included in this invention are RNA ligands of TGFβ1 and hKGF that inhibit the function of TGFβ1 and hKGF, presumably by inhibition of the interaction of TGFβ and hKGF with their receptors. Also included in this invention are ssDNA ligands of PDGF that inhibit the function of PDGF, presumably by inhibition of the interaction of PDGF with its receptor.

Further included in this invention is a method of identifying nucleic acid ligands and nucleic acid ligand sequences to a target selected from the group consisting of TGFβ, PDGF, and hKGF comprising the steps of (a) contacting a candidate mixture of nucleic acids with the target (b) partitioning between members of said candidate mixture on the basis of affinity to the target and (c) amplifying the selected molecules to yield a mixture of nucleic acids enriched for nucleic acid sequences with a relatively higher affmity for binding to the target.

More specifically, the present invention includes the RNA and ssDNA ligands to TGFβ identified according to the above-described method, including those ligands shown in Tables 3 and 6 (SEQ ID NOS:12–42, 55–89). Also included are nucleic acid ligands to TGFβ that are substantially homologous to any of the given ligands and that have substantially the same ability to bind TGFβ and inhibit the function of TGFβ. Further included in this invention are nucleic acid ligands to TGFβ that have substantially the same structural form as the ligands presented herein and that have substantially the same ability to bind TGFβand inhibit the function of TGFβ.

Additionally, the present invention includes the ssDNA and RNA ligands to PDGF identified according to the above-described method, including those ligands shown in Tables 8 and 13, and FIGS. 3, 4, and 9 (SEQ ID NOS:93–124, 128–176). Also included are DNA and RNA ligands to PDGF that are substantially homologous to any of the given ligands and that have substantially the same ability to bind PDGF. Further included in this invention are nucleic acid ligands to PDGF that have substantially the same structural form as the ligands presented herein and that have substantially the same ability to bind PDGF.

In addition, the present invention includes the RNA ligands to hKGF identified according to the above-described method, including those ligands shown in SEQ ID NOS: 189–264, 268–304. Also included are RNA ligands to hKGF that are substantially homologous to any of the given ligands and that have substantially the same ability to bind hKGF and inhibit the interaction of hKGF with its receptor. Further included in this invention are nucleic acid ligands to hKGF that have substantially the same structural form as the ligands presented herein and that have substantially the same ability to bind hKGF and inhibit the interaction of hKGF with its receptor.

The present invention also includes other modified nucleotide sequences based on the RNA ligands identified herein and mixtures of the same.

Further included in this invention is a method of assaying a test compound for the ability to inhibit hKGF receptor-mediated cell proliferation comprising the steps of (a) contacting the test compound with a hKGF nucleic acid ligand and a keratinocyte growth factor; and (b) detecting the ability of the test compound to inhibit binding between the hKGF nucleic acid ligand and the keratinocyte growth factor.

Also included in this invention is a method of assaying a test compound for the ability to inhibit the interaction of a growth factor with its plasma membrane bound receptor comprising the steps of (a) solubilizing cells containing the plasma membrane bound receptor; (b) creating a plasma membrane extract of the cells; (c) reacting the extract with labeled growth factor alone and in the presence of the test compound thereby creating complexes; (d) analyzing the complexes by electrophoresis under native conditions; (e) visualizing the complexes by imaging; and (f) comparing the image of the extract with labeled growth factor alone to the image of the extract in the presence of the test compound to determine whether the test compound inhibited the interaction between the growth factor and its plasma membrane bound receptor.

Further included in this invention is a method for assaying cells to determine whether they express a growth factor plasma membrane bound receptor comprising the steps of (a) solubilizing the cells; (b) creating a plasma membrane extract of the cells; (c) reacting the plasma membrane extract with a labeled growth factor; (d) analyzing the reaction between the plasma membrane extract with the labeled growth factor by electrophoresis under native conditions; (e) comparing the electrophoresis of step (d) with electrophoresis of labeled growth factor; and (f) visualizing the results of the electrophoresis to determine whether a complex is formed with altered mobility relative to the mobility of a labeled growth factor alone.

BRIEF DESCRIPTION OF THE FIGURES

FIG. 4 shows the minimal ligands 20t, 36t and 41t folded according to the consensus secondary structure motif. [3'T] represents a 3'—3' linked thymidine nucleotide added to reduce 3'-exonuclease degradation.

FIGS. 12A and 12B show the proposed alignment of 2'F ligands. The majority of 2'F ligands can be folded into pseudoknot structures. Two classes are proposed as shown. The summary structure for each class is also shown. Bases participating in stem 1 (S1) are underlined with single lines while bases of stem 2 (S2) are underlined with double lines. Spaces were introduced for alignment of the various elements of the pseudoknots.

FIGS. 12C and 12D show the proposed folding of 2'NH$_2$ ligands. These ligands are assigned into two classes. As shown in the summary structures, class 1 and class 2 ligands can form a stem-loop and dumbbell structure, respectively. Spaces were introduced to allow sequence alignment. Residues participating in stems are underlined. In the summary structures, periods (.) indicate a variable number of residues. Ligands 2N and 54N are circular permutations of the same dumbbell structure. For alignment of the corresponding loops these ligands are wrapped around two lines.

DETAILED DESCRIPTION OF THE INVENTION

Figure 1:
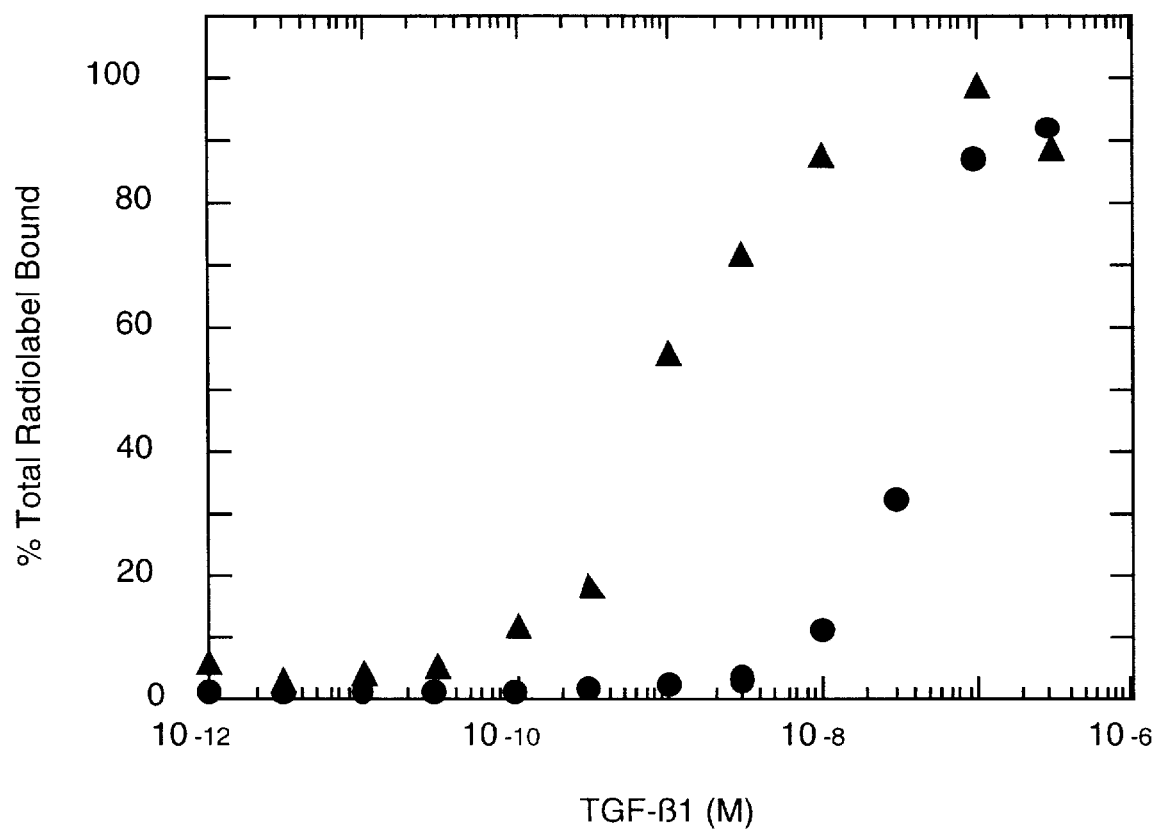
FIG. 1 shows the binding analysis of the 40D7 DNA library for TGFβ1. Binding data obtained from Round 19 (triangles) and Round 0 (circles) are shown.

This application describes high-affmity nucleic acid ligands to TGFβ, PDGF, and hKGF identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096 and United States patent application Ser. No. 07/931,473, filed Aug. 17, 1992, entitled Methods for Identifying Nucleic Acid Ligands, now United States Pat. No. 5,270,163, (see also WO 91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The nucleic acid ligands described herein can be complexed with a lipophilic compound (e.g., cholesterol) or attached to or encapsulated in a complex comprised of lipophilic components (e.g., a liposome). The complexed nucleic acid ligands can enhance the cellular uptake of the nucleic acid ligands by a cell for delivery of the nucleic acid ligands to an intracellular target. U.S. patent application Ser. No. 08/434,465, filed May 4, 1995, entitled "Nucleic Acid Ligand Complexes," now U.S. Pat. No. 6,011,020 which is incorporated in its entirety herein, describes a method for preparing a therapeutic or diagnostic complex comprised of a nucleic acid ligand and a lipophilic compound or a non-immunogenic, high molecular weight compound.

The methods described herein and the nucleic acid ligands identified by such methods are useful for both therapeutic and diagnostic purposes. Therapeutic uses include the treatment or prevention of diseases or medical conditions in human patients. Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands described herein may specifically be used for identification of the TGFβ, PDGF, and hKGF proteins.

SELEX provides high affinity ligands of a target molecule. This represents a singular achievement that is unprecedented in the field of nucleic acids research. The present invention applies the SELEX procedure to the specific targets of TGFβ, PDGF, and hKGF. In the Example section below, the experimental parameters used to isolate and identify the nucleic acid ligands to TGFβ, PDGF, and hKGF are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), now U.S. Pat. No. 5,496,938, methods are described for obtaining improved nucleic acid ligands after SELEX has been performed. The '624 application, entitled Nucleic Acid Ligands to HIV-RT and HIV-1 Rev, is specifically incorporated herein by reference. Further included in this patent are methods for determining the three-dimensional structures of nucleic acid ligands. Such methods include mathematical modeling and structure modifications of the SELEX-derived ligands, such as chemical modification and nucleotide substitution.

In the present invention, SELEX experiments were performed in order to identify RNA and DNA ligands with specific high affinity for TGFβ1 from degenerate libraries containing 40 or 60 random positions (40N or 60N) (Tables 1 and 5). This invention includes the specific RNA ligands to TGFβ1 shown in Table 3 (SEQ ID NOS:12–42), identified by the methods described in Examples 1 and 2. This invention furer includes RNA ligands to TGFβ which inhibit TGFβ1 function, presumably by inhibiting the interaction of TGFβ1 with its receptor. This invention includes the specific ssDNA ligands to TGFβ1 shown in Table 6 (SEQ ID NOS:55–89) identified by the methods described in Examples 5 and 6.

In the present invention, two SELEX experiments were also performed in order to identify ssDNA and RNA with specific high affinity for PDGF from degenerate libraries containing 40 and 50 random positions (40N and 50N), respectively (Tables 7 and 12). This invention includes the specific ssDNA and RNA ligands to PDGF shown in Tables 8, 9 and 13 and FIGS. 3, 4, and 9 (SEQ ID NOS:93–124, 128–176 ), identified by the methods described in Examples 7 and 15.

In the present invention, a SELEX experiment was also performed in search of RNA ligands with specific high affinity for hKGF from degenerate libraries containing 40 random positions (40N) (Table 14). This invention includes the specific RNA ligands to hKGF shown in Tables 16 and FIG. 12 (SEQ ID NOS :1 89–262, 268–304), identified by the methods described in Examples 16 and 17. This invention further includes RNA ligands to hKGF which inhibit the interaction of hKGF with its receptor.

The scope of the ligands covered by this invention extends to all nucleic acid ligands of TGFβ, PDGF, and hKGF, modified and unmodified, preferably those identified according to the SELEX procedure. More specifically, this invention includes nucleic acid sequences that are substantially homologous to the ligands shown in Tables 3, 6, 8, 9, 13, 16, and 23 and FIGS. 3, 4, 9 and 12 (SEQ ID NOS:12–42, 55–89, 93–124, 128–176, 189–262, 268–304). By substantially homologous it is meant a degree of primary sequence homology in excess of 70%, most preferably in excess of 80%. A review of the sequence homologies of the nucleic acid ligands shown in Tables 3 and 6 (SEQ ID NOS.: 12–42, 55–89) for TGFβ, Tables 8 and 13 (SEQ ID NOS:93–124, 128–170) for PDGF, and Tables 16 and 23 (SEQ ID NOS: 189–262, 272–304) for hKGF shows that sequences with little or no primary homology may have substantially the same ability to bind a given target. For these reasons, this invention also includes nucleic acid ligands that have substantially the same structure and ability to bind TGFβ, PDGF, and hKGF as the nucleic acid ligands shown in Tables 3, 6, 8, 9, 13, 16, and 23 and FIGS. 3, 4, 9 and 12 (SEQ ID NOS: 12–42, 55–89, 93–124, 128–176, 189–262, 268–304). Substantially the same structure for PDGF includes all nucleic acid ligands having the common structural elements shown in FIG. 3 that lead to the affinity to PDGF. Substantially the same ability to bind TGFβ, PDGF, or hKGF means that the affinity is within one or two orders of magnitude of the affinity of the ligands described herein. It is well within the skill of those of ordinary skill in the art to determine whether a given sequence—substantially homologous to those specifically described herein—has substantially the same ability to bind TGFβ, PDGF, or hKGF.

This invention also includes the ligands as described above, wherein certain chemical modifications are made in order to increase the in vivo stability of the ligand or to enhance or mediate the delivery of the ligand. Examples of such modifications include chemical substitutions at the sugar and/ or phosphate and/or base positions of a given nucleic acid sequence. See, e.g., U.S. patent application Ser. No. 08/117,991, filed Sep. 8, 1993, entitled High Affinity Nucleic Acid Ligands Containing Modified Nucleotides now abandoned (see U.S. Pat. No. 5,660,985) which is specifically incorporated herein by reference. Other modifications are known to one of ordinary skill in the art. Such modifications may be made post-SELEX (modification of previously identified modified or unmodified ligands) or by incorporation into the SELEX process.

Example 20 describes post-SELEX procedure modification of a nucleic acid ligand to basic fibroblast growth factor (bFGF). The nucleic acid ligand was modified by the addition of phosphorothioate caps and substitution of several ribopurines with 2'-deoxy-2'-O-methylpurines.

As described above, because of their ability to selectively bind TGFβ, PDGF, and hKGF, the nucleic acid ligands to TGFβ, PDGF, and hKGF described herein are useful as pharmaceuticals. This invention, therefore, also includes a method for treating TGF-β-mediated pathological conditions by administration of a nucleic acid ligand capable of binding to TGFβ, a method for treating PDGF-mediated pathological conditions by administration of a nucleic acid ligand capable of binding to PDGF, and a method for treating hKGF-mediated pathological conditions by administration of a nucleic acid ligand capable of binding to hKGF.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following examples are provided to explain and illustrate the present invention and are not intended to be limiting of the invention. Examples 1–4 describe initial experiments to identify RNA with specific high affinity for TGFβ1. Example 1 describes the various materials and experimental procedures used in Examples 2–4. Example 2 describes a representative method for identifying RNA ligands by the SELEX method which bind TGFβ1. Example 3 describes the affinities the ligands have for TGFβ1 and demonstrates that the ligands are capable of inhibiting the function of TGFβ1, presumably by inhibiting the interaction of TGFβ1 with its receptor. Example 4 describes which regions of the ligands are believed to be necessary for TGFβ1 binding and inhibition of TGFβ1 receptor binding. Example 5 describes another representative method for identifying RNA and DNA ligands by the SELEX method which bind TGFβ1. Example 6 reports on the binding analysis, bioassay, and sequences of a ssDNA SELEX library. Example 7 describes the various materials and experimental procedures used in evolving ssDNA ligands to PDGF described in Examples 8–13. Example 8 describes the ssDNA ligands to PDGF and the predicted secondary structure of selected nucleic acid ligands. Example 9 describes the minimal sequence necessary for high affinity binding. Example 10 describes the kinetic stability of PDGF-Nucleic Acid Ligand complexes. Example 11 describes the thermal melting properties for selected ligands. Example 12 describes photo-crosslinking of nucleic acid ligands and PDGF. Example 13 describes the inhibition by DNA ligands of PDGF isoforms on cultured cells and inhibition of the mitogenic effects of PDGF in cells by DNA ligands. Example 14 describes the modification of nucleic acid ligands to PDGF with modified nucleotides. Example 15 describes the experimental procedures used in evolving RNA ligands to PDGF and shows the ligand sequences. Example 16 describes the various materials and experimental procedures used in evolving nucleic acid ligands to hKGF described in Examples 17–19. Example 17 describes the RNA ligands to hKGF, the affinities the ligands have for hKGF, and the specificity of the RNA ligands to hKGF. Example 18 describes inhibition of hKGF binding to cell surface receptors. Example 19 reports on the inhibition of mitogenic activity of hKGF by a selected ligand. Example 20 describes the modification of nucleic acid ligands to bFGF with 2'-deoxy-2'-O-methylpurines.

EXAMPLES

Example 1

Experimental Procedures

This example provides the general procedures followed and incorporated in Examples 2–4.

A. Materials

Human recombinant TGFβ1 used in this SELEX procedure was acquired from Genentech. Human recombinant TGFβ1 can also be purchased from R&D systems, Minneapolis, Minn., USA.

Biotinylated TGFβ1 was prepared by reacting TGFβ1 at 3.6 μM with an 11 fold molar excess of sulfo-NHS-biotin (Pierce, Rockford, Ill., USA) in 50 mM NaHCO$_3$ for 3 hr. in an ice bath. The reaction was acidified with 0.036 volumes of 10% acetic acid and applied to a 40 mg Vydac (The Separations Group, Hesperia, Calif., USA) reverse phase column made in a siliconized pipet tip to separate unreacted biotin from biotinylated TGFβ1. The column was prewashed with 200 μl ethanol followed by 200 μl 1% acetic acid, the biotinylation reaction was applied, free biotin was washed through with 200 μl of 50 mM sodium acetate pH 5.5, followed by 200 μl of 20% acetonitrile and finally eluted with 200 μl of 60% acetonitrile. The sample was lyophilized and resuspended in 50 mM sodium acetate pH 5.0 at 40 μM and stored at 4° C. The TGFβ1 was spiked with 100,000 cpm iodinated TGFβ1 in order to follow recovery and to assess the success of the biotinylation reaction by measuring the fraction of the radioactivity that would bind to streptavidin coated agarose beads (Pierce) before and after biotinylation. An aliquot of the TGFβ1 before and after biotinylation was subjected to analytical reverse phase chromatography. The biotinylated TGFβ1 substantially ran as a single peak which was retarded with respect to the unbiotinylated TGFβ. A small amount (5 %) of unreacted TGFβ1 could be detected. The efficiency of binding of the iodinated, biotinylated TGFβ1 to streptavidin (SA) agarose beads (30 μl) was 30% under the binding conditions used for SELEX partitioning.

Iodinated TGFβ1 was prepared by the lactoperoxidase method (50 mM sodium phosphate pH 7.3, 0.16% glucose) with BioRad Enyymo beads (BioRad, Richmond, Calif., USA) and the bound iodine separated from the free iodine by gel filtration on G25 Sephadex in 50 mM sodium acetate 0.01% Tween.

The mink lung cell line expressing the luciferase reporter gene under the control of PAI 1 promoter (Abe et al. (1994) *Anal. Biochem.* 216:276–284) was a gift from Dr. Dan Rifkin (Department of Cell Biology, New York Medical Center, New York, N.Y. 10016). Luciferase was assayed by reagents purchased from Analytical Luminescence Laboratory, San Diego, Calif., USA.

2'- NH$_2$ modified CTP and UTP were prepared according to the method of Pieken et al. (1991) *Science* 2:314–317. DNA oligonucleotides were synthesized using standard procedures either at NeXstar Pharmaceuticals, Inc. (Boulder, Colo., USA) or by Operon Technologies (Alameda, Calif., USA). All other reagents and chemicals were purchased from standard commercial sources and sources have been indicated.

B. SELEX Procedure

SELEX ligands that bind to TGFβ1 were derived essentially as described in U.S. Pat. No. 5,270,163 (see also, Tuerk and Gold (1990) Science 249:505–510). To generate the starting pool of PCR template, PCR product from twenty separate PCR reactions each containing 16.1 pmol of unpurified, single stranded DNA (at least a total of $2 \times 10^{12}$ to $2 \times 10^{13}$ different molecules) were pooled before the first transcription. PCR conditions were 50 mM KCl, 10 mM Tris-HCl, pH 9, 0.1% Triton-X100, 1.5 mM MgCl$_2$, 0.2 mM of each dATP, dCTP, dGTP, and dTTP, 2 μM each primer and 0.075 units/μl of Taq DNA polymerase, 100 μl per reaction in a siliconized microfuge tube. All PCR cycles took advantage of hot start using Ampliwax (Perk and Elmer, Norwalk, Conn., USA). Duration of the initial PCR was 10 cycles; a PCR cycle was 94° C-1', 52° C-1', 72° C-2'. An initial denaturation was 94° C. for 4' and the final extension at 72° C. for 5'. PCR reactions were combined, phenol/chloroform extracted, and isopropanol precipitated (2.0 M ammonium acetate, 50% isopropanol) to remove primers.

Transcription reactions contained 200 nM DNA, 0.9 mM GTP, 0.9 mM 2'-NH$_2$-UTP, 0.9 mM 2'-NH$_2$-CTP, 0.5 mM ATP, 87 mM Tris-HCl pH 8.0, 17 mM MgCl$_2$, 4.4 mM spermidine, 22 mM DTT, 100 μg/ml acetylated BSA (Promega, Madison, Wis., USA) and 4 units/μl T7 RNA polymerase. (2'-F-UTP and 2'-F-CTP (United States Biochemical, Cleveland, Ohio, USA) were used at 3.0 mM, whereas UTP and CTP were used at 0.9mM each). Transcription reactions were incubated overnight at 28° C. (at least 10 hours). After transcription the template was digested by addition of 2 μl RQ1 Dnase (Promega) for 15' at 28° C., and then extracted with phenol/CHCl$_3$, followed by three ethanol precipitations from ammonium acetate (3.9M ammonium acetate, 72% ethanol).

The RNA molecules were incubated with TGFβ1 bound to SA agarose beads as described below in Krebs-Ringer solution (KR) (120 mM NaCl, 4.8 mM KCl, 10 mM Na phosphate buffer pH 7.4, 1.2 mM MgSO$_4$, 2.6 mM CaCl$_2$) modified to include 20 mM Na-Hepes pH 7.5 and 0.2% Triton X100 (Pierce). This buffer is referred to as KRHT.

TGFβ1-RNA complexes were separated from unbound RNA by washing the beads. Recovery of the selected 2'-NH$_2$ or F pyrimidine modified RNA from the agarose beads required guanidine thiocyanate extraction (5M GnSCN, 10 mM Tris-HCl, 0.1 mM EDTA, pH 7.0, 0.1M beta mercaptoethanol) or from Seradyne SA coated beads by 2% SDS (0.1 M Tris-HCl pH 7.5, 50 mM NaCl, 1 mM Na$_2$EDTA, 2% SDS, 1.5 mM DTT). Regular 2'-OH RNA was easily recovered under less harsh conditions with the same buffer used for the Seradyne beads containing only 0.2% SDS. After extraction and precipitation to purify and concentrate the RNA, the sample was reverse transcribed with a cloned MMLV RT with the RNase H sequence deleted. The reaction contained less than or equal to 16 nM RNA, 10 μM 3' primer, 50 mM Tris-HCl pH 8.3, 75 mM KCl, 5 mM MgCl$_2$, 10 mM DTT, 0.5 mM dNTP's. Prior to addition of buffer the RNA and the primer were boiled together. After addition of buffer and salts the reaction was annealed for 10 min at 28° C. before addition of 600 units of Superscript reverse transcriptase (Bethesda Research Labs, Gaithersburg, Md., USA) and synthesis at 50° C. for 1 hour.

PCR amplification of this cDNA (<1 pmol) resulted in approximately 250 pmol double-stranded DNA, of this, 40 pmols was transcribed and used to initiate the next round of SELEX.

C. Partitioning Method for SELEX 2.5 pmols biotinylated TGFβ1 were bound to 30 μl SA agarose beads (Pierce) in 200 1l KRHT. The mixture was incubated on a rotator at 37° C. for 15 to 30 minutes. The beads were washed three times by centrifugation and resuspension in 200 μl cold KRHT to remove unbound TGFβ1, and resuspended in a final volume of 500 μl KRHT. RNA containing 2'-NH$_2$ pyrimidines was heated at 70° C. for three minutes (RNAs containing 2'-OH or 2'-F pyrimidines were heated at 95° C.) and diluted into KRHT containing TGFβ1 bound to SA beads. The final concentration of RNA is 1 μM and the TGFβ1 was 5 nM. Binding occurs with rotation at 37° C. for 30 minutes. Beads were washed by centrifugation and resuspension three times with 200 μl binding buffer to remove unbound RNA. RNA was eluted from the beads as described above.

D. Binding Assays

Two binding assays for ligands to TGFβ1 gave equivalent results wherever tested. In the SA bead assay the biotinylated TGFβ1 was serially diluted in KRHT in polypropylene tubes (Linbro, ICN, Irvine, Calif., USA) and bound to the beads as described above. After unbound TGFβ1 was washed away, trace quantities of $^{32}$P-labeled RNA(<0.1 nM) were added to each tube and vortexed to mix. After static incubation at 37° C. for 30 minutes, the unbound RNA was removed by washing three times with 200 μl of KRHT.

In the nitrocellulose filter binding assay, TGFβ1 was serially diluted in KRH containing 0.1% defatted BSA (Fluka radioimmunoassay grade, Fluka, Hauppauge, N.Y., USA) as carrier instead of Triton X-100. Incubation with RNA tracer was as above. Samples were pipetted with a multiwell pipettor onto a multiwell manifold holding a sheet of wet BioRad 0.45 micron nitrocellulose, aspirated, and washed three times with 200 μl KRH (containing no BSA). The filters were air dried and counted in a liquid scintillation counter (Beckmann Instruments, Palo Alto, Calif.).

The equation used to fit the binding of ligands to TGFβ1 describes the binding of a ligand to a receptor (in this case TGFβ1) that follows the laws of mass action and for which there is a single binding site: $Y=B_{max}*X/(Kd+X)$: where $Y$ is the fraction of the ligand bound, $B_{max}$ is the maximum fraction of the ligand bound, $X$ is the concentration of TGFβ1 and Kd is the dissociation constant of TGFβ1 and the ligand. Data points were fit by nonlinear regression using the computer program Graphpad Prism (Graphpad Software, San Diego, Calif.). The algorithm minimized the sum of the squares of the actual distance of the points from the curve. Convergence was reached when two consecutive iterations changed the sum-of-squares by less than 0.01%.

E. Cloning and Sequencing

SELEX experiments are described in Table 2. Primers for SELEX experiments 1 and 2 shown in Table 1 contain recognition sites for the restriction endonucleases SacI (5' primer T7SacBam; SEQ ID NO:7) and XbaI (3' primer 3XH; SEQ ID NO:9). PCR products from SELEX experiments 1 and 2 were cloned directionally into SacI/XbaI digested pgem 9zf (Promega). 5' primer T7SB2N (SEQ ID NO:8) and 3' primer 3XH (SEQ ID NO:9) (Table1) were used for SELEX experiments 3–9. PCR products from SELEX experiments 3–9 were cloned directionally into the BamHl/XbaI site of a modified pGem9zf:BamH1 cloning vector. The BamH1 site was engineered into pGem9zf in the following way. A clone isolated from library 2 (lib2-6-2) that did not bind to TGFβ1 (sequence not shown) was digested with BamH1 and XbaI. The sequence flanking the cloning site of the modified pGem9zf vector is shown in Table 1 (SEQ ID NOS:10–11).

After digestion of the plasmid with restriction endonuclease and dephosphorylation with CIP (calf intestinal phosphatase), vectors were gel purified. Inserts were ligated and recombinant plasmids were transformed into *E. coli* strain DH10B (Bethesda Research Labs). Plasmid DNA was prepared by alkaline lysis, mini prep procedure. Twenty-two clones representing 9 unique sequences were sequenced at random from libraries 1 and 2. 50 clones were sequenced from libraries 3–9 using a single dideoxy G reaction (called G track). The sequencing ladders were compared and organized for similarities. Selected clones from each family were chosen for complete sequence analysis. TGFβ1 binding assays were performed on transcripts representing different G sequences in each library. Out of a total of 140 binding assays, 27 ligands bound with a Kd less than 10 nM, and 21 of these were sequenced. Clones were sequenced with the Sequenase sequencing kit (United States Biochemical Corporation, Cleveland, Ohio).

F. Ligand Truncation

Truncation experiments were carried out to determine the minimal sequence necessary for high affinity binding of the RNA ligands to TGFβ1. For 3' boundary determination, RNA ligands were 5' end-labeled with γ-$^{32}$P-ATP using T4 polynucleotide kinase. 5' boundaries were established with 3' end-labeled ligands using α-$^{32}$P-pCp and T4 RNA ligase. After partial alkaline hydrolysis, radiolabeled RNA ligands were incubated with TGFβ1 at concentrations ranging from 1 nNM to 50 nM and protein-bound RNA was separated by nitrocellulose partitioning. RNA truncates were analyzed on a high-resolution denaturing polyacrylamide gel. A ladder of radioactively labeled ligands terminating with G-residues was generated by partial RNase T1 digestion and was used as markers.

G. Inhibition of TGFβ1 Function

TGFβ1 signal transduction begins with binding to a cell surface receptor and results in the induction of transcription of a variety of genes. One of these genes is Pail. The TGFβ1 assay utilizes the mink lung epithelial cell (MLEC) carrying the luciferase reporter gene fused to the Pai 1 promoter. The MLEC has TGFβ1 receptors on its cell surface. Thus one can measure the response of the cells to TGFβ1 and the effective concentration of TGFβ1 in the culture media by measuring the luciferase enzyme activity after a period of induction.

Mink lung epithelial cells (MLEC) carrying the Pai1/luc construct were maintained in DME containing 10% fetal bovine serum and 400 μg/ml G418. MLEC-Pai1/luc cells were plated at 3.2×10$^4$ cells per well in a 96 well Falcon plate, in 100 μl of DME+10% fetal bovine serum overnight. Media was made from autoclaved water. The cells were washed three times (100 μl) in serum free DME plus Solution A (1:1). Solution A is 30 mM Hepes pH 7.6, 10 mM glucose, 3.0 mM KCl, 131 mM NaCl, 1.0 mM disodium phosphate. Samples (100 μl) were added in DME containing 20 mM Hepes pH 7.5, and 0.1% BSA (Fluka, radioimmunoassay grade). All samples were in triplicate. After six hours at 37° C. in a 5% CO$_2$ incubator the media was removed and cells were washed three times (100 μl each) in cold PBS. Lysis buffer (75 μl) (Analytical Luminescence Laboratory) was added and the plates incubated on ice for 20 min. The plates were sealed and frozen at −80° C. until assayed. Samples (25 μl) were assayed for luciferase activity with the Enhanced Luciferase Assay Kit from Analytical Luminescence Laboratory (San Diego, Calif., USA) according to the manufacturers instructions using the Berthold Microlumat LB96P luminometer. Luminescence is reproducibly a finction of TGFβ1 concentration added to the media.

Ligands tested for inhibition of TGFβ1 activity were tested at a minimum of five concentrations. The ligands were serially diluted in DME, 20 mnM Hepes pH 7.5, 0.1% Fluka BSA in polypropylene tubes and an equal volume of media containing 12 pM TGFβ1 was added to each tube, vortexed and transferred to the cells without further incubation. From the TGFβ1 standard curve included on every plate the effective concentration of TGFβ1 in the presence of the inhibitory ligands was determined by the reduction in luminescence measured. Some ligands were tested at both 3 pM and 6 pM TGFβ1 with the same results. To determine the $IC_{50}$ (the concentration of SELEX ligand necessary to reduce the TGFβ1 activity 50%), the five values obtained for each ligand were plotted and the value at 50% inhibition was determined graphically using Graphpad Prism assuming a hyperbolic fit of the data and using non-linear regression.

Example 2

RNA Ligands to TGFβ1

A. SELEX Experiments

In order to generate RNA ligands to TGFβ1, nine SELEX experiments, as summarized in Table 2, were performed using the methods described in Example 1. As shown in Table 1, the RNA pools differ in the number of random bases present in the central portion of the molecules: 40 nucleotides in the 40N6 (SEQ ID NO:2) SELEX and 64 nucleotides in the 64N6 and lib2-6-1RN6 (SEQ ID NOS:1, 3) SELEX experiment. Since the goal was to select RNA ligands that not only bound to TGFβ1 but also blocked receptor binding, the large random region (64N) was chosen. In two experiments, a shorter random region (40N) was also included. Ligands to TGFβ1 were very rare with 40N and were qualitatively the same as the 64N6 ligands selected.

The sequences of clones from the SELEX experiments are shown in Table 3 (SEQ ID NOS:12–42).The pyrimidines used in the various SELEX experiments differed at the 2' position of the sugar (Table 2). In the first two SELEX experiments, ligands were evolved as 2'-OH pyrimidines. Ligands were post-SELEX modified with 2'-NH2 or 2'-F-substituted pyrimidines to see if they retained TGFβ1 binding. Since the 2' substitutions rendered the ligands resistant to RNase A they were also tested in the cell culture assay for inhibition of TGFβ1 activity. One such ligand lib2-6-1 (Group D, Table 3; SEQ ID NO:35) when substituted with 2'-NH$_2$-UTP and 2'-F-CTP was shown to inhibit TGFβ1 receptor mediated activity. To select more ligands, six more independent SELEX experiments (lib3-7 and lib9) were performed using the 2'-F and 2'-NH$_2$-substituted pyrimidines during the evolution process. In experiment lib8 the biologically active clone lib2-6-1 (SEQ ID NO:35) was randomized and subjected to re-selection to see if the binding and inhibition behavior of the clone could be improved. Lib8 was evolved as a 2'-OH pyrimidine RNA. In some cases, post-SELEX modification of TGFβ1 ligands derived from experiments 3–9 were performed, e.g., to determine if a ligand evolved with 2'-F pyrimidine substitutions would also bind with 2'-NH$_2$ substitutions.

Each starting pool for a SELEX experiment contained $3 \times 10^{14}$ RNA molecules (500 pmol). The affinity of the starting RNA for TGFβ1 was estimated to be greater than 50 mM. After 4 rounds of SELEX, the affinities of the evolving pools had improved to approximately 10 nM and did not shift significantly in subsequent rounds. RNA was bulk sequenced and found to be non-random and cloned.

Lib1 took 20 rounds to evolve since optimum concentrations of TGFβ1 were not used until round 15 and libraries 5, 6 and 7 took longer to evolve because optimum conditions for recovery of bound ligands during the partitioning step in SELEX were not introduced until round 8. Optimum TGFβ1 concentrations and partitioning conditions are described in Example 1.

B. RNA Sequenes

Many clones in a SELEX library are identical or similar in sequence. The libraries were screened by G track and only representatives of each G track type were tested in a binding assay. The binding assay was five points (16.5 nM, 5.5 nM, 1.8 nM, 0.6 nM, and 0.2 nM) and could detect only those SELEX clones with a Kd less than or equal to 10 nM. RNA ligands that bound well (Kd<10 nM) in the binding assay were sequenced. The sequences were inspected by eye and analyzed using computer programs which perform alignments and fold nucleic acid sequences to predict regions of secondary structure. Ligands were classified into five groups (A, B, C, D, and orphans) by sequence homology. Each group has characteristic allowable 2' substitutions.

58 clones were identified by G track from 7 separate SELEX experiments to belong to group A ligands (Table 3; SEQ ID NOS:12–42). 15 clones were sequenced; 13 were similar but not identical, whereas 3 clones, lib3-13 (SEQ ID NO:12), lib5-6 and lib5-13, were identical. Group A ligands were recovered from seven of the eight SELEX libraries which included libraries evolved as 2'-NH$_2$, 2'-OH or 2'-F-substituted pyrimidines as well as a library evolved as 2'-F-UTP, 2'-NH$_2$-CTP. Post SELEX modification indicates that 2'-NH$_2$-UTP, 2'-F-CTP does not disrupt binding of lib8-9 to TGFβ1, thus the structure of Group A ligands appears to not require a specific 2' moiety on the pyrimidine sugar in order to maintain binding.

Group B ligands bind both as 2'-NH$_2$ and 2'-F pyrimidine substituted RNA. 28 Group B clones were detected by G track analysis from 3 libraries. Two of the libraries were evolved as 2'-NH$_2$ and one as 2'-F library. Four clones were sequenced, two were identical (lib5-47 and lib4-12; SEQ ID NO:28). An internal deletion can occur in group B, as in lib 3-44. The 40N orphan, lib3-42 was placed in Group B on the basis of secondary structure. The internal deletion in lib3-44, the binding affinity, the bioactivity and boundary experiments all support the placement of lib3-42 in this group.

Group C ligands bind as 2'-OH or 2'-F ligands as expected, since members of this group were evolved as 2'-OH ligands in lib 1 and as 2'-F pyrimidine substituted ligands in lib 6. Lib1-20-3 (SEQ ID NO:32) was post SELEX modified and as 2'-F derivative. Lib1-20-3 did not bind with 2'-NH$_2$ pyrimidines incorporated.

Group D ligand, lib2-6-1 (SEQ ID NO:35), was isolated after 2'-OH SELEX but was post SELEX modified and binds well as a 2'-NH$_2$-UTP and 2'-F-CTP pyrimidine derivative. Lib2-6-1 does not bind well to TGFβ1 with 2'-NH$_2$, 2'-F or 2'F-UTP, 2'-NH$_2$-CTP-substituted pyrimidines. Variants of Group D were only reselected in two other SELEX experiments, lib8, a 2'-OH library, and lib 9, a 2'-NH$_2$-UTP, 2'-F CTP library, supporting the observation that there is specificity for the 2' pyrimidine position in this ligand.

The group labeled orphans are not homologous to each other and no variant sequences for these ligands have been determined. G track indicates that eight 40N clones similar to lib3-45 were isolated from two libraries. Two of the eight were sequenced and are identical. Lib3-45 (SEQ ID NO:39) binds whether it contains 2'-NH$_2$ or 2'-F substituted pyrimidines or the 2'-F-UTP, 2'-N $_2$-CTP combination. Lib1-20-5 (SEQ ID NO:40) isolated as a 2'-OH ligand binds as a 2'-F, whereas lib-1-20-12 (SEQ ID NO:41) and lib2-6-8 (SEQ ID NO:42) bind well only as 2'-OH pyrimidines and will not tolerate 2'-NH$_2$ or 2'-F post SELEX modifications.

As it was unusual that similar sequences were obtained from different SELEX experiments containing different modifications, another set of SELEX experiments was performed in search of RNA and ssDNA ligands to TGFβ1 as described in examples 5 and 6 infra.

Example 3

Inhibition of TGFβ1 Receptor Binding

The Kds and $B_{max}$ values reported in Table 4 for Group A ligands are for the 2'-NH$_2$ substituted version of the ligand unless otherwise noted. $B_{max}$ for the Group A ligands was 0.38±0.12 (n=14) which is in agreement with the measured retention of TGFβ1 on the nitrocellulose filters. The Kd's for Group A ligands were all similar, 2.2±1.1 nNM (n=14). Where measured nitrocellulose and SA agarose bead binding assays gave equivalent results.

The IC$_{50}$'s in Table 4 for Group A ligands were all tested with the 2'-NH$_2$ pyrimidine substituted ligands except where indicated. 2'-NH$_2$ ligands were used in the tissue culture bio-assay since they exhibited the greatest stability under the conditions of the bio-assay. Five out of ten Group A ligands tested inhibited TGFβ1 receptor activity. IC$_{50}$values for the inhibitors were typically 25 fold above the Kd for TGFβ1. The data are reproducible; the Kd for ligand lib3-13 was 0.83±0.11 nM (n=3) and the IC$_{50}$ for lib3-13 (SEQ ID NO:12) was 25±14 nM (n=4). RNA concentrations in the bioassays are all estimates based on an assumed extinction coefficient and 100% purity of the ligand. The RNA concentrations may, therefore, be overestimated during the bio-assay which in turn would overestimate the IC$_{50}$.

Another five Group A ligands did not inhibit TGFβ1 receptor binding activity. One obvious difference between the non-bioactive ligands, lib2-6-4 (SEQ ID NO:20), lib5-48 (SEQ ID NO:19), and lib6-23 (SEQ ID NO:21), and the bioactive ligands is the substitution at nucleotide 72. Lib7-21 (SEQ ID NO:23) and lib7-43 (SEQ ID NO:24) were tested as 2'-F-UTP, 2'-NH$_2$-CTP ligands for bio-activity. These ligands were not bio-active despite their high affinity to TGFβ. In conclusion, binding and bioactivity are separable functions of the TGFβ Group A ligands.

Group B ligands have different binding properties than Group A ligands (Table 4). Both the Kd (0.63±0.5 nM, n=4) and $B_{max}$ (0.14±0.04, n=4) are lower for Group B ligands. One Group B inhibitor, lib4-12 (SEQ ID NO:28), actually appears to stimulate TGFβ1 activity in the tissue culture bio-assay at low concentrations. The basis of this mixed agonist/antagonist behavior has not been determined. The best inhibitor in this group, lib3-42 (SEQ ID NO:30) has an IC$_{50}$ of 22 nM and had no agonist behavior over the concentration ranges tested.

Group C ligands were tested as 2'-F derivatives and were not bio-active. Neither was the 2'-F orphan lib1-20-5 (SEQ ID NO:40). The 2'-NH$_2$, 40N orphan, lib3-45 is an example of another ligand with high affinity for TGFβ1 and no ability to inhibit TGFβ1 receptor binding.

Group D ligands were tested in the bio-assay as 2'-NH$_2$-UTP, 2'-F-CTP derivatives. Both lib2-6-1 (SEQ ID NO:35) and the truncated version lib2-6-1-81 (SEQ ID NO:36) can inhibit TGFβ1 receptor binding; however, a single mutation from a C to a G at position 53 decreases bio-activity in clone lib8–23. Similarly a 2 base pair deletion in clone lib6-30 (SEQ ID NO:34) at positions corresponding to nucleotides 67 and 68 in lib2-6-1 (SEQ ID NO:35) increases binding by 10 fold but eliminates bio-activity.

Lib2-6-1 (SEQ ID NO:35) was shown to be fully effective only against TGFβ1 and not TGFβ2 and TGFβ3. Lib2-6-1 (SEQ ID NO:35) was biologically active in the presence of 10% horse serum in the cell culture medium in addition to the 0.1% BSA. Thus the ligand demonstrates specificity towards TGFβ1 which is not interfered with by the presence of the horse serum in this assay. The biggest indication that the inhibition of TGFβ1 receptor binding is a specific phenomenon is the fact that not all TGFβ1 ligands block receptor binding, but the ones that do, do so reproducibly. There are no examples of ligands that do not bind to TGFβ1 blocking TGFβ1 receptor binding activity.

In summary, RNA ligands that can block TGFβ1 receptor binding are a subset of ligands. Binding is necessary but not sufficient for bio-activity. Roughly 50% of the high affinity ligands tested were inhibitors. Of the inhibitors, 30% were good inhibitors (IC$_{50}$<25 nM).

Example 4

Boundary Analysis

Truncation experiments were done on a number of TGFβ1 ligands to determine the nucleotides essential for binding. Group A ligands, lib3-13 (SEQ ID NO:12) and lib8-9 (SEQ ID NO:16), were truncated with consistent results. The fragment lib3-13-79 binds to TGFβ1, thus none of the nucleotides 3' to nucleotide 79 in lib3-13 are essential for binding. Similarly when all nucleotides 5' to nucleotide 38 are deleted the remaining fragment, lib3-13-(38-123) can still bind to TGFβ1. The 5' boundary is in agreement with the sequence lib6-23 (SEQ ID NO:21), which has a deletion corresponding to nucleotides 19-36 of lib3-13 (SEQ ID NO:25), and still binds to TGFβ1. Thus, all high affinity binding determinants for Group A clones may lie wholly within the random region and may correspond to a 42 nucleotide fragment, lib3-13-(38-79). Many Group A ligands contain deletions or substitutions within the predicted essential binding domain, in the region corresponding to lib3-13-(72-81). The deletion and substitution in lib4-32 have no effect on its 3' boundary which corresponds to lib3-13 nucleotide 80. Thus, the 3' boundary is probably correct and the alterations in nucleotide sequence 72–81 are ones that do not significantly alter the nucleic acid structure required for binding. Mutations in this region, most notably nucleotide 72 may, however, modify the ability of the ligand to block TGFβ1 receptor binding as noted earlier.

Boundary analysis of the 3' end of Group B ligand, lib4-12 (SEQ ID NO:28), predicts that nothing beyond nucleotide 72 is required for TGFβ1 binding. When the 5' boundary of lib4-12 was determined, all but the first three nucleotides were required for binding, indicating that the 5' constant region is an essential part of the ligand at least when the boundary of the full length ligand was determnined. Assuming that ligand lib3-44 (SEQ ID NO:29) has a similar binding determinant as lib4-12 (SEQ ID NO:28), we can also conclude that nucleotides 37-46 of lib4-12 are not required for binding since these are deleted in lib3-44 and lib3-42 (SEQ ID NO:30).

The 3' constant region is not necessary for binding in Group C and D ligands. Both ligand types bind without the 3' nucleotides in the constant region. Lib1-20-3-82, an 82 nucleotide truncated version of lib1-20-3 (SEQ ID NO:32), binds as well as the full length lib1-20-3. Likewise binding and bioactivity of lib2-6-1 is unaffected by the 3' truncation found in lib2-6-1-81 (SEQ ID NO:36).

Example 5

Experimental Procedures

In the preferred embodiment, a second set of SELEX experiments was performed in search of RNA and DNA ligands with specific high affinity for TGFβ1 from degenerate libraries containing 40 random positions (40N). This Example provides the general procedures followed and incorporated in Example 6.

A. Materials

M-MLV superscript reverse transcriptase was purchased from Gibco BRL (Gaithersburg, Md.). T7 RNA polymerase was purified according to standard procedures at NeXstar Pharmaceuticals, Inc. (Boulder, Colo.). Taq DNA polymerase (Amplitaq) was from Perkin Elmer/Cetus (Richmond, Calif.). T4 polynucleotide kinase, DNA polymerase (Klenow fragment), and alkaline phosphatase were purchased from New England Biolabs, Inc. (Beverly, Mass.). The 2'-amino substituted nucleotide triphosphates arnino-UTP and amino-CTP were synthesized according to standard procedures at NeXstar Pharmaceuticals, Inc. (Boulder, Colo.). Other reagents used in this work were of the highest quality obtainable.

B. Nucleic Acids

RNAs were synthesized by in vitro transcription using double-stranded DNA oligonucleotides and T7 RNA polymerase. DNA oligonucleotides (Table 5) were purchased from Operon, Inc. (Alameda, Calif.) and purified by 6% preparative polyacrylamide gel electrophoresis. PCR amplification was performed in 50 mM KCl, 10 mM Tris-HCl (pH 8.6), 2.5 mM $MgCl_2$, 170 mg/mL BSA, and dNTPs (present at 1 mM each). Taq DNA polymerase was used at 100 units per 0.1 mL reaction, and the 5'- and 3'-primers were present at 1 mM. Transcription was performed in 40 mM NaCl, 10 mM dithiothreitol, 50 mM Tris-acetate (pH 8.0), 8 mM magnesium acetate, 2 mM spermidine, and 2 mM NTP. T7 RNA polymerase was present at 1 unit/mL. The reaction was incubated at 28°C. for 16 hours and then treated with 20 units of DNAse I for an additional 10 min at 37°C. The reaction was stopped by the addition of one half volume of loading buffer (93% formamide, 10 mM EDTA, pH 8.0) and heated to 95°C. for 3 min prior to electrophoresis on a 6 % polyacrylamide/8 M urea denaturing gel. The RNA transcript was visualized by UV shadowing and was excised from the gel and eluted into TE buffer (10 mM Tris-acetate pH 8.0, 2 mM EDTA). The RNA transcript was ethanol precipitated, dried under vacuum, and redissolved in distilled $H_2O$. The concentration of RNA as well as single-stranded DNA was quantified by measuring the $A_{260}$ and assuming that 1 $A_{260}$ unit equaled 40 mg/mL and 33 mg/mL, respectively.

C. Evolution of High-Affinity Ligands

SELEX ligands that bind to TGFβ1 were derived essentially as described in U.S. Pat. No. 5,270,163 (see also Tuerk and Gold (1990) Science 249:505–510) using the oligonucleotides illustrated in Table 5 (SEQ ID NOS:43–54). The DNA templates contained a 40-nucleotide (40N) variable sequence generated by mixed-nucleotide DNA synthesis, as well as 5'- and 3'-fixed sequences, necessary for PCR amplification of the template. The 5'-fixed sequence of oligonucleotides 40N7 (SEQ ID NO:43) and 40N8 (SEQ ID NO:49) also contained a T7 RNA polymerase promoter. RNA for the first round of RNA SELEX was transcribed from double-stranded DNA templates generated by primer extension on single-stranded DNA templates 40N7 and 40N8 with the Klenow fragment of DNA polymerase I. RNA SELEX consisted of up to 15 rounds of RNA synthesis, binding to target, partitioning of bound and unbound RNA by nitrocellulose filtration, cDNA synthesis, and PCR amplification to regenerate the double-stranded DNA template. Binding to the target by the RNA pool was performed in binding buffer A (120 mM NaCl, 2.5 mM KCl, 0.12 mM $MgSO_4$, 40 mM HEPES, 20 mM $NaH_2PO_4/Na_2HPO_4$ pH 7.4, 0.01% HSA) at 37 degrees for at least 10 min prior to filtration. In contrast, the first round of single-stranded DNA SELEX was performed by using the synthetically synthesized oligonucleotides 40D7 and 40D8 directly. SELEX consisted of 25 rounds of binding to target, partitioning of bound and unbound single-stranded DNA by nitrocellulose filtration, PCR amplification to generate a double-stranded DNA population, and preparative polyacrylamide gel electrophoresis to purify single-stranded DNA for the next round of SELEX. Binding of the target to the single-stranded DNA pool was performed in binding buffer B (150 mM NaCl, 10 mM Tris-acetate pH 7.5, 0.001% BSA) at 37 degrees for at least 15 min prior to filtration. Radiolabeling of RNA as well as DNA repertoires was performed by incubation of 5 picomoles nucleic acid, 2 units of T4 polynucleotide kinase, and 6 mL $[\gamma^{32}P]$ ATP (800 Ci/mmol) in a volume of 10 mnL at 37 degrees for 30 min. The concentration of nucleic acid at each round of the SELEX experiment varied between 1500 nM and 1 nM while the concentration of the target TGF-β1 varied between 150 nM and 0.03 nM.

D. Cloning and Sequencing of Ligands

Cloning of the nucleic acid repertoire was performed as described by Tuerk and Gold (1990) Science 249:505–510 using double-stranded DNA that was generated from the RNA repertoire by PCR amplification. PCR-amplified DNA was digested with the restriction enzymes SphI and HindIII and ligated into compatible sites within pGEM. Ligated plasmids were transformed into *E. coli* and plated onto LB agar containing 5-bromo-4-chloro-3-indolyl β-D-galactoside, isopropyl thiogalactoside, and 100 mg/mL ampicillin. Colonies not expressing β-galactosidase were analyzed. Sequencing of DNA was performed as described by Tuerk and Gold (1990) using the dideoxynucleotide procedure of Sanger et al. (1977) *Proc. Natl. Acad. Sci. USA* 74:5463–5467. Plasmids were isolated from *E. coli* by the alkaline lysis miniprep procedure (Manitatis et al. (1982) in *Molecular Cloning: A laboratory Manual*, Cold Spring Harbor Laboratory Press, Cold Spring Harbor, N.Y.). DNA was incubated in 50 mM Tris-HCl (pH 8.3), 60 mM NaCl, 6 mM magnesium acetate, and 1 mM DTT with 0.4 mM dNTP and 0.2 mM dideoxy-NTP for 20 min at 48 degrees. DNA polymerase was present at 4 units per reaction. The reactions were stopped by the addition of 10 mL of loading buffer and heated to 95 degrees for 3 min prior to gel electrophoresis on a 6% polyacrylamine/8 M urea denaturing gel. G-track sequencing was performed as described and provided a convenient method to quickly screen the cloned library for ligands of different sequence. Briefly, the G-track sequencing reaction contained 50 mM Tris-HCl (pH 8.3), 60 mM NaCl, 6 mM magnesium acetate, and 1 mM DTT with 0.4 mM dNTP, 0.2 mM dideoxy-GTP, and 4 units of DNA polymerase. The reaction was performed at 48 degrees for 20 min and was stopped by the addition of 10 μL of loading buffer and heated to 95 degrees for 3 min prior to gel electrophoresis on a 6% polyacrylamide/8 M urea denaturing gel.

Example 6

Binding Analysis, Bioassay Results, and Sequences of A ssDNA Library

Binding analysis of the 40D7 DNA library for TGF-β1 is shown in FIG. 1. Binding data obtained from round 19 (triangles) and round 0 (circles) are shown. The experiment was performed by incubating nucleic acid (less than 1 nM)

and the indicated concentration of TGF-bl in Binding Buffer (150 mM NaCl, 10 mM Tris-acetate pH 8.2, 0.001% BSA) for 15 minutes at 37 degrees in a volume of 0.1 mL. Samples were filtered through nitrocellulose and were immediately followed by 3 mL of TE Buffer (10 mM Tris-acetate pH 8.0, 0.1 mM EDTA). The percentage of radiolabel bound was calculated from the amount of radiolabel retained on the nitrocellulose filter and the total radiolabel added to the binding reaction. The results show that the apparent Kd of the 40D7 library is 1nM, whereas the starting pool has an apparent Kd of 30 nM. Thus, the 40D7 library shows an increase of about three fold in binding.

Figure 2:
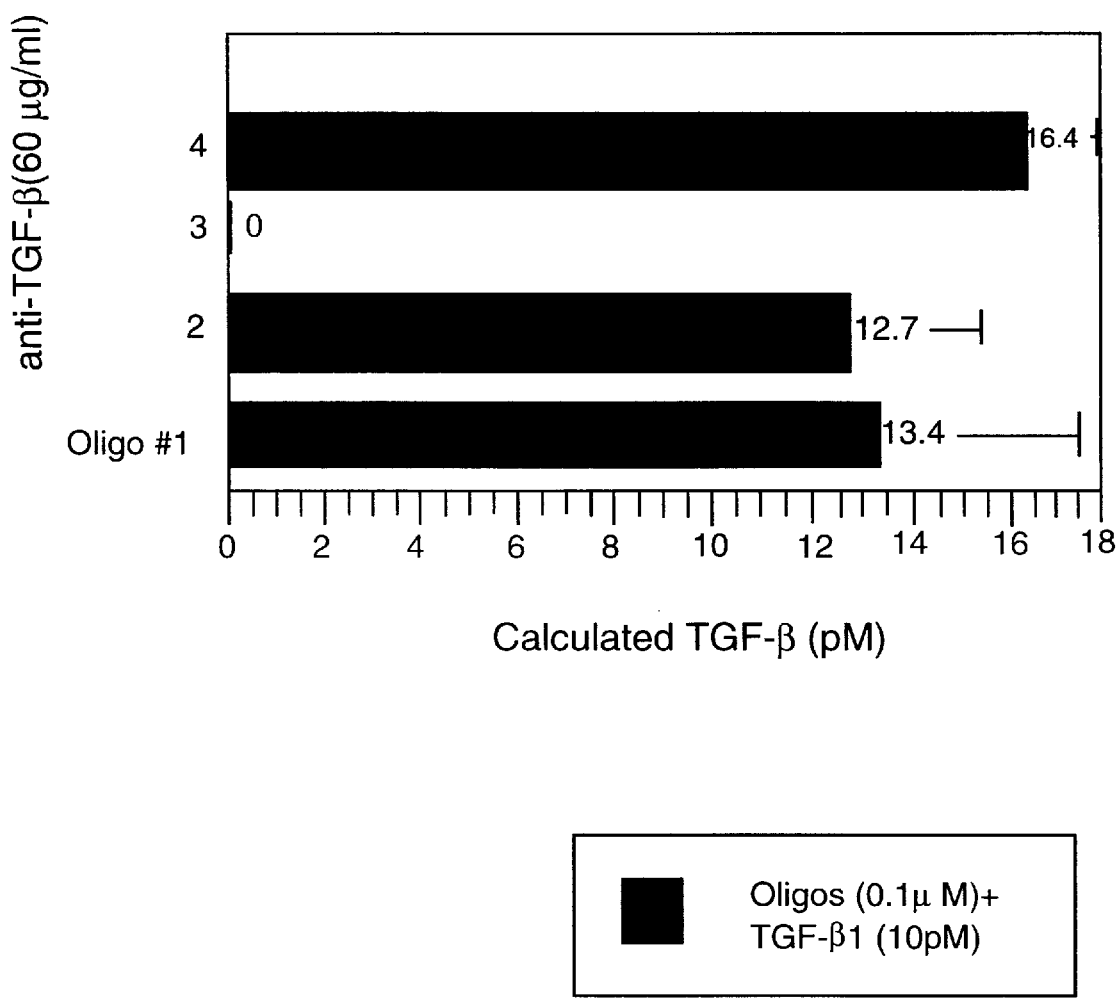
FIG. 2 shows the results of the PAI-luciferase assay of TGFβ1 (10 pM) incubated with oligonucleotides (0.1 µM) or anti-TGFβ (60 µg/ml).

A PAI-luciferase assay to detect TGF-$\beta$1 activity in the presence of the nucleic acid libraries generated in Example 5 was performed as described in Abe et al. (1994) *Analytical Biochem.* 216:276–284. Mink lung epithelial cells containing the PAI-luciferase reporter gene were incubated with TGF-$\beta$1 (10 pM) and oligonucleotides from the DNA libraries or anti TGF-$\beta$ antibody (60 $\mu$g/mL). The mink lung epithelial cells were incubated for 18 hours and oligonucleotides were pre-incubated with TGF-$\beta$1 before the assay and readded after 8 hours. Addition of oligonucleotides alone (100 nM) to the cell culture did not affect the assay (data not shown). The identity of the oligonucleotide libraries as well as their effect on luciferase activity is indicated in FIG. 2. The ssDNA library 40N7 completely inhibited the activity of TGF-$\beta$1, while the control (an equal concentration of randomized nucleic acid) showed a small stimulation of TGF-$\beta$1 activity.

Based on the results of the binding analysis and PAI-luciferase assay, DNA ligands from the 40N7 library were sequenced as described in Example 5. The sequences are shown in Table 6 (SEQ ID NOS:55–89). As the DNA 40N7 library showed inhibition in the PAI-luciferase bioassay, it is reasonable to suggest that the individual clones from the library are TGF$\beta$1 binders.

Example 7

Experimental Procedures

This Example provides the general procedures followed and incorporated in Examples 8–15 for the evolution of nucleic acid ligands to PDGF.

A. Materials

Recombinant human PDGF-AA (Mr=29,000), PDGF-AB (Mr=27,000) and PDGF-BB (Mr=25,000) were purchased from R&D Systems (Minneapolis, Minn.) in lyophilized form, free from carrier protein. All three isoforms were produced in *E. coli* from synthetic genes based on the sequences for the long form of the mature human PDGF A-chain (Betsholtz et al.,(1986) *Nature* 320: 695–699) and the naturally occurring mature form of human PDGF B-chain (Johnsson et al., (1984) *EMBO J.* 3: 921–928). Randomized DNA libraries, PCR. primers and DNA ligands and 5'-iodo-2'-deoxyuridine-substituted DNA ligands were synthesized by NeXstar Pharmaceuticals, Inc. (Boulder, Colo.) or by Operon Technologies (Alameda, Calif.) using the standard solid phase phosphoramidite method (Sinha et al., (1984) *Nucleic Acids Res.* 12: 4539–4557).

B. Single Stranded DNA (ssDNA) Selex

Essential features of the SELEX procedure have been described in detail in the SELEX Patent Applications (see also, Tuerk and Gold, *Science,* 249: 505 (1990); Jellinek et al., *Biochemistry,* 33: 10450 (1994); Jellinek et al., *Proc. Natl. Acad. Sci.,* 90: 11227 (1993)), which are incorporated by reference herein. The initial ssDNA library containing a contiguous randomized region of forty nucleotides, flanked by primer annealing regions (Table 7; SEQ ID NO:90) of invariant sequence, was synthesized by the solid phase phosphoramidite method using equal molar mixture of the four phosphoramidites to generate the randomized positions. The ssDNA library was purified by electrophoresis on an 8% polyacrylamide/7 M urea gel. The band that corresponds to the full-length DNA was visualized under UV light, excised from the gel, eluted by the crush and soak method, ethanol precipitated and pelleted by centrifugation. The pellet was dried under vacuum and resuspended in phosphate buffered saline supplemented with 1 mM $MgCl_2$ (PBSM=10.1 mM $Na_2HPO_4$, 1.8 mM $KH_2PO_4$, 137 mM NaCl and 2.7 mM KCl, 1 mM $MgCl_2$, pH 7.4) buffer. Prior to incubation with the protein, the ssDNA was heated at 90° C. for 2 minutes in PBSM and cooled on ice. The first selection was initiated by incubating approximately 500 pmol ($3 \times 10^{14}$ molecules) of 5' $^{32}$P end-labeled random ssDNA with PDGF-AB in binding buffer (PBSM containing 0.01% human serum albumin (HSA)). The mixture was incubated at 4° C. overnight, followed by a brief (15 min) incubation at 37° C. The DNA bound to PDGF-AB was separated from unbound DNA by electrophoresis on an 8% polyacrylamide gel (1:30 bis-acrylamide:acrylamide) at 4° C. and at 5 V/cm with 89 mM Tris-borate (pH 8.3) containing 2 mM EDTA as the running buffer. The band that corresponds to the PDGF-ssDNA complex, which runs with about half the electrophoretic mobility of the free ssDNA, was visualized by autoradiography, excised from the gel and eluted by the crush and soak method. In subsequent affinity selections, the ssDNA was incubated with PDGF-AB for 15 minutes at 37° C. in binding buffer and the PDGF-bound ssDNA was separated from the unbound DNA by nitrocellulose filtration, as previously described (Green,et al., (1995) *Chemistry and Biology* 2, 683–695). All affinity-selected ssDNA pools were amplified by PCR in which the DNA was subjected to 12–20 rounds of thermal cycling (30 s at 93° C., 10 s at 52° C., 60 s at 72° C.) in 10 mM Tris-Cl (pH 8.4) containing 50 mM KCl, 7.5 mM $MgCl_2$, 0.05 mg/ml bovine serum albumin, 1 mM deoxynucleoside triphosphates, 5 $\mu$M primers (Table 7) and 0.1 units/$\mu$l Taq polymerase. The 5' PCR primer was 5' end-labeled with polynucleotide kinase and [$\gamma$-$^{32}$P]ATP and the 3' PCR primer was biotinylated at the 5' end using biotin phosphoramidite (Glen Research, Sterling, Va.). Following PCR amplification, streptavidin (Pierce, Rockford, Ill.) was added to the unpurified PCR reaction mixture at a 10-fold molar excess over the biotinylated primer and incubated for 15 min at room temperature. The dsDNA was denatured by adding an equal volume of stop solution (90% formamide, 1% sodium dodecyl sulfate, 0.025% bromophenol blue and xylene cyanol) and incubating for 20 min at room temperature. The radiolabeled strand was separated from the streptavidin-bound biotinylated strand by electrophoresis on 12% polyacrylamide/7M urea gels. The faster migrating radiolabeled (non-biotinylated) ssDNA strand was cut out of the gel and recovered as described above. The amount of ssDNA was estimated from the absorbance at 260 mn using the extinction coefficient of 33 $\mu$g/ml/absorbance unit (Sambrook et al., (1989) *Molecular Cloning: A Laboratory Manual,* 2 Ed. 3 vols., Cold Spring Harbor Laboratory Press, Cold Spring Harbor).

C. Cloning and Sequencing

The amplified affinity-enriched pool from SELEX round 12 was purified on a 12% polyacrylamide gel and cloned between HindIII and PstI sites in JM109 strain of *E. coli* (Sambrook, et al., (1989) *Molecular Cloning: A Laboratory*

*Manual*, 2 Ed. 3 vols., Cold Spring Harbor Laboratory Press, Cold Spring Harbor). Individual clones were used to prepare plasmids by alkaline lysis. Plasmids were sequenced at the insert region using the forward sequencing primer and Sequenase 2.0 (Amersham, Arlington Heights, Ill.) according to the manufacturer's protocol.

D. Determination of the Apparent Equilibrium Dissociation Constants and the Dissociation Rate Constants The binding of ssDNA ligands at low concentrations to varying concentrations of PDGF was determined by the nitrocellulose filter binding method as described (Green et al., (1995) *Chemistry and Biology* 2: 683–695). The concentrations of PDGF stock solutions (in PBS) were determined from the absorbance readings at 280 mn using the following $e_{280}$ values calculated from the amino acid sequences (Gill, S. C., and von Hippel, P. H. (1989) *Anal. Biochem.* 182: 319–326): 19,500 $M^{-1}cm^{-1}$ for PDGF-AA, 15,700 $M^{-1}cm^{-1}$ for PDGF-AB and 11,800 $M^{-1}cm^{-1}$ for PDGF-BB. ssDNA for all binding experiments were purified by electrophoresis on 8% (>80 nucleotides) or 12% (<40 nucleotides) polyacrylamide/7 M urea gels. All ssDNA ligands were heated at 90° C. in binding buffer at high dilution ($\approx$1 nM) for 2 min and cooled on ice prior to frier dilution into the protein solution. The binding mixtures were typically incubated for 15 min at 37° C. before partitioning on nitrocellulose filters.

The binding of DNA ligands (L) to PDGF-AA (P) is adequately described with the bimolecular binding model for which the fraction of bound DNA at equilibrium (q) is given by eq. 1, $$q=(f/2[L]_t\{[P]_t+[L]_t+K_d-[([P]_t+[L]_t+K_d)^2-4[P]_t[L]_t]^{1/2}\} \quad (1)$$

where $[P]_t$ and $[R]_t$ are total protein and total DNA concentrations, $K_d$ is the equilibrium dissociation constant and f is the efficiency of retention of protein-DNA complexes on nitrocellulose filters (Irvine et al., (1991) *J. Mol. Biol.* 222: 739–761; Jellinek et al., (1993) *Proc. Nat'l. Acad. Sci. USA* 90: 11227–11231).

The binding of DNA ligands to PDGF-AB and PDGF-BB is biphasic and can be described by a model in which the DNA ligand is composed of two non-interconverting components ($L_1$ and $L_2$) that bind to the protein with different affinities, described by corresponding dissociation constants, $K_{d1}$ and $K_{d2}$ (Jellinek et al., 1993) *Proc. Nat'l. Acad. Sci. USA* 90: 11227–1123 1). In this case, the explicit solution for the fraction of bound DNA (q) is given by eq. 2, $$q = f\left(\frac{\chi_1 K_{d1}}{1+K_{d1}[P]} + \frac{\chi_2 K_{d2}}{1+K_{d2}[P]}\right)[P] \quad (2)$$

with $$[P] = \frac{[P]t}{1+\frac{\chi_1 K_{d1}[L]_t}{1+K_{d1}[P]} + \frac{\chi_2 K_{d2}[L]_t}{1+K_{d2}[P]}}$$

where $\chi_1$ and $\chi_2(=1-\chi_1)$ are the mole fractions of $L_1$ and $L_2$. The $K_d$ values for the binding of DNA ligands to PDGF were calculated by fitting the data points to eq. 1 (for PDGF-AA) or eq. 2 (for PDGF-AB and PDGF-BB) using the non-linear least squares method.

The dissociation rate constants ($k_{off}$) were determined by measuring the amount of $^{32}$P 5'-end labeled minimal ligands (0.17 nNM) bound to PDGF-AB (1 nM) as a function of time following the addition of 500-fold excess of unlabeled ligands, using nitrocellulose filter binding as the partitioning method. The $k_{off}$ values were determined by fitting the data points to the first-order rate equation (eq. 3)

$$(q-q_\infty)/(q_o-q_\infty)=\exp(-k_{off}t) \quad (3)$$

where q, $q_0$ and $q_\infty$ represent the fractions of DNA bound to PDGF-AB at any time (t), t=0 and t=$\infty$, respectively.

E. Minimal Ligand Determinations

To generate a population of 5' end-labeled DNA ligands serially truncated from the 3' end, a primer complementary to the 3' invariant sequence region of a DNA ligand template (truncated primer 5N2, Table 7; SEQ ID NO:92) was radiolabeled at the 5' end with [$\gamma$-$^{32}$P]-ATP and T4 polynucleotide kinase, annealed to the template and extended with Sequenase (Amersham, Arlington Heights, Ill.) and a mixture of all four dNTPs and ddNTPs. Following incubation in binding buffer for 15 min at 37° C., the fragments from this population that retain high affinity binding to PDGF-AB were separated from those with weaker affinity by nitrocellulose filter partitioning. Electrophoretic resolution of the fragments on 8% polyacrylamide/7 M urea gels, before and after affinity selection, allows determination of the 3' boundary. To generate a population of 3' end-labeled DNA ligands serially truncated from the 5' end, the DNA ligands were radiolabeled at the 3' end with [$\alpha$-$^{32}$P]-cordycepin-5'-triphosphate (New England Nuclear, Boston, Mass.) and T-NA ligase (Promega, Madison, Wis.), phosphorylated at the 5' end with ATP and T4 polynucleotide kinase, and partially digested with lambda exonuclease (Gibco BRL, Gaithersburg, Md.). Partial digestion of 10 pmols of 3'-labeled ligand was done in 100 uL volume with 7 mM glycine-KOH (pH 9.4), 2.5mM MgCl$_2$, 1 $\mu$g/ml BSA, 15 $\mu$g tRNA, and 4 units of lambda exonuclease for 15 min at 37°. The 5' boundary was determined in an analogous manner to that described for the 3' boundary.

F. Melting Temperature ($T_m$) Measurements

Melting profiles for the minimal DNA ligands were obtained on a Cary Model 1E spectrophotometer. Oligonucleotides (320–400 nM) were heated to 95° C. in PBS, PBSM or PBS with 1 mM EDTA and cooled to room temperature prior to the melting profile determination. Melting profiles were generated by heating the samples at the rate of 1° C./min from 15–95° C. and recording the absorbance every 0.1 ° C. The first derivative of the data points was calculated using the plotting program KaleidaGraph (Synergy Software, Reading, Pa.). The first derivative values were smoothed using a 55 point smoothing function by averaging each point with 27 data points on each side. The peak of the smoothed first derivative curves was used to estimate the $T_m$ values.

G. Crosslinking of 5-iodo-2'-deoxyuridine-Substituted DNA Ligands to PDGF-AB.

DNA ligands containing single or multiple substitutions of 5'-iodo-2'deoxyuridine for thymidine were synthesized using the solid phase phosphoramidite method. To test for the ability to crosslink, trace amounts of 5'$^{32}$P end-labeled ligands were incubated with PDGF-AB (100 nM) in binding buffer at 37° for 15 min prior to irradiation. The binding mixture was transferred to a 1 cm path length cuvette thermostated at 37° and irradiated at 308 nm for 25–400 s at 20 Hz using a XeCl charged Lumonics Model EX748 excimer laser. The cuvette was positioned 24 cm beyond the focal point of a convergent lens, with the energy at the focal point measuring 175 mjoules/pulse. Following irradiation, aliquots were mixed with an equal volume of formamide loading buffer containing 0.1 % SDS and incubated at 95° for 5 min prior to resolution of the crosslinked PDGF/ligand complex from the free ligand on 8% polyacrylamide/7 M urea gels.

To identify the protein site of crosslinking for ligand 20t-I4, binding and irradiation were done on a larger scale.

PDGF-AB and 5' $^{32}$P end-labeled ligand, each at 1 μM in PBSM, were incubated and irradiated (300 s) as described above in two 1 ml reaction vessels. The reaction mixtures were combined, ethanol precipitated and resuspended in 0.3 ml of Tris-HCl buffer (200 mM, pH 8.5). The PDGF-AB/ ligand crosslinked complex was digested with 0.17 μg/μl of modified trypsin (Boehringer Mannheim) for 20 hours at 37°. The digest mixture was extracted with phenol/chloroform, chloroform and then ethanol precipitated. The pellet was resuspended in water and an equal volume of formamide loading buffer with 5% (v/v) β-mercaptoethanol (no SDS), incubated at 95° for 5 min, and resolved on a 40 cm 8% polyacrylamide/7 M urea gel. The crosslinked tryptic-peptide/ligand that migrated as two closely spaced bands about 1.5 cm above the free ligand band was excised from the gel and eluted by the crush and soak method and ethanol precipitated. The dried crosslinked peptide (about 160 pmoles based on the specific activity) was sequenced by Edman degradation (Midwest Analytical, Inc., St. Louis, Mo.).

H. Receptor Binding Assay

The binding of $^{125}$I-PDGF-AA and $^{125}$I-PDGF-BB to porcine aortic endothelial (PAE) cells transfected with PDGF α- or β-receptors were performed as described (Heldin et al., (1988) *EMBO J.* 7, 1387–1394). Different concentrations of DNA ligands were added to the cell culture (1.5 cm$^2$) in 0.2 ml of phosphate buffered saline supplemented with 1 mg bovine serum albumin per ml together with $^{125}$I-PDGF-AA (2 ng, 100,000 cpm) or $^{125}$1I-PDGF-BB (2 ng, 100,000 cpm). After incubation at 4° C. for 90 min, the cell cultures were washed and cell associated radioactivity determined in a γ-counter (Heldin et al., (1988) *EMBO J.* 7, 1387–1394).

I. [$^3$H]thymidine Incorporation Assay

The incorporation of [$^3$H]thymidine into PAE cells expressing PDGF β-receptor in response to 20 ng/ml of PDGF-BB or 10% fetal calf serum and in the presence of different concentrations of DNA ligands was performed as described (Mori et al., (1991) *J. Biol. Chem.* 266, 21158–21164). After incubation for 24 h at 37° C., $^3$H-radioactivity incorporated into DNA was determined using a β-counter.

Example 8 ssDNA Ligands of PDGE

High affinity DNA ligands to PDGF AB were identified by the SELEX process from a library of ≈3×10$^{14}$ molecules (500 pmol) of single stranded DNA randomized at forty contiguous positions (Table 7; SEQ ID NO:90). The PDGF-bound DNA was separated from unbound DNA by polyacrylamide gel electrophoresis in the first round and by nitrocellulose filter binding in the subsequent rounds. After 12 rounds of SELEX, the affinity-enriched pool bound to PDGF-AB with an apparent dissociation constant ($K_d$) of ≈50 pM (data not shown). This represented an improvement in affinity of ≈700-fold compared to the initial randomized DNA library. This affinity-enriched pool was used to generate a cloning library from which 39 isolates were sequenced. Thirty-two of these ligands were found to have unique sequences (Table 8; SEQ ID NOS:93–124). Ligands that were subjected to the minimal sequence determination are marked with an asterisk (*) next to the clone number. The clone numbers that were found to retain high affinity binding as minimal ligands are italicized. All ligands shown in Table 8 were screened for their ability to bind to PDGF AB using the nitrocellulose filter binding method. To identify the best ligands from this group, we determined their relative affinities for PDGF-AB by measuring the fraction of 5' $^{32}$P end-labeled ligands bound to PDGF-AB over a range of protein concentrations. For the ligands that bound to PDGF-AB with high affinity, the affinity toward PDGF-BB and PDGF-AA was also examined: in all cases, the affinity of ligands for PDGF-AB and PDGF-BB was comparable while the affinity for PDGF-AA was considerably lower (data not shown).

Twenty-one of the thirty-two unique ligands can be grouped into a sequence family shown in Table 9. The sequences of the initially randomized region (uppercase letters) are aligned according to the consensus three-way helix junction motif. Nucleotides in the sequence-invariant region (lowercase letters) are only shown where they participate in the predicted secondary structure. Several ligands were "disconnected" (equality symbol) in order to show their relatedness to the consensus motif through circular permutation. The nucleotides predicted to participate in base pairing are indicated with underline inverted arrows, with the arrow heads pointing toward the helix junction. The sequences are divided into two groups, A and B, based on the first single stranded nucleotide (from the 5' end) at the helix junction (A or G, between helices II and III). Mismatches in the helical regions are shown with dots under the corresponding letters (G-T and T-G base pairs were allowed). In places where single nucleotide bulges occur, the mismatched nucleotide is shown above the rest of the sequence between its neighbors.

Figure 3:
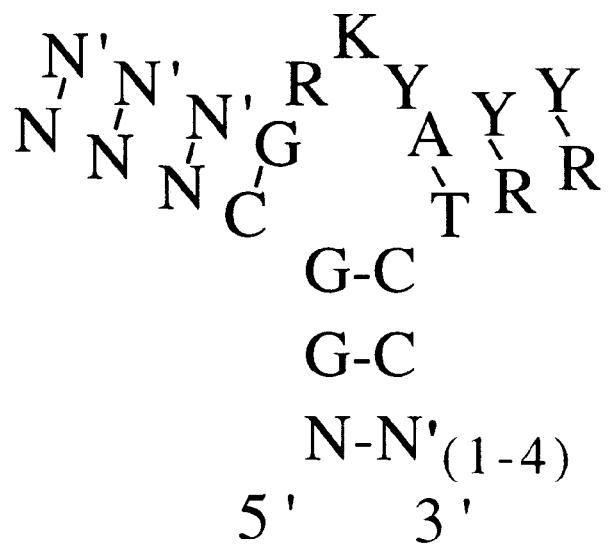
FIG. 3 shows the consensus secondary structure for the sequence set shown in Table 9. R=A or G, Y=C or T, K=G or T, N and N' indicate any base pair.

This classification is based in part on sequence homology among these ligands, but in greater part on the basis of a shared secondary structure motif: a three-way helix junction with a three nucleotide loop at the branch point (FIG. 3). These ligands were subdivided into two groups; for ligands in group A, the loop at the branch point has an invariant sequence AGC and in group B, that sequence is G(T/G)(C/T). The proposed consensus secondary structure motif is supported by base-pairing covariation at non-conserved nucleotides in the helices (Table 10). Since the three-way junctions are encoded in continuous DNA strands, two of the helices end in loops at the distal end from the junction. These loops are highly variable, both in length. and in sequence. Furthermore, through circular permutation of the consensus motif, the loops occur in all three helices, although they are most frequent in helices II and III. Together these observations suggest that the regions distal from the helix junction are not important for high affity binding to PDGF-AB. The highly conserved nucleotides are indeed found near the helix junction (Table 9, FIG. 3).

Example 9

Boundary Analysis

The minimal sequence necessary for high affinity binding was determined for the six best ligands to PDGF-AB. In general, the information about the 3' and 5' minimal sequence boundaries can be obtained by partially fragmenting the nucleic acid ligand and then selecting for the fragments that retain high affinity for the target. With RNA ligands, the fragments can be conveniently generated by mild alkaline hydrolysis (Tuerk et al., (1990) *J. Mol. Biol.* 213: 749–761; Jellinek et al., (1994) *Biochemistry* 33: 10450–10456; Jellinek et al., (1995) *Biochemistry* 34: 11363–11372; Green et al., (1995) *J. Mol. Biol.* 247: 60–68). Since DNA is more resistant to base, an alternative method of generating fragments is needed for DNA. To determine the 3' boundary, a population of ligand fragments serially truncated at the 3' end was generated by extending the 5' end-labeled primer annealed to the 3' invariant sequence of a DNA ligand using the dideoxy sequencing method. This population was affinity-selected by nitrocellulose filtration and the shortest fragments (truncated from the 3' end) that retain high affinity binding for PDGF-AB were identified by polyacrylamide gel electrophoresis. The 5' boundary was determined in an analogous manner except that a population of 3' end-labeled ligand fragments serially truncated at the 5' end was generated by limited digestion with lambda exonuclease. The minimal ligand is then defined as the sequence between the two boundaries. It is important to keep in mind that, while the information derived from these experiments is useful, the suggested boundaries are by no means absolute since the boundaries are examined one terminus at a time. The untruncated (radiolabeled) termini can augment, reduce or have no effect on binding (Jellinek et a., (1994) *Biochemistry* 33: 10450–10456).

Of the six minimal ligands for which the boundaries were determined experimentally, two (20t (SEQ ID NO:172) and 41t (SEQ ID NO:174); truncated versions of ligands 20 and 41) bound with affinities comparable (within a factor of 2) to their full-length analogs and four had considerably lower affinities. The two minimal ligands that retained high affinity binding to PDGF, 20t and 41t, contain the predicted three-way helix junction secondary structure motif (FIG. 4). The sequence of the third minimal ligand that binds to PDGF-AB with high affinity, 36t (SEQ ID NO: 173), was deduced from the knowledge of the consensus motif (FIG. 4). In subsequent experiments, we found that the single-stranded region at the 5' end of ligand 20t is not important for high affinity binding. Furthermore, the trinucleotide loops on helices II and III in ligand 36t (GCA and CCA) can be replaced with pentaethylene glycol spacers (infra). These experiments provide further support for the importance of the helix junction region in high affinity binding to PDGF-AB.

Figure 5A:
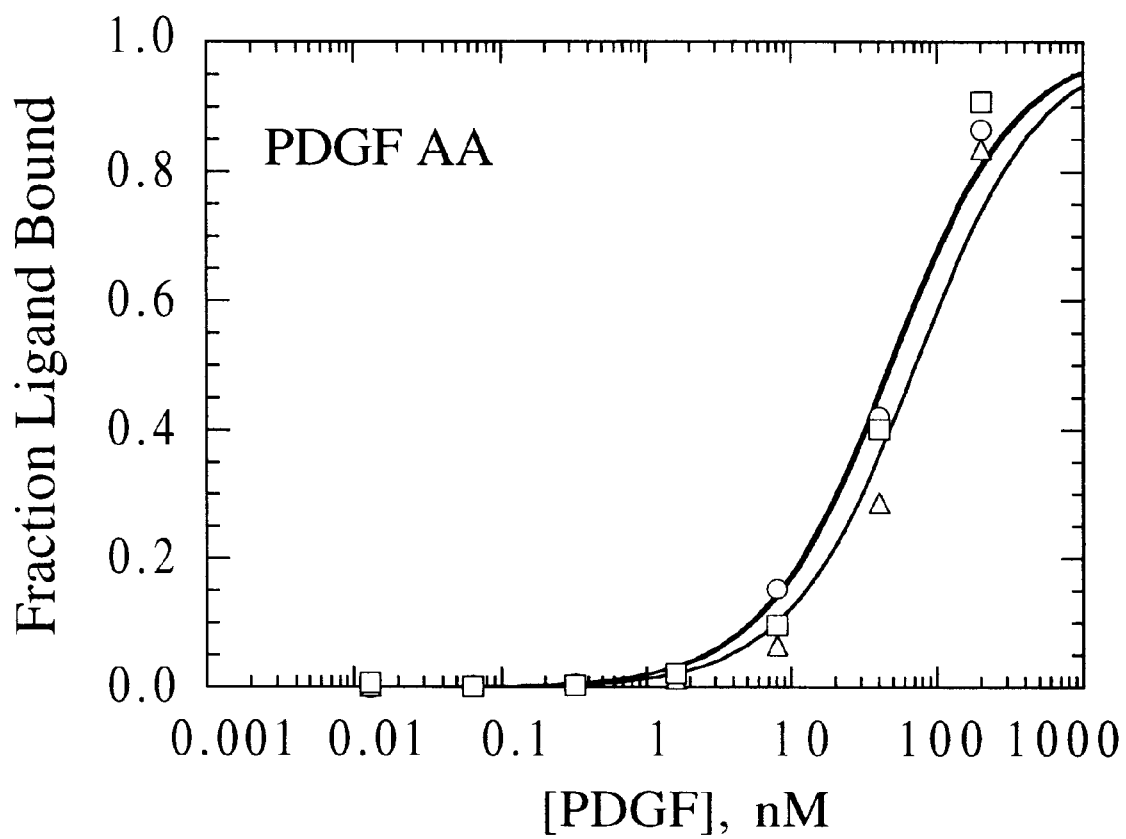
FIGS. 5A, 5B and 5C show the binding of minimal high affinity DNA ligands to PDGF-AA, AB and BB, respectively. The fraction of $^{32}P$ 5' end-labeled DNA ligands bound to varying concentrations of PDGF was determined by the nitrocellulose filter binding method. Minimal ligands tested were 20t (○), 36t (Δ), and 41t (□). Oligonucleotide concentrations in these experiments were ≈10 pM (PDGF-AB and PDGF-BB) and ≈50 pM (PDGF AA). Data points were fitted to eq. 1 (for binding of the DNA ligands to PDGF-AA) or to eq. 2 (for binding to PDGF AB and BB) using the non-linear least squares method. Binding reactions were done at 37° C. in binding buffer (PBSM with 0.01% HSA).
Figure 5B:
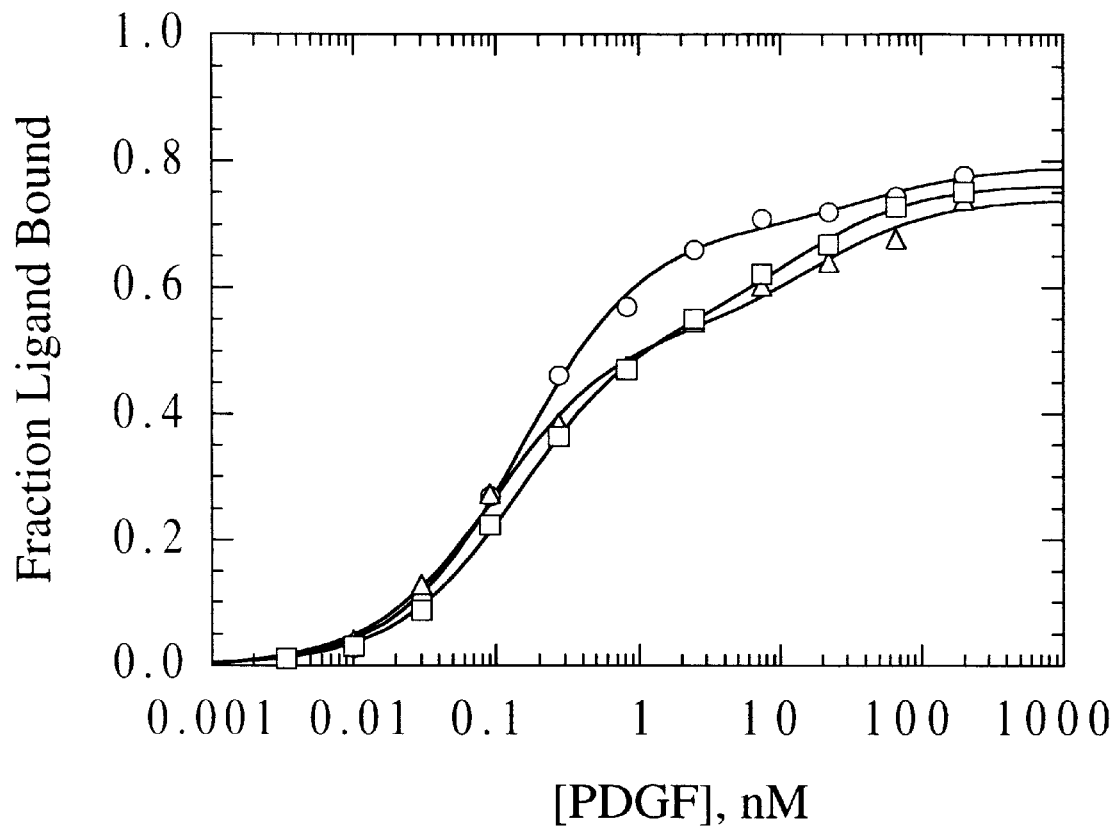
Figure 5C:
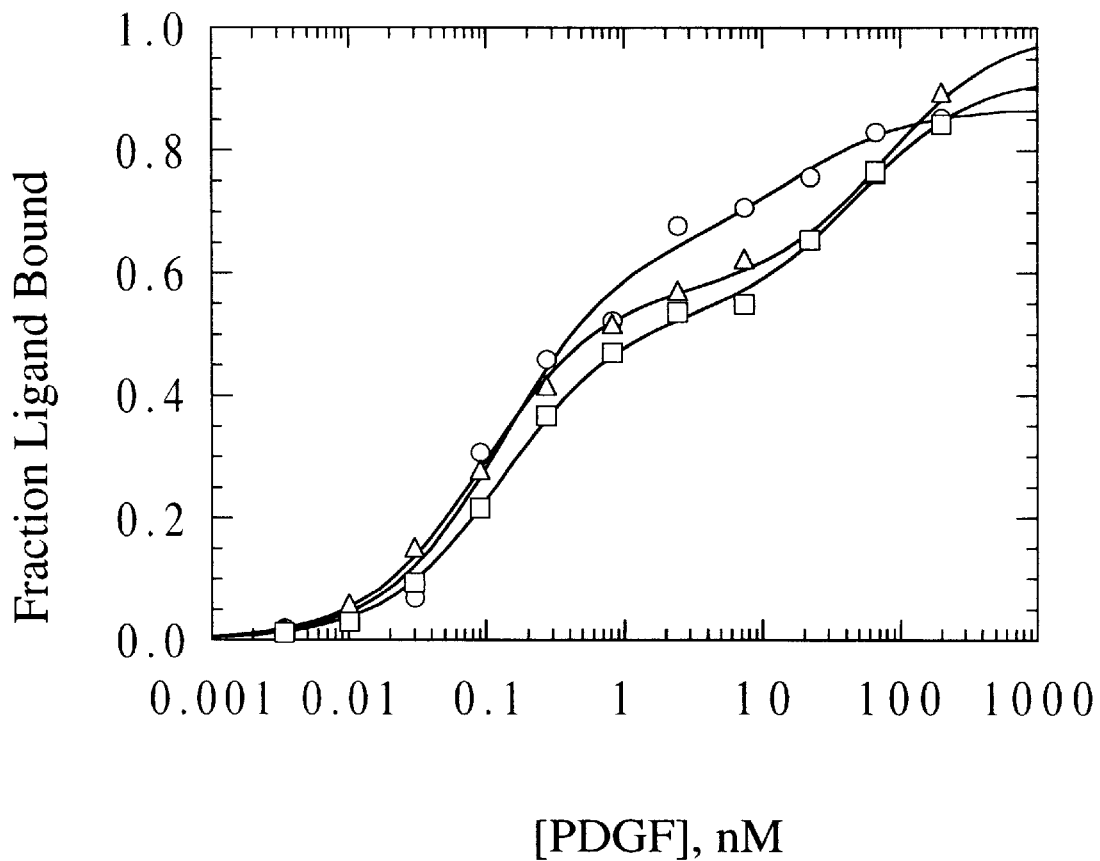

The binding of minimal ligands 20t, 36t, and 41t to varying concentrations of PDGF-AA, PDGF-AB and PDGF-BB is shown in FIGS. 5A, 5B and 5C. In agreement with the binding properties of their full length analogs, the minimal ligands bind to PDGF-AB and PDGF-BB with substantially higher affinity than to PDGF AA (FIGS. 5A, 5B, and 5C, Table 11). In fact, their affinity for PDGF-AA is comparable to that of random DNA (data not shown). The binding to PDGF-AA is adequately described with a monophasic binding equation while the binding to PDGF-AB and PDGF-BB is notably biphasic. In previous SELEX experiments, biphasic binding has been found to be a consequence of the existence of separable nucleic acid species that bind to their target protein with different affmiities (Jellinek et al., (1995) *Biochemistry* 34: 11363–11372) and unpublished results). The identity of the high and the low affinity fractions is at present not known. Since these DNA ligands described here were synthesized chemically, it is possible that the fraction that binds to PDGF-AB and PDGF-BB with lower affinity represents chemically imperfect DNA. Alternatively, the high and the low affinity species may represent stable conforrnnational isomers that bind to the PDGF B-chain with different affinities. In any event, the higher affinity binding component is the most populated ligand species in all cases (FIGS. 5B and 5C).

For comparison, a 39-mer DNA ligand that binds to human thrombin with a $K_d$ of 0.5 nM (ligand T39 (SEQ ID NO.:177): 5'-CAGTCCGTGGTAGGGCAGGTTGGG-GTGACTTCGTGGAA[3'T], where [3'T] represents a 3'—3' linked thymidine nucleotide added to reduce 3'-exonuclease degradation) and has a predicted stem-loop structure, binds to PDGF-AB with a $K_d$ of 0.23 µM (data not shown).

Example 10

Kinetic Stability of PDGE-Nucleic Acid Ligand Complexes

Figure 6:
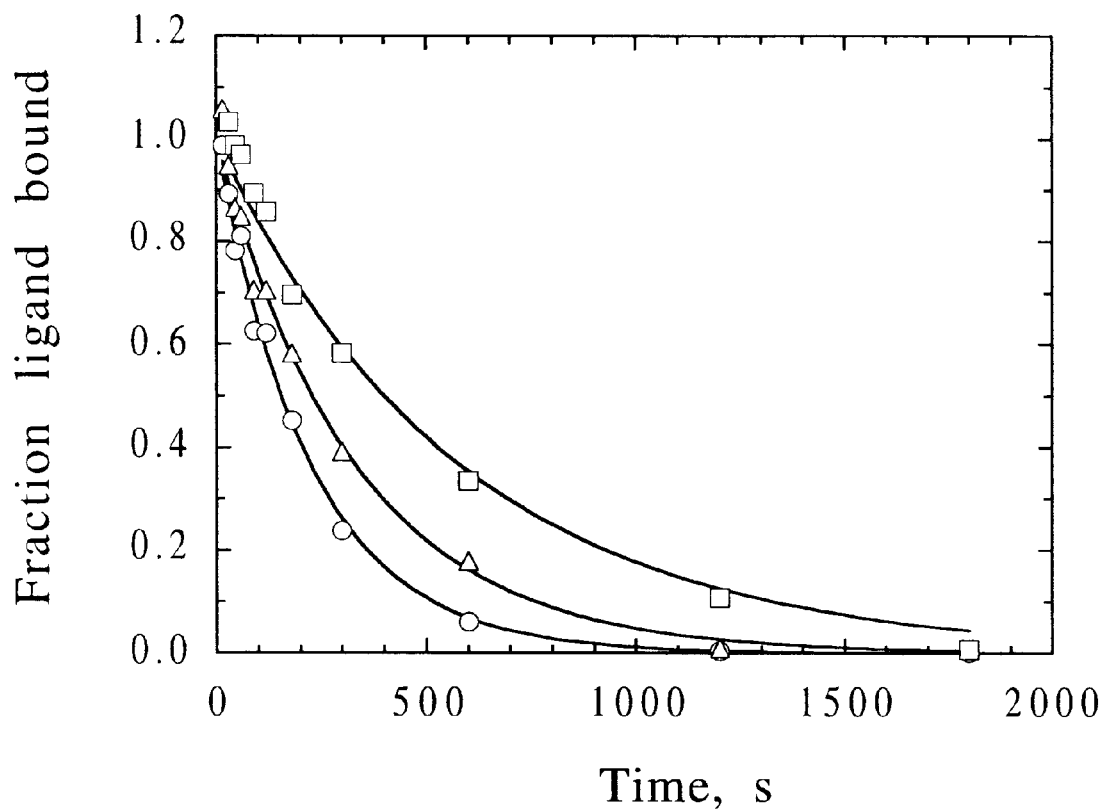
FIG. 6 shows the dissociation rate determination for the high affinity interaction between the minimal DNA ligands and PDGF AB. The fraction of 5' $^{32}$P end-labeled ligands 20t (○), 36t (Δ), and 41t (□), all at 0.17 nM, bound to PDGF AB (1 nM) was measured by nitrocellulose filter binding at the indicated time points following the addition of a 500-fold excess of the unlabeled competitor. The dissociation rate constant ($k_{off}$) values were determined by fitting the data points to eq 3. The experiments were performed at 37° C. in binding buffer.

In order to evaluate the kinetic stability of the PDGF-AB/DNA complexes, the dissociation rates were determined at 37° C. for the complexes of minimal ligands 20t, 36t and 41t (SEQ ID NOS:172–174) with PDGF-AB by measuring the amount of radiolabeled ligands (0.17 nM) bound to PDGF-AB (1 nM) as a function of time following the addition of a large excess of unlabeled ligands (FIG. 6). At these protein and DNA ligand concentrations, only the high affinity fraction of the DNA ligands binds to PDGF-AB. The following values for the dissociation rate constants were obtained by fitting the data points shown in FIG. 6 to the first-order rate equation: $4.5\pm0.2\times10^{-3}$ s$^{-1}$ ($t_{1/2}$=2.6 min) for ligand 20t, $3.0\pm0.2\times10^{-3}$ s$^{-1}$ ($t_{1/2}$=3.8 min) for ligand 36t, and $1.7\pm0.1\times10^{-3}$ s$^{-1}$ ($t_{1/2}$=6.7 min) for ligand 41t. The association rates calculated for the dissociation constants and dissociation rate constants ($k_{on}=k_{off}/K_d$) are $3.1\times10^7$ M$^{-1}$s$^{-1}$ for 20t, $3.1\times10^7$ M$^{-1}$s$^{-1}$ for 36t and $1.2\times10^7$ M$^{-1}$s$^{-1}$ for 41t.

Example 11

Thermal Melting Properties

In order to examine the ability of minimal ligands 20t, 36t and 41t to assume folded structures, their melting temperatures ($T_m$'s) were determined from the UV absorbance vs. temperature profiles in PBSM or PBSE buffers. At the oligonucleotide concentrations used in these experiments (320–440 nM), only the monomeric species were observed as single bands on non-denaturing polyacrylamide gels (data not shown). Ligands 20t and 41t underwent thermal melting that is well described by a two-state (folded and unfolded) model with linearly sloping baselines (Petersheim and Turner (1983) *Biochem.* 22:256–263) with $T_m$ values in PBSM buffer of 43.8±0.4° C. and 49.2±0.5° C., respectively. In PBSE buffer, similar $T_m$ values were obtained: 44.8±0.5° C. for ligand 20t and 48.0±0.5° C. for ligand 41t. Ligand 36t exhibited a more complex thermal melting profile in which two distinct transitions were observed. In this case, the data were well described by a three-state model in which the fully folded and the unfolded states are connected through a partially unfolded intermediate results. Using this model, we obtained two $T_m$ values for ligand 36t: 47.0±0.9° C. and 67.1±3.8° C. in PBSM buffer and 44.2±1.7° C. and 64.3±4.1° C. in PBSE buffer.

Example 12

Photo-Crosslinking of Nucleic Acid Ligands and PDGE

In order to determine the sites on the DNA ligands and PDGF that are in close contact, a series of photo-crosslinking experiments were performed with 5'-iodo-2'-deoxyuridine (IdU)-substituted DNA ligands 20t, 36t and 41t (SEQ ID NOS:172–174). Upon monochromatic excitation at 308 nm, 5-iodo- and 5-bromo-substituted pyrimidine nucleotides populate a reactive triplet state following inter-system crossing from the initial n to π* transition. The excited triplet state species then reacts with electron rich amino acid residues (such as Trp, Tyr and His) that are in its close proximity to yield a covalent crosslink. This method has been used extensively in studies of nucleic acid-protein interactions since it allows irradiation with >300 mn light which minimizes photodamage (Willis et al., (1994) *Nucleic*

Acids Res. 22: 4947–4952; Stump, W. T., and Hall, K. B. (1995) RNA 1: 55–63; Willis et al., (1993) Science 262: 1255–1257; Jensen et al., (1995) Proc. Natl. Acad. Sci., U. S. A. 92: 12220–12224). Analogs of ligands 20t, 36t and 41t were synthesized in which all thymidine residues were replaced with IdU residues using the solid phase phosphoramidite method. The affinity of these IdU-substituted ligands for PDGF-AB was somewhat enhanced compared to the unsubstituted ligands and based on the appearance of bands with slower electrophoretic mobility on 8% polyacrilamide/7 M urea gels, all three 5' end-labeled IdU-substituted ligands crosslinked to PDGF-AB upon irradiation at 308 nm (data not shown). The highest crosslinking efficiency was observed with IdU-substituted ligand 20t. To identify the specific IdU position(s) responsible for the observed crosslinking, seven singly or multiply IdU-substituted analogs of 20t were tested for their ability to photo-crosslink to PDGF-AB: ligands 20t–I1 through 20t–17 (5'-TGGGAGGGCGCGT$^1$T$^1$CT$^1$T$^1$CGT$^2$GGT$^3$T$^4$-ACT$^5$T$^6$T$^6$T$^6$AGT$^7$CCCG-3' (SEQ ID NOS:178–184) where the numbers indicate IdU substitutions at indicated thymidine nucleotides for the seven ligands). Of these seven ligands, efficient crosslinking to PDGF-AB was observed only with ligand 20t–I4. The photo-reactive IdU position corresponds to the 3' proximal thymidine in the loop at the helix junction (FIG. 4).

To identify the crosslinked amino acid residue(s) on PDGF-AB, a mixture of 5' end-labeled 20t–I4 and PDGF-AB was incubated for 15 min at 37° C. followed by irradiation at 308 nm. The reaction mixture was then digested with modified trypsin and the crosslinked fragments resolved on an 8% polyacrylamide/7 M urea gel. Edman degradation of the peptide fragment recovered from the band that migrated closest to the free DNA band revealed the amino acid sequence KKPIXKK (SEQ ID NO: 185), where X indicates a modified amino acid that could not be identified with the 20 derivatized amino acid standards. This peptide sequence, where X is phenylalanine, corresponds to amino acids 80–86 in the PDGF-B chain (Johnsson et al., (1984) EMBO J. 3: 921–928) which in the crystal structure of PDGF-BB comprises a part of solvent-exposed loop III (Oefner et al., (1992) EMBO J. 11: 3921–3926). In the PDGF A-chain, this peptide sequence does not occur (Betsholtz et al, (1986) Nature 320, 695–699). Together, these data establish a point contact between a specific thymidine residue in ligand 20t and phenylalanine 84 of the PDGF B-chain.

Example 13

Inhibition of PDGE by Nucleic Acid Ligands

Figure 7:
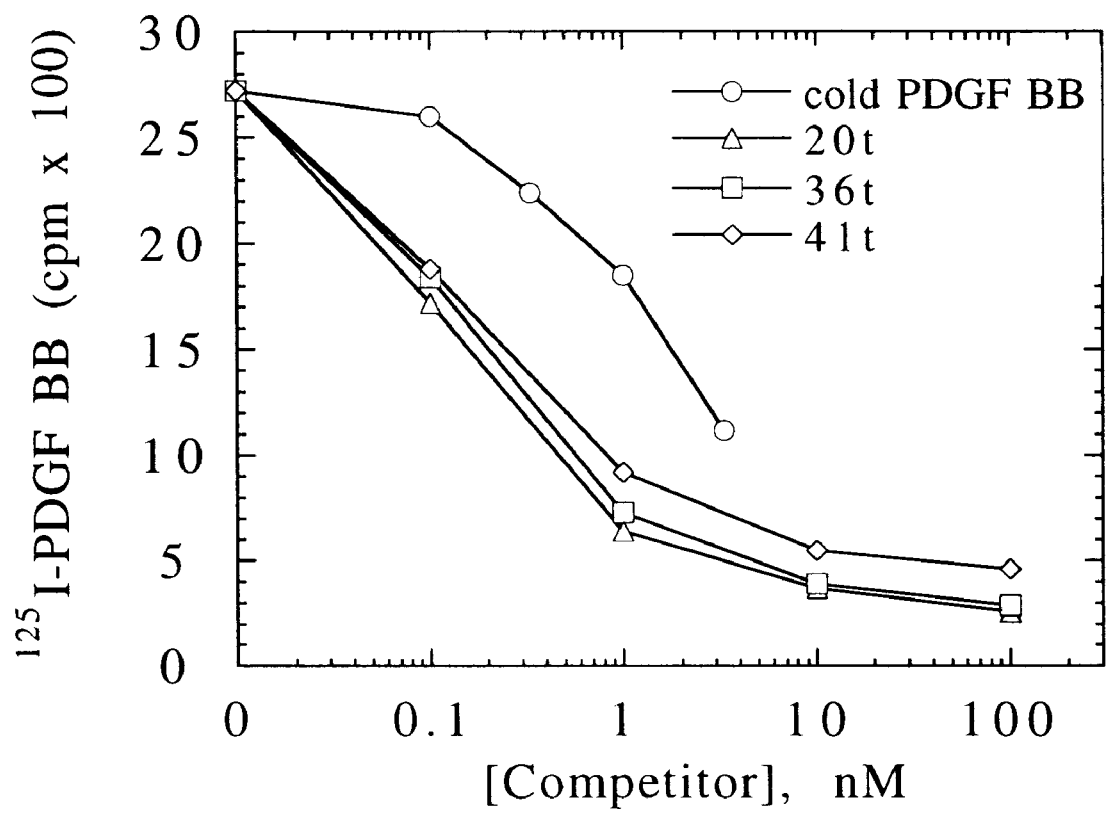
FIG. 7 shows the effect of DNA ligands on the binding of $^{125}$I-PDGF-BB and $^{125}$I-PDGF-AA to PDGF α-receptors expressed in PAE cells.

In order to determine whether the DNA ligands to PDGF were able to inhibit the effects of PDGF isoforms on cultured cells, the effects on binding of $^{125}$I-labeled PDGF isoforms to PDGF α- and β-receptors stably expressed in porcine aortic endothelial (PAE) cells by transfection was determined. Ligands 20t, 36t and 41t (SEQ ID NOS:172–174) all efficiently inhibited the binding of $^{125}$1-PDGF-BB to PDGF α-receptors (FIG. 7) or PDGF β-receptors (data not shown), with half maximal effects around 1 nM of DNA ligand. DNA ligand T39, directed against thrombin and included as a control, showed no effect. None of the ligands was able to inhibit the binding of $^{125}$I-PDGF-AA to the PDGF α-receptor (FIG. 7), consistent with the observed specificity of ligands 20t, 36t and 41t for PDGF-BB and PDGF-AB.

Figure 8:
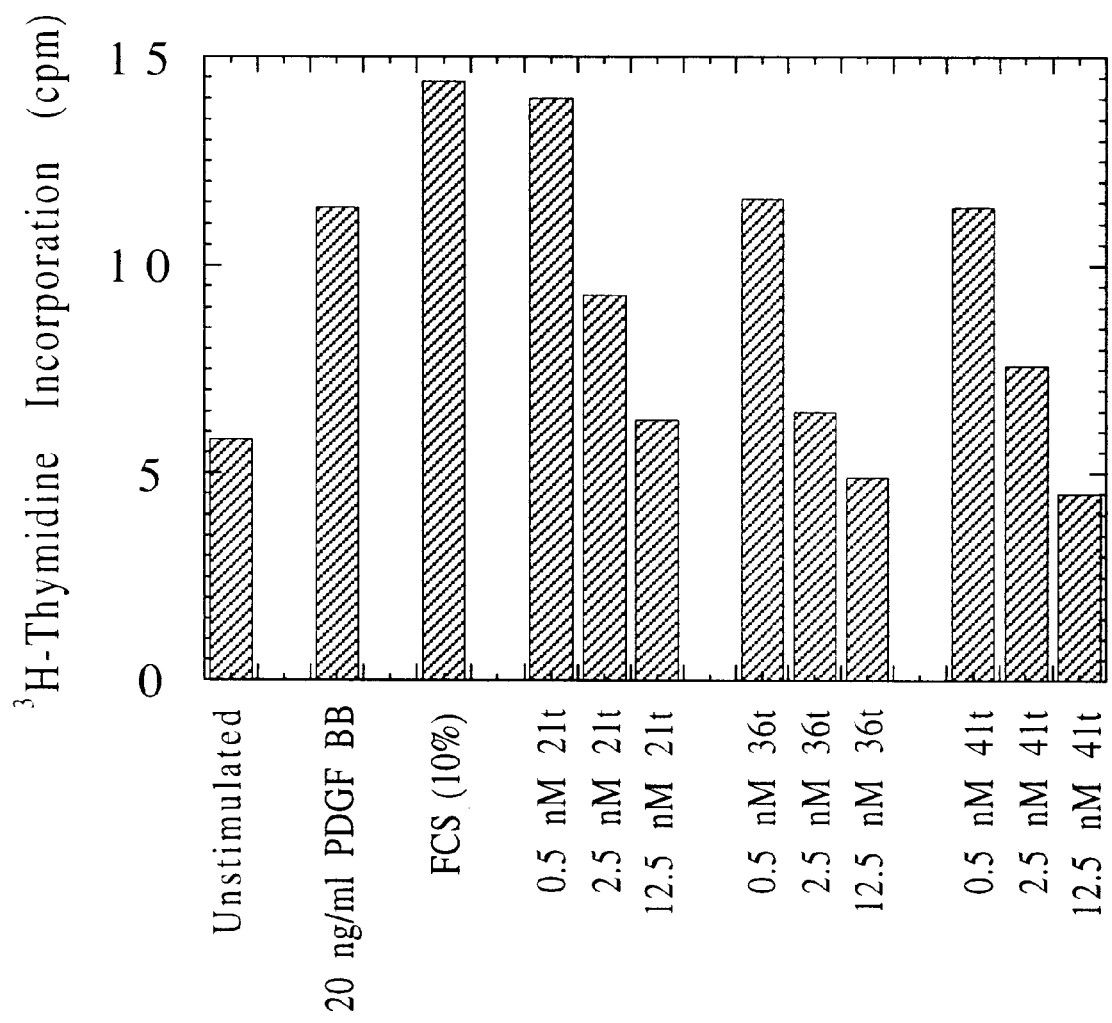
FIG. 8 shows the effect of DNA ligands on the mitogenic effect of PDGF-BB on PAE cells expressing the PDGF β-receptors.

The ability of the DNA ligands to inhibit the mitogenic effects of PDGF-BB on PAE cells expressing PDGF β-receptors was investigated. As shown in FIG. 8, the stimulatory effect of PDGF-BB on [$^3$H]thymidine incorporation was neutralized by ligands 20t, 36t and 41t. Ligand 36t exhibited half maximal inhibition at the concentration of 2.5 nlM; ligands 41t was slightly more efficient and 20t slightly less efficient. The control ligand T39 had no effect. Moreover, none of the ligands inhibited the stimulatory effects of fetal calf serum on [$^3$H]thymidine incorporation in these cells, showing that the inhibitory effects are specific for PDGF.

Example 14

Post-Selex Process Nucleotide Substitutions

Figure 9:
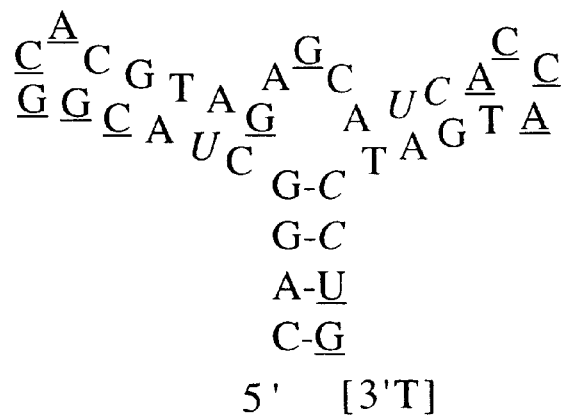
FIG. 9 shows the 2'-O-methyl-2'-deoxy- and 2'-fluoro-2'-deoxyribonucleotide-substitution pattern compatible with high affinity binding to PDGF-AB. Underlined symbols indicate 2'-O-methyl-2'-deoxynucleotides; italicized symbols indicate 2'-fluoro-2'-deoxynucleotides; normal font indicates 2'-deoxyribonucleotides; [3'T] indicates inverted orientation (3'3') thymidine nucleotide (Glen Research, Sterling, Va.); PEG in the loops of helices II and III indicates pentaethylene glycol spacer phosphoramidite (Glen Research, Sterling, Va.).
Figure 9:
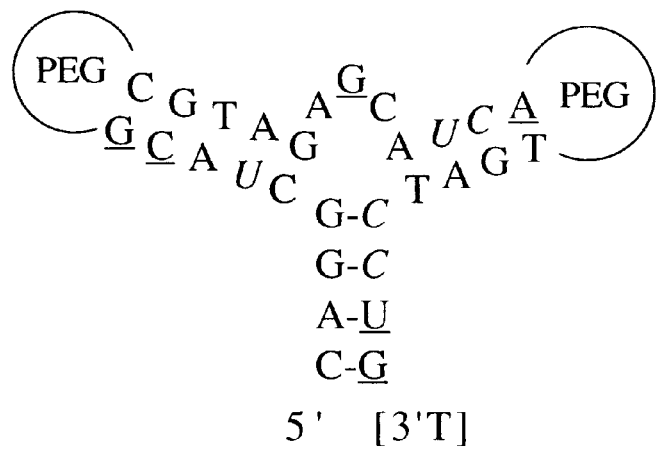

The stability of nucleic acids to nucleases is an important consideration in efforts to develop nucleic acid-based therapeutics. Experiments have shown that many, and in some cases most of the nucleotides in SELEX-derived ligands can be substituted with modified nucleotides that resist nuclease digestion, without compromising high affinity binding (Green et al, (1995) Chemistry and Biology 2: 683–695; Green et al., (1995) J. Mol. Biol. 27, 60–68). Experiments of this type with the DNA ligands reported here suggest that substitutions with modified nucleotides are tolerated at many positions (FIG. 9; SEQ ID NOS:175–176). Specifically, we have examined the substitution of 2'-O-methyl-2'-deoxy- and 2'-fluoro-2'-deoxyribonucleotides for 2'-deoxyribonucleotides in ligand 36t, by examining the PDGF-AB binding properties of singly or multiply substituted ligand 36t. The substitution pattern indicated in FIG. 9 is compatible with high affinity binding to PDGF-AB. Furthermore, this ligand tolerates the substitution of pentaethylene glycol spacers (Glen Research, Sterling, Va.) for the trinucleotide loops at the ends of helices II and III (FIG. 9). These DNA ligands therefore represent lead compounds for a novel class of high affinity, specific antagonists of PDGF-AB and PDGF-BB.

Example 15

Experimental Procedure for Evolving 2'-Fluoro-2'-Deoxypyrimidine RNA Ligands to PDGE and RNA Sequences Obtained A. 2'-Fluoro-2'-Deoxypyrimidine RNS SELEX SELEX with 2'-fluoro-2'-deoxypyrimidine RNA targeting PDGF AB was done essentially as described previously (vide supra, and Jellinek et al., (1993, 1994) supra) using the primer template set as shown in Table 12 (SEQ ID NOS:125–127). Briefly, the 2'-fluoro-2'-deoxypyrimnidine RNA for affinity selections was prepared by in vitro transcription from synthetic DNA templates using T7 RNA polymerase (Milligan et al., Nucl. Acids Res., 15: 8783 (1987)). The conditions for in vitro transcription described in detail previously (Jellinek et al., (1994) supra) were used, except that higher concentration (3 mM) of the 2'-fluoro-2'-deoxypyrirmidine nucleoside triphosphates (2'-F-UTP and 2'-F-CTP) was used compared to ATP and GTP (1 mM). Affinity selections were done by incubating PDGF AB with 2'-fluoro-2'-deoxypyrimidine RNA for at least 15 min at 37° C. in PBS containing 0.01% human serum albumin. Partitioning of free RNA from protein-bound RNA was done by nitrocellulose filtration as described (Jellinek et al., (1993, 1994) supra). Reverse transcription of the affinity-selected RNA and amplification by PCR were done as described previously (Jellinek et al., (1994) supra). Nineteen rounds of SELEX were performed, typically selecting between 1–12% of the input RNA. For the first eight rounds of selection, suramin (3–15 μM) was included in the selection buffer to increase the selection pressure. The affinity-enriched pool (round 19) was cloned and sequenced as described (Schneider et al., (1992) supra). Forty-six unique sequences have been identified, and the sequences are shown in Table 13 (SEQ ID NOS:128–170). The unique-sequence ligands were screened for their ability to bind PDGF AB with high affinity. While random 2'-fluoropyrimidine RNA (Table 12) bound to PDGF with a dissociation constant (Kd) of 35±7 nM, many of the affinity-selected ligands bound to PDGF AB with ≈100-fold higher affinities. Among the unique ligands, clones 9 ($K_d$=91±16 pM), 11 ($K_d$=120±21 pM), 16 ($K_d$=116±34 pM), 23 ($K_d$=173±38 pM), 25 ($K_d$=80±22 pM), 37 ($K_d$=97±29 pM), 38 ($K_d$=74±39 pM), and 40 ($K_d$=91±32 pM) exhibited the highest affinity for PDGF AB (binding of all of these ligands to PDGF AB is biphasic and the $K_d$ for the higher affinity binding component is given).

Example 16

Experimental Procedures

This Example provides the general procedures followed and incorporated in Examples 17–19 for the evolution of nucleic acid ligands to hKGF.

A. Materials and Methods

Recombinant human Keratinocyte Growth Factor (hKGF) and human Epidermal Growth Factor (HEGF) were purchased from Upstate Biotechnology Inc.(Lake Placid, N.Y.). haFGF, hbFGF, PDGF-AB, TGFβ1, and anti-KGF neutralizing monoclonal antibody were purchased from R&D Systems (Minneapolis, Minn.). Recombinant rat KGF was purchased from QED Advanced Research Technologies (San Diego, Calif.). Human thrombin was purchased from Enzyme Research Laboratories (South Bend, Ind.). T4 DNA ligase, HpaII methylase, and restriction enzymes were purchased from New England Biolabs (Beverly, Mass.). pCR-Script Amp SK(+) cloning kit was purchased from Stratagene (La Jolla, Calif.). AMV reverse transcriptase was purchased from Life Sciences (St. Petersburg, Fla.). Taq DNA polymerase was purchased from Perkin Elmer (Foster City, Calif.). Ultrapure nucleotide triphosphates were purchased from Pharmacia (Piscataway, N.J.). α-$^{32}$-P-ATP, γ-$^{32}$P-ATP, and 5'$^{32}$P-cytidine 3', 5'-bis (phosphate) (5'$^{132}$P-pCp) were from DuPont NEN Research Products (Boston, Mass.). $^{125}$I-labeled KGF was prepared as described before (Bottaro et al., (1990) *J.Biol.Chem.* 265:12767–12770). PC-3 prostatic carcinoma cells were obtained from ATCC (catalog number CRL1435). Balb/MK cells and NIH3T3 transfected cells with the human KGF receptor (NIH3T3/ KGFR) were a generous gift from S. Aaronson, Mt. Sinai Medical Center, New York, and have been described elsewhere (Miki et al., (1992) *Proc.Natl.Acad.Sci.USA* 89:246–250; Miki et al., (1991) *Science* 251:72–75; Weissman et al., (1983) *Cell* 2;599–606). T7 RNA polymerase, 2'NH$_2$- and 2'F-modified CTP and UTP were from NeXstar Pharmaceuticals, Inc. (Boulder, Colo.). DNA oligonucleotides were obtained from Operon Technologies, Inc. (Alameda, Calif.). Nitrocellulose/cellulose acetate mixed matrix, 0.45 μm, HA filters were from Millipore (Bedford, Mass.). Calcium and magnesium containing Dulbeco's Phosphate Buffered Saline (DPBS) was purchased from Life Technologies (Gaithersburg, Md.). Chemicals were at least reagent grade and purchased from commercial sources.

B. SELEX

The SELEX procedure has been described in detail in U.S. Pat. No. 5,270,163 (see also Tuerk and Gold (1990) *Science* 249:505–510). A single-stranded DNA (ssDNA) pool was used to generate the double-stranded (dsDNA) template for generating the initial random sequence RNA pool by transcription. The DNA template contained 40 random nucleotides, flanked by 5' and 3' constant regions for primer anealing sites for PCR and cDNA synthesis (Table 14; SEQ ID NOS:186–188). The 5' primer contains the T7 promotor sequence for in vitro transcriptions. The template was PCR amplified following an initial denaturation at 93° C. for 3.5 minutes through 15 cycles of 30 second denaturation at 93° C., 1 minute annealing at 60° C., and 1 minute elongation at 72° C., in 50 mM KCl, 10 mM Tris-HCl, pH9, 0.1% Triton X-100, 3 mM MgCl$_2$, 0.5 mM of each dATP, dCTP, dGTP, and dTTP, 0.1 units/μl Taq DNA polymerase, and 2.5 nM each of 3G7 and 5G7 primers (Table 14; SEQ ID NOS.187–188). SELEX experiments for hKGF were initiated with a random sequence pool of RNA in which all pyrimidines were 2'-NH$_2$-modified or 2'-F-modified. Transcription reactions were done with about 5 μM DNA template, 5 units/μT7 RNA polymerase, 40 mM Tris-HCl (pH8), 12 mM MgCl$_2$, 5mM DTT, lmM spermidine, 0.002% Triton X-100, 4% PEG 8000, 2–4 mM each 2'OH ATP, 2'OH GTP, 2'NH$_2$ or 2'F CTP, 2'NH$_2$ or 2'F UTP, and 0.25 μM α$^{32}$P 2'OH ATP (800 Ci/mmole). The full length transcripts were gel-purified prior to use. To prepare binding reactions, the RNA molecules were incubated with recombinant hKGF in Dulbecco's Phosphate-Buffered Saline (DPBS) with calcium and magnesium (Life Technologies, Gaithersburg, Md., Cat. No 21300-025) containing 0.01% human serum albumin. Following incubation at room temperature (ranging from 10 minutes to 10 hours) the protein-RNA complexes were partitioned from unbound RNA by filtering through nitrocellulose. Nitrocellulose filter bound RNA was recovered by phenol/urea extraction. The partitioned RNA was reverse transcribed into cDNA by AMV reverse transcriptase at 48° C. for 60 min in 50 mM Tris-HCl pH8.3, 60 mM NaCl, 6 mM Mg(OAc)$_2$, 10 mM DTT, 50 pmol DNA 3' primer (Table 14), 0.4 mM each of dATP, dCTP, dGTP, and dTTP, and 1 unit/μl AMV RT. The cDNA was PCR amplified and used to initiate the next SELEX cycle.

C. Nitrocellulose Filter Partitioning

In order to partition the protein-RNA complexes, the binding reactions were filtered through nitrocellulose/ cellulose acetated mixed matrix, 0.45 μm pore size (filter disks, Millipore, Co., Bedford, Mass.). For filtration, the filters were placed onto a vacuum manifold and wetted by aspirating 5 ml of DPBS. The binding reactions were aspirated through the filters, and following a 5 ml wash, the filters were counted in a scintillation counter (Beckmann). Higher wash volumes with DPBS or 0.5 M urea were used as a means to increase selection stringency as shown in Table 15. Gel purified, internally α-$^{32}$P-ATP labeled transcripts were incubated with various concentrations of hKGF in DPBS at 37° C. for 10 minutes. Oligonucleotide protein mixtures were filtered through prewetted 0.45 μm pore size HA filters, followed by a 5 ml wash with DPBS. The radioactivity retained on the filter was counted and corrected for background binding in the absence of protein. Nonlinear least square method was used to fit the data into monophasic or biphasic binding curves and to obtain the equilibrium dissociation constant $K_d$ (Jellinek et al., (1993) *Proc. Natl. Acad. Sci. USA* 90:11227–11231) using the software package Kaleidagraph (Synergy Software, Reading, Pa.). Biphasic binding can be described as the binding of two affinity species that are not in equilibrium.

D. Cloning and Sequencing

The RNA recovered from the round 8 filters was reverse transcribed and PCR amplified. Following column purification with QIA-quick spin columns (Qiagen, Inc., Chatsworth, Calif.) and ethanol precipitation, the amplified DNA was methylated with HpaII methylase (New England Biolabs, Beverly, Mass.). The methylated DNA was cloned into the SrfI restriction site of pCR-Script Direct SK(+) plasmid using the pCR-Script Amp SK(+) cloning kit (Stratagene Cloning Systems, La Jolla, Calif.). About 80 clones were sequenced with Sequenase sequencing kit (United States Biochemical Corporation, Cleveland, Ohio). Sequence analysis and secondary structure prediction was done by using previously described computer software (Feng and Doolittle (1987) *J. Mol. Evol.* 25:351–360; Jaeger et al., (1989) *Proc. Natl. Acad. Sci. USA* 86:7706–7710; Jaeger et al., (1990) *Methods Enzymol.* 183:281–306; Zucker (1989) *Science* 244:48–52).

E. Determination of Minimal Sequences Necessary for Binding

Oligonucleotide ligands end labeled at the 5' end with $\gamma$-$^{32}$P-ATP using T4 polynucleotide kinase, or at the 3' end with 5'-$^{32}$P-pCp and T4 RNA ligase, were used to establish 3' and 5' boundaries respectively (Fitzwater et al., (1996) *Methods Enzymol.* 267:275–301). After partial alkaline hydrolysis, the radiolabeled oligonucleotide was incubated with 0.1, 0.6, and 3.0 nM hKGF, and the protein bound oligonucleotide was isolated by nitrocellulose filtration. The nitrocellulose retained oligonucleotide truncates were analyzed on a high resolution denaturing polyacrylamide gel. An alkaline hydrolysis ladder and a ladder of radioactively labeled ligands terminated with G-residues, generated by partial RNase T1 digestion, were used as markers to map the 3' and 5' boundaries.

F. Thermal Denaturation Profiles

Oligonucleotide melting profiles were obtained with a Cary Model 1E spectrophotometer. Oligonucleotides were heated to 95° C. in PBS (Sambrook et al., (1989) *Molecular Cloning: A Laboratory Manual.* 2nd Ed., Cold Spring Harbor, N.Y.) or 10 mM phosphate buffer and cooled to room temperature before recording the melting profile. The melting profiles generated show the change in absorbance at 260 nm as a function of temperature. During recording, the samples were heated at a rate of 1° C. min$^{-1}$ from 20–95° C.

Example 17

RNA Ligands to hKGF

A. SELEX

To generate RNA ligands for hKGF, two parallel SELEX experiments were initiated, one with 2'-NH$_2$ and the other 2'-F pyrimidine modified RNA molecules randomized at 40 contiguous positions. The SELEX conditions and results for each round are summarized in Table 15. The starting pool contained 5×10$^{14}$ (500 pmoles) and 2.5×10$^{14}$ (250 pmoles) 2'-NH$_2$ and 2'-F pyrimidine modified RNA molecules, respectively, and bound to hKGF with an approximate K$_D$ of 30 nM. After 8 rounds of SELEX, the evolved pools bound with a K$_D$ of 0.6 nM. No further improvement in the K$_D$ was observed in the subsequent two rounds. The RNA pools from the 8th round were reverse transcribed, PCR amplified and cloned as described.

B. RNA Sequences

Figure 12A:
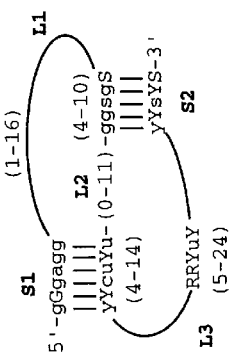
FIGS. 12A–D show the proposed alignment of 2'F and 2'NH$_2$ ligands. Lower case, italicized sequence residues indicate the constant region of the template. In the consensus sequences, capital and lower case letters are used for residues found in greater than or equal to 80% and 60% of the members of each family respectively. $K_d$ and $K_i$ values are also shown next to the designation of each ligand. The $K_i$ values shown here were calculated using the formula $K_i$=IC50/(1+(C/$K_d$)), where IC50 is the measured half maximal inhibitory concentration of each ligand in the PC-3 cell assay as described in Example 16; C is the concentration of $^{125}$I-KGF; and $K_d$ is the equilibrium dissociation constant of KGF for its receptor, (about 150 pM). The ligands marked with stars show biphasic binding curves.
Figure 12B:
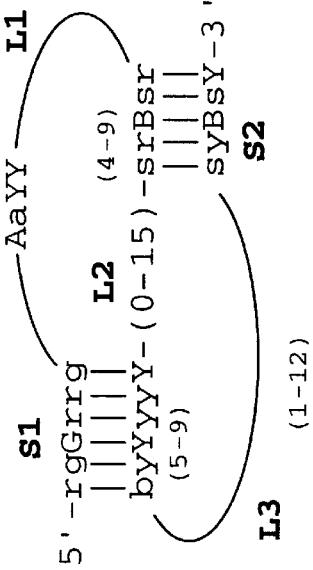
Figure 12C:
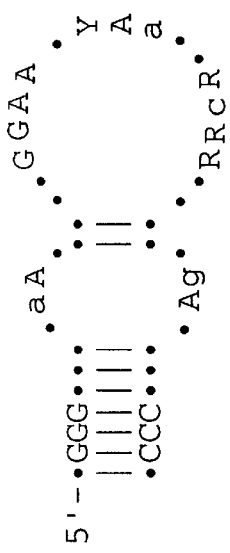
Figure 12D:
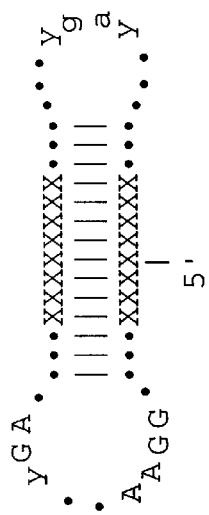

In the 2'-NH$_2$ SELEX, 29 out of 31 clones were unique. In the 2'-F SELEX all 43 clones sequenced were unique. A unique sequence is defined as one that differs from all others by three or more nucleotides. Table 16 lists the sequences (SEQ ID NOS:189–262) of all of the clones sequenced in standard single letter code (Cornish-Bowden, (1985) *Nucleic Acid Res* 13:3021–3030). Computer assisted global and local alignment did not reveal any extensive homologies among the clones, and no obvious families were apparent. The 2'-NH$_2$ clones are in general purine rich while the 2'-F clones are pyrimidine rich. When the alignment parameters were relaxed, the Feng/Doolittle algorithm grouped the 2'-NH$_2$ clones in one family and the 2'-F clones in another. Visual inspection of the sequences suggested two and three possible families for the 2'-NH$_2$ and the 2'-F ligands, respectively. Using conserved predicted secondary structure, 38 2° F ligands could be assigned into two classes (FIGS. 12A and 12B). Similarly, 15 2'NH$_2$ ligands could be assigned into two classes (FIGS. 12C and 12D). The two proposed classes for the 2'F ligands can be folded into pseudoknot structures (Wyatt et al., (1993) *The RNA World* 465–496; ten Dam, E. (1992) *Biochemistry* 31:1665–1676). These structures are very related and in fact they could be circular permutations of a common structure. Loop 3 (L3) of class 1 pseudoknots presents the conserved sequence 5'RRYuy while loop 1 (L1) of class 2 ligands presents the sequence 5'AaYY. Both of these sequences contain the consensus 5'RRYY. Some of the 2'F ligands contain two to three copies of the RRYY sequence (FIGS. 12A and 12B). Another feature of these structures is the unequal distribution of purines and pyrimidines in stem 1 (S1). One strand of that stem contains almost exclusively purines while the other strand contains pyrimidines.

Class 1 of the 2'NH$_2$ ligands includes 8 members that can be folded into stem-loop structures with internal symmetric or asymmetric loops. The stem contains three consecutive GC base pairs. The terminal loops are long and present the conserved sequence 5'GGAA(N)$_{1-14}$YAA(N)$_{1-7}$RCRR (SEQ ID NO:263). Both sides of the internal asymmetric loops of the class 1 ligands contain the sequence 5'AA. Class 2 includes 7 ligands that can be folded into dumbbells with variable sized loops. One loop contains the conserved sequence 5'YGAY while the other loop contains the conserved sequence 5'GGAA(N)$_{0-4}$YGA (SEQ ID NO:264). Clones 2N and 54N are circular permutations of the remaining 5 clones.

C. Affinities

The dissociation constants of the hKGF ligands were determined by nitrocellulose filter binding and are listed in Table 17. Eight out of 41 2'-F ligands bound biphasically. The remaining of the 2'-F and all the 2'-NH$_2$ ligands bound monophasically. Under protein excess, biphasic binding suggests that the ligand exists as two affinity species (presumably isoconformers) that are not in equilibrium. The best 2'-F-modified ligand, K14F, binds biphasically with the high and low affinity dissociation constant at about 0.3–3 pM and 2–10 nM respectively. There is some observed variability in the K$_D$ determinations for the various clones and the random RNA. Despite the experimental variability in the K$_D$ determinations, the high affinity species of K14F have a 1,000–5,000 fold better affinity than the random RNA. Among the monophasic 2'-F-modified ligands, K38F had the best KD of about 0.3nM. The best 2'-NH$_2$-modified ligands, bound with a KD of 0.4 nM which represent about 75 fold improvement over the random RNA.

D. Determination of Minimal Sequences Necessary for Binding

Figure 13:
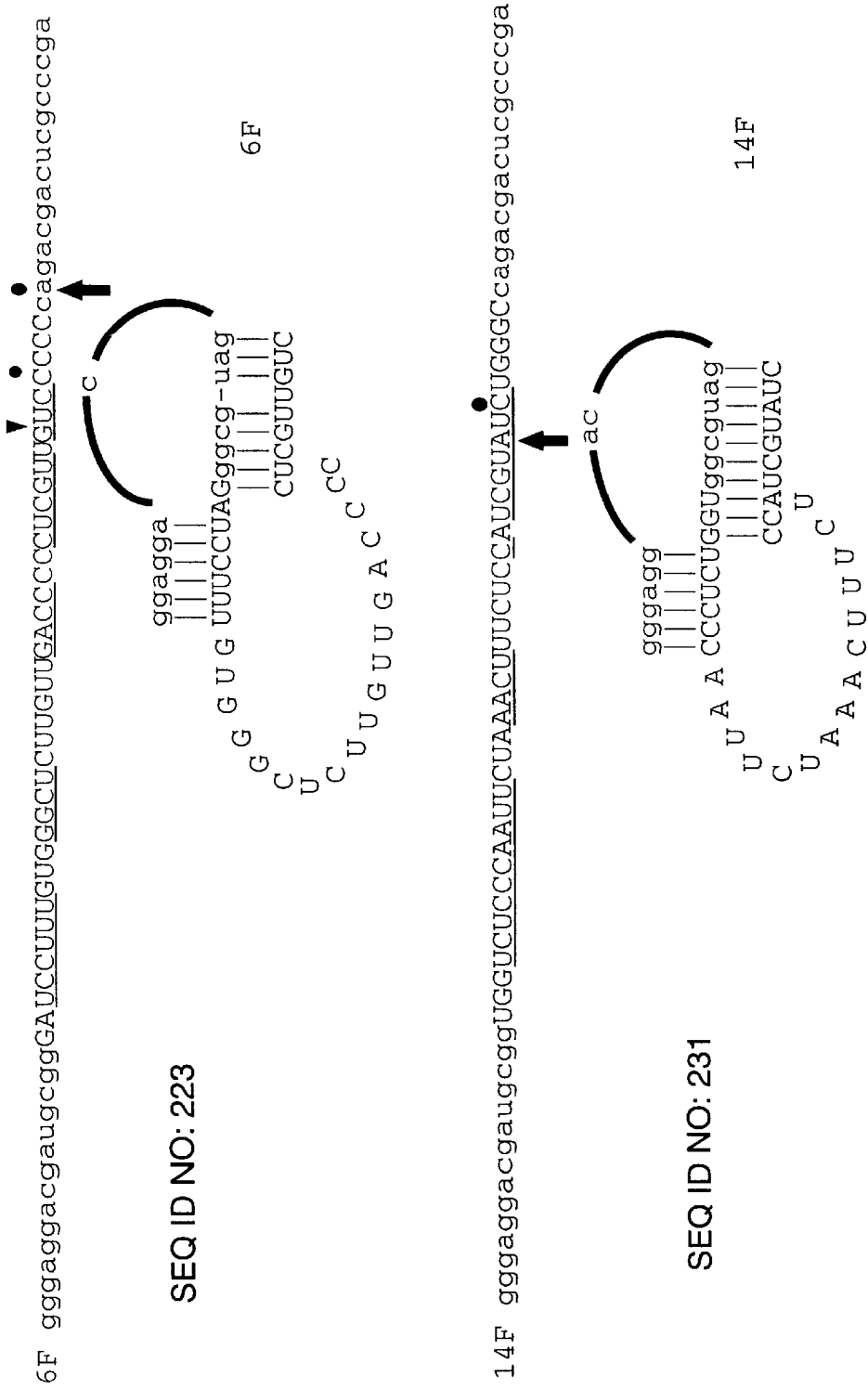
FIG. 13 shows the minimal sequence requirement for binding of ligand 6F and 14F to hKGF. The predicted folding of each ligand is shown. Constant regions of the ligands are shown in lower case. Conserved sequences are underlined. Circles and triangles mark the 3' ends of active and inactive truncates respectively.

Two 2'F ligands (6F and 14F) (SEQ ID NOS:223 and 231) were studied further to determine the minimal sequences necessary for binding. Sequence boundaries were determined by allowing an alkaline hydrolysis ladder, labeled at the 3' or 5' end, to bind to hKGF. The partial fragments were affinity purified by nitrocellulose filtration and analyzed on high resolution denaturing gels. Boundaries were clearly observed only at the 3' ends for both ligands (FIG. 13) and are in agreement with the class 1 proposed folding as shown in FIGS. 12A and 12B. Truncated templates were then used to confirm the boundaries (FIG. 13). Three truncates were tested for 6F because a run of 7 consecutive pyrimidines did not allow the precise mapping of the boundary. From these three truncates, one lost its KGF binding activity as shown in FIG. 13. A single 14F truncate, designated 14F3'T, was tested. This truncate was two bases longer than the observed boundary in order to extend stem 2 (S2) of the proposed pseudoknot structure. The 14F3'T truncated ligand retained binding activity with affinity similar to the full length ligand. Like the full length ligand, 14F3'T bound KGF biphasically where the high affinity species represented about 20% of the molecules and showed $K_d$ values of about 0.3–3 pM. These high affinity species when partially separated from the low affinity species on the basis of differential affinity to KGF, exhibited binding curves with mid points at 0.3–3 pM and maximum plateaus of about 70% (data not shown). FIG. 13 shows the predicted folding of the shortest active truncates for 6F and 14F which are 53 and 49 bases long respectively. Both proposed pseudoknot structures contain relatively long stems. The two proposed stems of 6F are separated by a single base forming a non-H-type pseudoknot. The proposed 6F structure resembles the solution structure of a similar pseudoknot motif from a frame-shifting element found in the MMTV RNA (Shen et al., (1995) *J. Mol. Biol.* 247:963–978). The two stems (S1 and S2) of 14F could be drawn as two coaxially stacked helices of 16 base pairs total length (H-type pseudoknot). A Similar pseudoknot structure has been proposed before, based on NMR data (Du et al., (1996) *Biochemistry* 35:4187–4198). Given the short length of L1, it is possible that ligand 14F forms a non-H-type pseudoknot where the last GU base pair of S1 is not formed allowing a more flexible helical region and a longer L1. Temperature melting curves of 14F and 14F3'T suggest a remarkable thermostability for this ligand (data not shown). These melting curves appear to be concentration independent and biphasic in 150 mM salt. Biphasic melting curves have been observed before with tRNA (Hilbers et al., (1976) *Biochemistry* 15:1874–1882), and have been attributed to the tertiary folding of the RNA molecule. Multiphasic temperature transitions have also been proposed for RNA pseudoknots (Du et al., (1996) *Biochemistry* 35:4187–4198). The biphasic curves observed include a low Tm at about 55° C. and a high Tm of greater than 85–90° C. In 10 mM salt the low Tm of 14F is not observed while the high Tm is shifted down to 75–78° C. The melting profile for 14F appears to be flatter than 14F3'T even though the Tm values are the same. The data suggest that the observed thermostability is attributable to just the minimal 49-mer.

In an effort to identify shorter KGF ligands that retained binding, the binding activity of various deletions of the shortest truncate of ligand 14F, namely 14F3'T were tested. Deletions were tested in all the structural elements of the proposed pseudoknot structure. The results are summarized in Table 23 (SEQ ID NOS:272–304). RNA transcripts containing 2'F pyrimidines and 2'OH purines were obtained by in vitro transcription using synthetic DNA templates. The activity of each ligand is shown by scoring for both the high (H) and low (L) affinity component of the 14F3'T binding curve with + (active) or − (not active). Truncates T35 and T36 represent two complementary halves of 14F3'T molecule and were additionally tested as an equimolar mixture. The structural elements of the proposed pseudoknot structure are separated by (|) and are indicated by symbols S1 (stem 1), S2 (stem 2), L1 (loop 1) and L3 (loop 3). The proposed pseudoknot structure for 14F3'T is a non-H-type pseudoknot and lacks L2 (loop 2). The complementary sequences forming SI (S1 and S1') and S2 (S2 and S2') are marked by single and double underlines respectfully. In the tabulated sequences, deleted bases were replaced with periods (.). Any deletion attempt in the stems S1 and S2 of the proposed pseudoknot structure resulted in loss of both the high (H) and low (L) affinity component of the binding curve as observed with the 14F3'T ligand. Deletions in loop 3 (L3), however, were tolerated as long as one copy of the RRYY box remained intact. The shortest ligand that retained activity is T22 which is a 43-mer. In trying to obtain shorter ligands by truncating L3 futher a mutant version of T22 (designated T22mu) was used where the last GC base pair of SI was eliminated by a G to U mutation at position 6. The reasoning for this mutation was to enhance the flexibility of the double stranded region of this ligand by allowing an unpaired base between S1 and S2. Although this mutation did not affect the binding of T22 it did not allow further active truncations in L3.

E. Specificity of RNA Ligands to hKGF

The specificity of the K14F ligand was tested by determining its $K_D$ against rat hKGF, and the heparin binding human growth factors, AFGF, bFGF, and PDGF (Table 18). The results suggest that the K14F binds all tested targets like random RNA, except hKGF, and it can discriminate between hKGF and other similar proteins by a factor of 400–40,000.

The specificity of ligand 14F3'T was tested by determining its $K_d$ against a variety of heparin binding proteins. The results summarized in Table 22 show that ligand 14F3'T can discriminate KGF from all other heparin binding proteins tested by a factor of $1.2 \times 10^4$–$3 \times 10^{10}$. Ligand 14F3'T binds only to KGF with high affinty while it binds all other heparin binding proteins tested like random RNA. Binding of 14F3'T to the rat KGF, which is 91% identical to human KGF, is with about a 5–10 fold reduced affinity. Similar specificity was observed during the inhibition of the KGF induced DNA synthesis of Balb/MK cells. Ligand 14F3'T inhibits rat KGF induced DNA synthesis with a $K_i$ of 1.8 nNM which is 20–50 fold higher than the $K_i$ observed with the human KGF. Ligand 14F3'T inhibits the DNA synthesis of Balb/MK cells only if it is the result of KGF but not EGF stimulation (data not shown).

Example 18

Inhibition of hKGF Binding to Cell Surface Receptors

A. Receptor Binding Assay

To test the ability of the hKGF ligands to competitively inhibit the binding of hKGF to its cell surface receptor, two cell lines were used. The first cell line, PC-3, is an isolate from a grade IV prostatic adenocarcinoma (ATCC CRL 1435). The second cell line is designated as NIH3T3/FGFR-2 and is a recombinant NIH/3T3 cell line carrying the human hKGF receptor at about 0.5–1×10⁶ high affinity KGF binding sites per cell (Miki et al., (1992) *Proc. Natl. Acad. Sci. USA* 89:246–250).

PC-3 cells were plated in 24-well plates at about $10^5$ cells per well. Following growth for 48–36 hours, the cells were serum starved for 24 hours, washed two times with 500 µl of cold DPBS, and then incubated with 500 µl binding buffer (BB1; DPBS, 0.5 mM MgCl$_2$, 0.2% BSA. 0.02% sodium azide) containing various concentrations of $^{125}$I-labeled KGF ranging from 0 to 0.8 nM. Following 3–3.5 hour incubation at 4° C., the binding mixes were aspirated and the well-adhered cells were washed two times with 1 ml BB1 and once with 1 ml BB1 supplemented with 0.5M NaCl. The remaining bound labeled hKGF was solubilized in 600 µl 0.5% SDS/0.1M NaOH and counted in a gamma counter (Beckmann). Nonspecific binding was determined in the presence of 100 fold molar excess of unlabeled hKGF. For competition assays, the labeled hKGF was kept constant at 0.3 nM, and varying concentrations of competitor molecules were included in the binding reactions ranging from 0–1,000 nM. Binding curves were fitted to the equation:

[Bound Tracer]=([Total Tracer]* [Receptor])/($K_D$+[Total Tracer])

where [Total Tracer] and [Bound Tracer] were fixed and the $K_D$ and [Receptor] were determined by regression analysis using the software Kaleidagraph (Synergy Software, Reading, Pa.).

NIH3T3/KGFR-2 cells were plated in 24-well plates at about $10^5$ cells per well. Following growth overnight, the cells were serum starved for 1–5 hours, washed two times with 500 µl binding buffer (BB2: serum-free MEM growth medium, 0.1% BSA, 25mM HEPES, pH 7.4), and then incubated with 250 µl BB2 containing 1 µg/ml heparin (from bovine lung, SIGMA, St. Louis, Mo.), $^{125}$I-labeled hKGF at 0.03 nM, and varying concentrations of competitor molecules (300 mM–0 nM). Following 1 hour incubation at room temperature, the binding mixes were aspirated, and the wells were washed two times with 250 µl cold DPBS and once with 250 µl cold DPBS supplemented with 0.5M NaCl. The bound labeled hKGF was solubilized in 500 µl 0.5% SDS and counted in a scintillation counter (Beckmann).

The inhibition constants (Ki) of the RNA ligands were determined by a nonlinear regression analysis of the data.

Figure 10A:
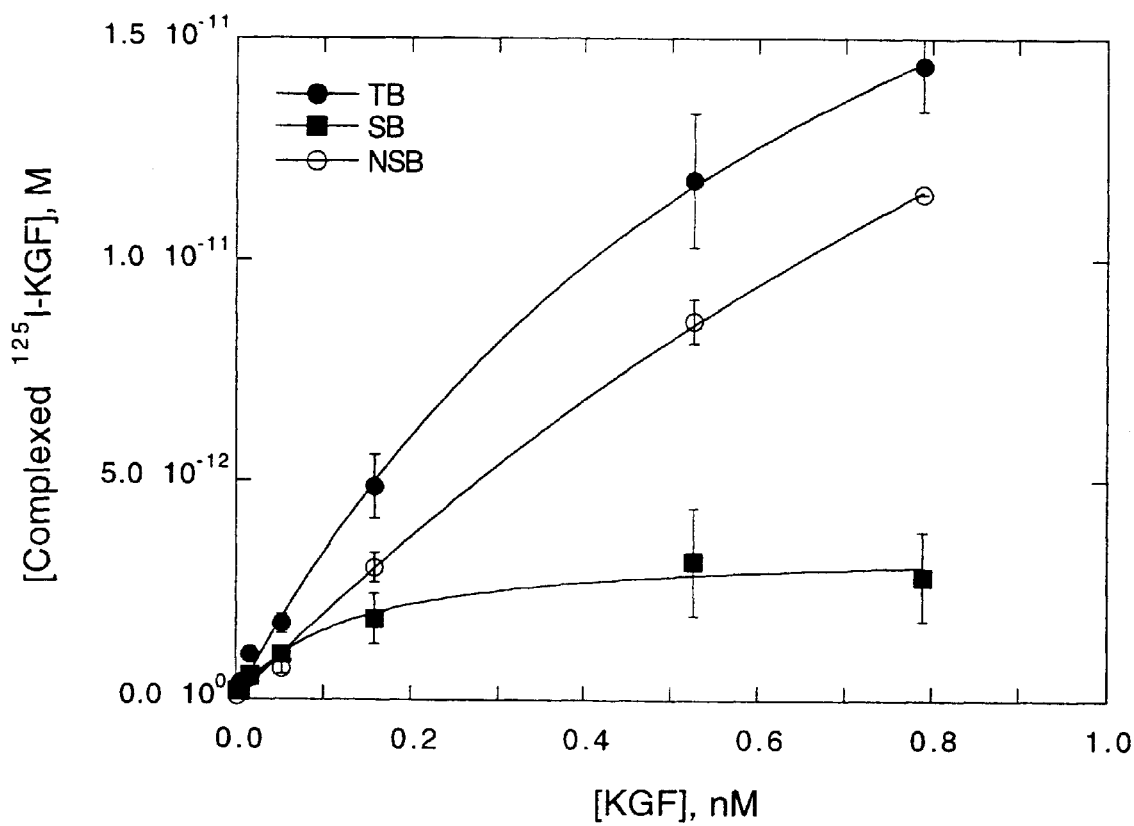
FIG. 10A shows the saturation binding of radiolabeled hKGF on the surface of the PC-3 cells. TB (total binding) is the binding observed in the absence of competing unlabeled hKGF, whereas NSB (nonspecific binding) is the binding observed in the presence of 100 fold molar excess of unlabeled hKGF. SB (specific binding) demonstrates the specific binding, and this curve was derived by subtracting the NSB curve from the TB curve.
Figure 10B:
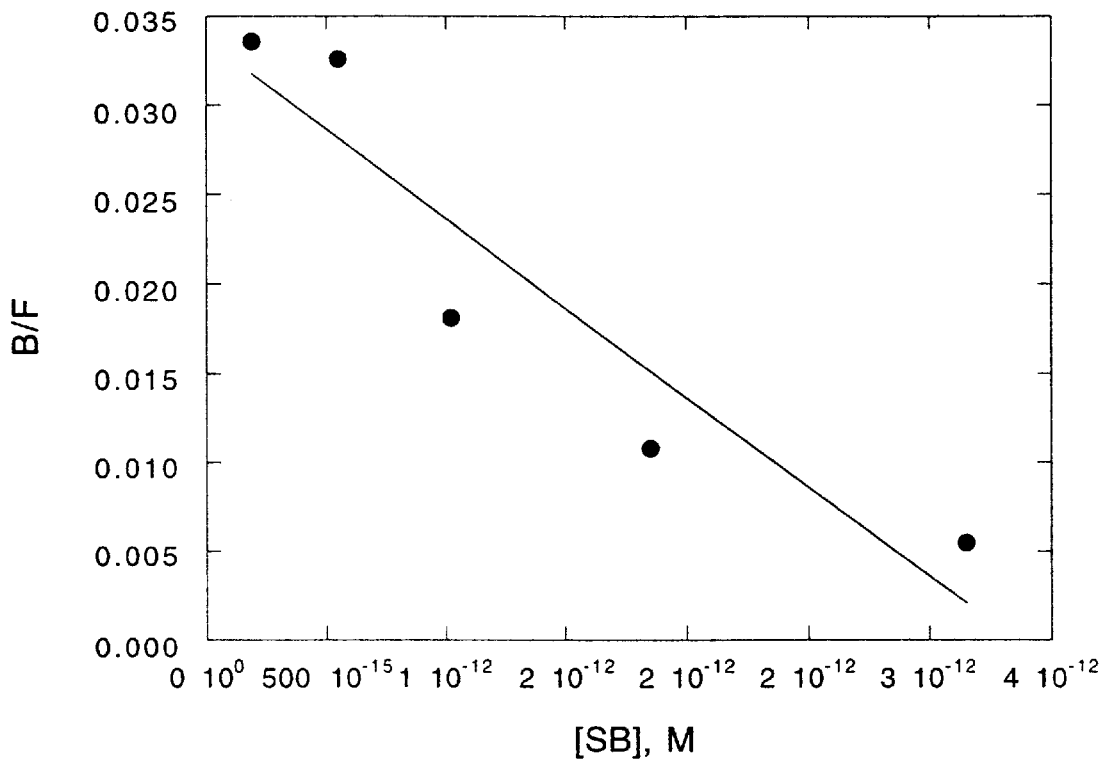
FIG. 10B is the Scatchard analysis of the data points shown in 10A for the SB curve.

In search of KGF receptors on the surface of PC-3 cells, different concentrations of $^{125}$I-hKGF were used, ranging from 0.002 to 0.8 nM, in the presence and absence of 100 fold molar excess of unlabeled hKGF, and saturation binding of the tracer on the surface of PC-3 cells was observed. FIG. 10 shows the plot of the concentration of bound tracer as a function of the total concentration of tracer as well as the Scatchard analysis of the same data. Analysis of the data suggested that there are about 5,000 specific hKGF binding sites per cell with a $K_D$ of 100–200 pM. This $K_D$ is in good agreement with the reported $K_D$ for hKGF of 200 pM (Miki et al., (1992) Proc natl Acad Sci USA 89:246–250).

Figure 11:
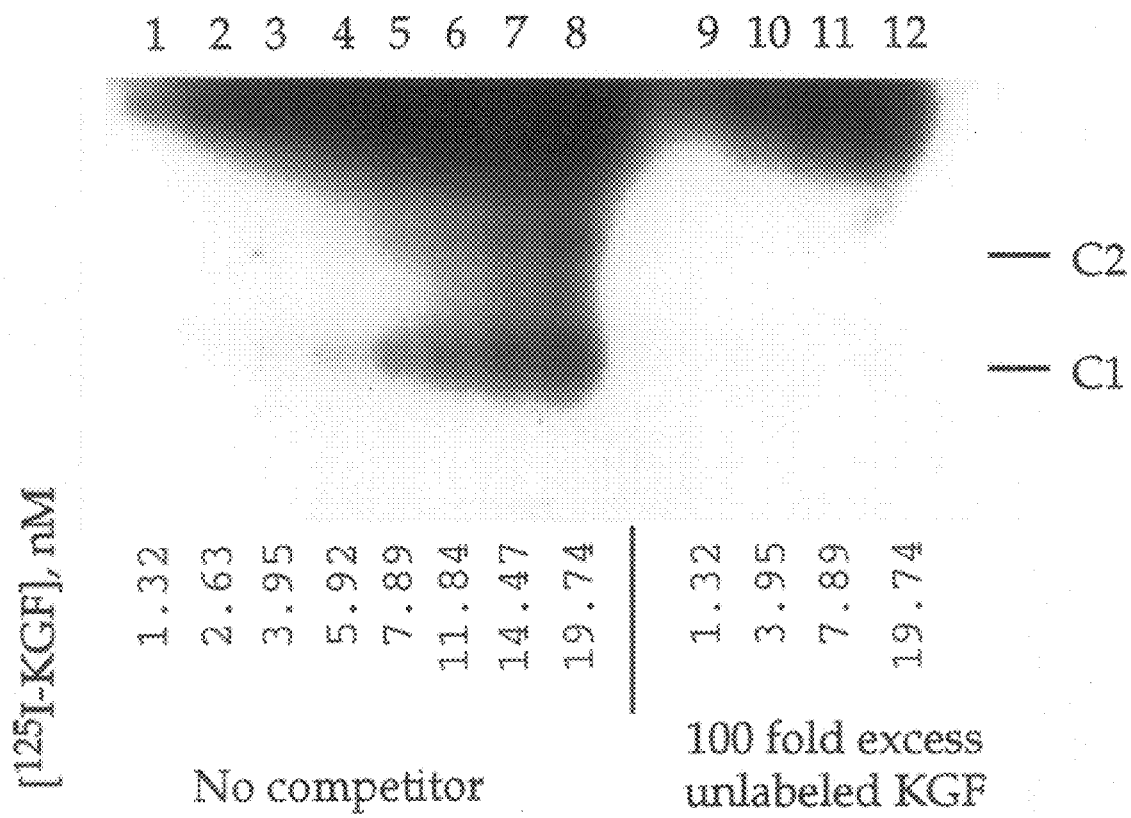
FIG. 11 shows the shift of the electrophoretic mobility due to plasma membrane extracts from PC-3 cells. In lanes 1–8, the membrane extracts were reacted with various concentrations of radiolabeled hKGF as shown under each lane. In addition to the radiolabeled hKGF (as shown under each lane) for lanes 9–12 a 100 fold molar excess was included of unlabeled hKGF. C1 and C2 represent two observed complexes due to the presence of hKGF binding moieties in the PC-3 plasma membrane extracts.

PC-3 plasma membrane extracts were found to alter the electrophoretic mobility (gel shift) of radiolabeled hKGF upon native gel electrophoresis (FIG. 11). For electrophoretic mobility shift gels, about $3 \times 10^7$ PC-3 cells were gently spun and washed with PBS and then lysed by mixing with equal volume of lysis buffer containing 40 mM Hepes, pH 7.4, 150 mM NaCl, 20% glycerol, 2% triton X-100, 0.1% sodium azide, 3 mM $MgCl_2$, 3 mM EGTA, 2 µM aprotinin, 2 µM leupeptin, 2 mM PMSF, and 400 µM sodium orthovanadate. Following 15 min incubation on ice the extract was spun at 11,000 g at 4° C. for 30 min to remove debris and nuclei and the supernatant was aliquoted and stored at −70° C. For gel analysis, 25 µl binding reactions were set in DPBS, 0.01% HSA, 2 mM $MgCl_2$, containing 3 µl of a 10 fold diluted PC-3 membrane extract in 0.01% HSA, and various concentrations of $^{125}$I-labeled hKGF. Following a 10 min incubation at room temperature, 6X loading dye was added to achieve 1X concentration, and the samples were loaded onto a 5% or 10% native TBE polyacrylamide gel. The gel was prerun at room temperature at 100 Volts. Following loading, the gel was run at 200 Volts for 5 min and then at 100 Volts for 30–60 min at room temperature. The radioactive bands were then visualized by autoradiography. The gel shift of radiolabeled hKGF is not observed in the presence of 100 fold molar excess of unlabeled hKGF (FIG. 11), demonstrating a specific interaction between a component found in the PC-3 membrane extracts and hKGF. The estimated KD from the gel shift experiment is about 8 nM.

In agreement with the competition experiments reported in the literature (Miki et al., Proc Natl Acad Sci USA 89:246–250), gel shift competition curves using unlabeled hKGF and bFGF as well as an unrelated small basic protein namely lysozyme were obtained. Table 21 lists the IC50 values obtained in this experiment. In agreement with previous reports, the data presented in Table 21 show that bFGF competes about 20 fold worse than hKGF for binding with the hKGF receptor present in the PC-3 plasma membrane extracts. The interaction observed by the gel shift appears to be a specific interaction for FGF and it is not due to a charge-charge interaction, as lysozyme, another small positively charged molecule, competes for the PC-3 membrane extract:hKGF complex with about 100 fold worse affinity than hKGF alone.

IC50 values for various RNA ligands obtained with the PC-3 assay are shown in Table 19. A subset of these ligands was tested on the NIH3T3/FGFR-2. Competitive inhibition constants (Ki) were determined from full competition curves and are summarized in Table 20. In determining the Ki values, it was assumed that 3T3 cells have 500,000 binding sites per cell and PC-3 cells have 5,000 binding sites per cell.

The data show that several hKGF ligands can competitively inhibit binding of hKGF to its cell surface receptors. Some of these ligands, such as K14F, have potent competitive activities with Ki's in the low nM range.

This work not only demonstrates that nucleic acid competitors for hKGF were obtained, but also identifies a new assay for screening hKGF competitors including small molecules, antibodies, and peptides. This new assay includes the use of the prostate carcinoma cell line, PC-3.

The two cell lines, PC3 and NIH3T3/FGFR-2, give slightly different results (see Table 20). KGF binding to PC-3 cells is more sensitive to inhibition by several ligands and by heparin. Random RNA, however, does not effectively compete for KGF binding on the PC-3 cells. KGF binding to NIH3T3/FGFR-2 is resistant to inhibition by some RNA ligands and heparin. This is because the NIH3T3/KGFR assay is more stringent since it is done in the presence of 1 µg/ml heparin. The random oligonucleotide competition curve with the NIH3T3/FGFR-2 is completely flat with $K_i > 10^{-4}$ M. Ligands 6F and 14F show the best inhibitory activity with $K_i$ values of 100–200 pM and 2–8 nM in the PC-3 and NIH3T3/FGFR-2 assay respectively. Only two 2'NH2 ligands, 14N and 29N, show good activity with the PC-3 cells ($K_i$ value of 1.4 nM). From these two ligands, only 14N retains its inhibitory activity in the NIH3T3/FGFR-2 assay showing a $K_i$ value of 100 nM. The observed inhibition of the KGF mitogenic activity by these ligands is not due to a nonspecific affect in the proliferative ability of the cell lines because these ligands have no antiproliferative activity on cells induced by EGF instead of KGF (data not shown).

This work not only demonstrates that nucleic acid competitors for hKGF were obtained, but also identifies a new assay for screening hKGF competitors including small molecules, antibodies, and peptides. This new assay includes the use of the prostate carcinoma cell line, PC-3.

Example 19

Inhibition of the Mitogenic Activity of KGE

One of the biological effects of KGF is the stimulation of proliferation of epithelial cells (Rubin et al., (1989) Proc Natl Acad Sci USA 86:802–806). This proliferative effect of KGF can be measured by the stimulation of $^3$H-thymidine incorporation in responding cells after exposure to KGF. Three such cell lines have been described before (Rubin et al., (1989) Proc Natl Acad Sci USA 86:802–806). Two cell lines were used to test the anti-mitogenic activity of various ligands. One is 4MBr-5 (ATCC #CCL208), a monkey epithelial, low passage, cell line (Caputo et al., (1979) In Vitro 15:222–223) while the second is Balb/MK, a transformed rat keratinocyte cell line (Weissman and Aaronson (1983) Cell 32:599–606). 4-MBr5 cells grown in F12K containing 30 ng/ml, hEGF, and 10% FCS, were trypsinized and resuspended in Ml99 containing 10 mM HEPES, pH 7.4, and 10 % FCS at 1.4×10$^5$ cells/ml. A 96-well microtiter plate was seeded with 100 μl of cell suspension and KGF was added at 10 ng/ml (0.5 nM), as well as K14F ligand at various concentrations ranging from 0–1000 nM. Each incubation reaction was set in at least triplicates. Following 24 h incubation at 37° C., $^3$H-thymidine was added at 1 μCi/well along with unlabeled thymidine at 10 nNM. The cells were incubated for additional 24 h, the supernatant was aspirated, and the remaining cells were harvested by lysis in 20 μl of 0.2 N NaOH. The extent of $^3$H-thymidine incorporation was determined by TCA precipitation and filtration through GFC filter disks (Whattnan, Hillsboro, Oreg.).

Balb/MK cells grown in Low Ca$^{++}$ EMEM with 10% FCS (dialyzed and heat inactivated) and 5 ng/ml rhEGF were trypsinized and resuspended in Low Ca$^{++}$ EMEM with 1% FCS (dialyzed and heat inactivated) and 0.5 ng/ml rhEGF and plated on 96 well fibronectin coated culture plates at 4–6×10$^4$ cells per well in 100 μl total volume. Following overnight growth, the medium was replaced with Low Ca$^{++}$ EMEM without FCS or rhEGF and serum starved for about 30 hrs. Human recombinant KGF or EGF was then added at 16 and 49 pM respectively, along with various concentrations of competitors ranging from 0–1000 nM. Following over-night incubation, $^3$H-thymidine was added at 0.2 μCi/well and incubation continued for an additional 7–8 hrs. The extent of $^3$H-thymidine incorporation was determined by TCA precipitation and filtration through GFC filter disks.

The inhibition constants ($K_i$) of the oligonucleotide ligands were determined by a nonlinear regression analysis of the data as described before (Gill et al., (1991) J. Mol. Biol. 220:307–324).

The two assays give slightly different results. The 4MBr-5 assay was performed in the presence of fetal calf serum, while the Balb/MK was done following serum starvation. The Balb/MK assay is more sensitive and a prototypic assay for the KGF induced mitogenic activity. Similar to the results obtained with the PC-3 cells, the 4MBr-5 assay showed a good activity for ligand 14F ($K_i$ value of 9.8 nM but incomplete inhibition). In the same assay, the random oligonucleotides showed $K_i$ values of >1 μM while a monoclonal neutralizing antibody showed a $K_i$ value of 2.9 nM. It appears that ligand 14F is as good or even better than the monoclonal neutralizing antibody. The competition curves for the neutralizing monoclonal antibody and ligand 14N plateau at about 20–40%, suggesting that these antagonists do not completely abolish the KGF mitogenic activity. In contrast to the monoclonal antibody, ligand 14F completely blocks the KGF mitogenic activity on the 4MBr-5 cells. In the Balb/MK assay, 14N showed $K_i$ values of about 10 nM (incomplete inhibition) while the random oligonucleotide showed $K_i$ values of about 300 nM. The $K_i$ values for 6F and 14F are 830 and 92 pM, respectively. Similar to the 4MBr-5 assay, ligand 14F appears to be as good if not better than the monoclonal neutralizing antibody which shows a $K_i$ value of 980 pM. The best inhibitory activity was observed with 14F3'T with a $K_i$ value of 34 pM.

Example 20

Nucleic acid ligands that bind to basic fibroblast growth factor (bFGF) have been derived by the SELEX method as described in U.S. Pat. No. 5,459,015 (see also U.S. Pat. No. 5,270,163 and Tuerk and Gold (1990) Science 249:505–510). A 2'NH$_2$-modified nucleic acid ligand designated 21A having the sequence 5'-GGGAGACAA-GAAUAACGCUCAAGUAGACUAAUGUGUGGAAGA-CAGCGGGUGGUUCGACAGGAGGCUCAC-AACAGGC (SEQ ID NO:265) was examined by deletion analysis for the minimal sequence information required for high affinity binding to bFGF. This analysis led to truncated ligand 21A-t (GGUGUGGAAGACAGCGGGUGGuuc (SEQ ID NO:266) where the underlined G's are guanines added to improve efficiency of transcription and lowercase letters are from the constant region.

In order to increase the stability of ligand 21A-t against degradation by nucleases, short phosphorothioate caps were added to the 5' and the 3' ends. In addition, nine ribopurine positions were identified that can be substituted with 2'-deoxy-2'-O-methylpurines without a loss in binding affinity for bFGF, using the method described in Green et al., Chem. Biol. 2:683–695, resulting in the ligand designated as NX-286 (5'-TsTsTsTs mGmGaU rGaUrG aUrGrG mArArG mAaCrA rGaCmG mGmGaU mOmGaU aUaC TsTsTsTsT-3' (SEQ ID NO:267), where s represents phosphorothioate internucleoside linkage, aU and aC are 2'-deoxy-2'-aminouridine and 2'-deoxy-2'-aminocytidine residues, respectively, mA and mG are 2'-deoxy-2'-O-methyladenosine and guanosine residues, respecitvely, rA and rG are adenosine and guanosine residues and T is 2'-deoxythymidine). The modified nucleic acid ligand had a $K_d$ of 0.4 nM as measured by electrophoretic mobility shift assay.

TABLE 1

Nucleic Acid Sequences Used in SELEX Experiments described in Examples 1–4

| | SEQ ID NO. |
|---|---|
| Starting RNAs: | |
| 64N6 transcript: 5' GGGGGAGAACGCGGAUCC [-64N-] AAGCUUCGCUCUAGAUCUCCCUUUAGU GAGGGUUA 3' | 1 |
| 40N6 transcript: | |

TABLE 1-continued

Nucleic Acid Sequences Used in SELEX Experiments described in Examples 1–4

| | SEQ ID NO. |
|---|---|
| 5' GGGGGAGAACGCGGAUCC [-40N-] AAGCUUCGCUCUAGAUCUCCCUUUAGU GAGGGUUA 3'<br>randomized lib2-6-1 transcript*:<br>5'GGGGGAGAACGCGGAUCC[ugucuccaccgccgauacuggggguuccuggggccccuccauggag gagggggugguucggaga]AAGCUUCGCUCUAGAUCUCCCUUUAGUGAGGGUUA 3'<br>Starting DNA templates: | 2<br><br>3 |
| Z-54 (64N60):<br>5'GGGAGAACGCGGATCC [-64N-] AAGCTTCGCTCTAGA3'<br>Z-55 (40N6):<br>5'GGGAGAACGCGGATCC [-40N-] AAGCTTCGCTCTAGA3'<br>D-123(randomized lib2-6-1)*:<br>5'GGGGGAGAACGCGGATCC[tgtctccaccgccgatactggggttcctggggcccctccatggaggaggg gggtggttcggaga]AAGCTTCGCTCTAG 3'<br>PCR and cloning primers: | 4<br><br>5<br><br>6 |
| T7SacBam:<br>5'TAATACGACTCACTATAGGGG<u>GAGTCT</u>GC<u>GGATCC</u>3'<br>                                    SacI       BamH1<br>T7SB2N:<br>5'TAATACGACTCACTATAGGGGGAGAACGC<u>GGATCC</u>3'<br>                                              BamH1<br>3XH:<br>5'TAACCCTCACTAAAGGGAGA<u>TCTAGA</u>GC<u>AAGCTT</u>3'<br>                                XbaI      HindIII<br>BamH1 cloning site engineered into DGem9zf to clone SELEX experiments 3–9. | 7<br><br><br>8<br><br><br>9 |
| <u>GATTTAGGTGACACTATAGAATAT</u>GCATCACTAGTAAGCTTTGC<u>TCTAGA</u><br>    SP6 promoter                                         XbaI<br><u>GGATCCCGGA</u><u>GCTCCCTATAGTGAGTCGTATTA</u><br>BamH1        T7 promoter | 10<br><br>11 |

*GAUC or GATC, these bases only
gauc or gact 62.5% specified base, 12.5% the other three bases

TABLE 2

RNA SELEX Experiments described in Examples 1–4: template, pyrimidine nucleotides, and round cloned.

| SELEX exp | template* | 2'substitued UTP | 2'substituted CTP | Round cloned |
|---|---|---|---|---|
| lib1 | 64N6 | OH | OH | 20 |
| lib2 | 64N6 | OH | OH | 6 |
| lib3 | 40N6 + 64N6 | F | F | 4 |
| lib4 | 40N6 + 64N6 | NH$_2$ | NH$_2$ | 5 |
| lib5 | 64N6 | NH$_2$ | NH$_2$ | 13 |
| lib6 | 64N6 | F | F | 13 |
| lib7 | 64N6 | F | NH$_2$ | 14 |
| lib8 | D-123 | OH | OH | 6 |
| lib9 | 64N6 | NH$_2$ | F | 5 |

*Sequences of templates are described in Table 1.

TABLE 3

TGFb Binding ligands

| clone | 5'CONSTANT | VARIABLE | 3'CONSTANT | SEQ ID NO. |
|---|---|---|---|---|
| Group A | gggggagaacgcggaucc | [40 OR 64N] | aagcuucgcucuagaucucccuuuagugagaggguua | 2 or 1 |
| lib3 | | | | |

TABLE 3-continued

TGFb Binding ligands

```
13  GAGCAAUCCCAGGCGCAUAGCUUCCGAGUAGACAGGAGGGAGGGUGGAUGUGGCGUCUACUCGGUGUCGUG      12
3   GAGCAACCCCAGGCGCAUAGCUUCCGAGUAGACAGGAGGGAGGGUGGAUGUGGCGUCUACUCGGUGUCGUG      13
4   GAGCAACCCCAGGCGCAUAGCUUCCGAGUAGACAGGCGGGAGGGGUGGAUGUGGCGUCUACUCGGAGUCGUG     14 lib4
32  G GCAACCCCAGGCGCAUAGCUUCCGAGUAGACAGGCGGGAGGGGUGGAUGUGGCGUC ACGAGG            15 lib8
9    GCAAUCCCAGGCGCAUAGCUUCCGAGUAGACAGGAGGGAGGGGUGGAUGUGGCGUCUACUCGGCGUCGUG      16 lib5
5   GAGCAAUCCCAGGCGCAUAGCUUCCGAGUAGACAGGAGGGAGGGGUGGAUGUGGCGUCU CGAGG            17
7   GAGCAAGCCCUGGC  AUAGCUUCCGAGUAGACAGGAGGGAGGGGUGGAUGUGGCGUCUACUCGGUGUCGUG     18
48  G GCAAUCCCAGGCGCAUAGCUUCCGAGUAGACAGGAGGGAGGGGUGGAUGUGGUGU ACGAGG             19 lib2
6-4 GAGCAAUCCCAGGCGCAUAGCUUCCGAGUAGACAGGAGGGAGGGGUGGAUGUGGUGUCU CGAG            20 lib6
23              A AGCUUC GAGUAGACAGGAGGGAGGGGUGGAUGUGGAGUCU CGAG                 21
4   GAGCAAUCCUAA   GCAUAGCUUC GAGUAGACAGGAGGGAGGGGUGGAUGUGGCGUCU CGAG           22 lib7
21  GAGCAAUCCCGGGCGCAUAGCUUCCGAGGAGACAGGCGGGAGGGGUGGAUGUGGCGUCU CGAG             23
43  GAGCAAUCCCAGGCGCAUAGCUUCCGAGUAGACAGGCGGGAGGGGUGGAUGUGGCGUCU CGAG             24 gggggagaacgcggaucc [40 OR 64N] aagcuucgcucuagaucucccuuuagugagggguua   2 or 1
Group B.

lib4-12  UGAGAAGGACGUCGGGGUCAACGGGGUGAGGUGCAGCAGAAAGGGCCGGCACCACAUGACGUAA            28
lib3-44  UGAGAAGGACGUCGGGGU          GAGGUGCAGCAGAAAGGGCCGGCACCACAUGACGUAA         29
lib3-42  GGUGGGAAA GUCGGAUU          AUGUGU GUAGAUUU GU  GUGCGA                   30

Group C.

lib1-20-3**   UGCUAGACCGAGGAUGCAAAGGGACAUGCAUUAGGGAAACCUAUGUAUAAGAACGCGGUCGCAG           32
lib1-20-3H**  UGCUAGACCGAGGAUGCAAAGGGACAUGCAUUAGGGAAACCUAUGUAUAAGAACGCGGUCGCAGA          33
lib6-30**     UGCUAGACCGAGGAUGCAAAGGGACAUGCAUUAGGGAAACCUAU UAUAAGAACGCGGUCGCAG           34

Group D.

lib2-6-1*     UGUCUCCACCGCCGAUACUGGGGUUCCUGGGGCCCCUCCAUGCAGGAGGGGGGUGGUUCGGAGA           35
lib2-6-1-81*  UGUCUCCACCGCCGAUACUGGGGUUCCUGGGGCCCCUCCAUGCAGGAGGGGGGUGGUUCGGAG            36
lib8-23*      UGUCUCCACCGCCGAUACUGGGGUUCCUGGGGCCGCUCCAUGCAGGAGGGGGGUGGUUCGGAGA           37
lib9-10*      UGUCUCCACCGCCGAUACUGGGGUUCCUGGGGCCCCUCCAUGCAGGAGGGGUGGUUCGGAGA             38

ORPHANS.
clone# lib3-45        GGAAGUCUGGUCUUUGGGGAGUCCGCAUGGCCCUGGCGA                                   39
lib1-20-5**    AAGAAUGUUCGGCCGCACGAGGUGACAGUGGUGCGGAUACGGACCGAUUGGGUUUGCC                 40
lib1-20-12***  GGUCACCCGGGCAUAUAACAAUGCCGACACUGGGGUACCUGGGACGGGUGGGACUGGACGGAAG           41
lib2-6-8***    AUAACCGGCUGCAUGGGAGGGACAUCCUGGGAAAGGACGGGUCGAGAUGACCUGAGCAGUUCCGGC         42 clone                                                                                  SEQ ID
```

Group A Boundary Experiments

```
lib3-13 boundaries  5' GCUUCCGAGUAGACAGGAGGGAGGGGUGGAUGUGGCGUCUAC 3'                    25
lib8-9  boundaries  5'  CUUCCGAGUAGACAGGAGGGAGGGGUGGAUGUGGCGUCUACUC 3'                26
lib4-32 boundary       GGCAACCCCAGGCGCAUAGCUUCCGAGUAGACAGGCGGGAGGGGUGGAUGUGGCGUCACG 3'  27
```

Group B Boundary Experiments

```
lib4-12 boundaries 5' UGAGAAGGACGUCGGGGUCAACGGGGUGAGGUGCAGCAGAAAGGGCCGGCACCA 3'      31
```

Legend: The constant region of the ligand is shown in lower case and variable in upper.
Sequences have been aligned. Deletions with respect to the first sequence in each group are
shown by gaps, substitutions are in bold type.
*2'NH2-UTP, 2'F-CTP:
**2'F-UTP, 2'F-CTP.
***2'OH-UTP, 2'OH-CTP
Group A and B bind with either 2'NH2- or 2'F- pyrimidines.
Ligands bind with either 2'NH2- or 2'F- pyrimidines unless otherwise indicated.

TABLE 4

Dissociation and Inhibition Constants

| Group | Ligand | $B_{max}$ | $K_d$ | $IC_{50}$ |
|---|---|---|---|---|
| A | lib3-13 | 0.60 | 0.9 nM | 9.7 nM |
|  |  | 0.38 | 0.7 nM | 42 nM |
|  |  | 0.55 | 0.9 nM | 18 nM |
|  |  |  |  | 32 nM |
|  | lib3-3 | 0.44 | 1.7 nM | NT |
|  | lib4-32 | 0.50 | 0.8 nM | 20 nM |
|  |  |  |  | 157 nM |
|  | lib5-5 | 0.37 | 2.4 nM | 49 nM |
|  | lib5-7 | 0.33 | 3.4 nM | 17 nM |
|  | lib8-9 | 0.4 | 1.7 nM | 210 nM |
|  | lib8-9* | 0.35 | 2.8 nM | 124 nM |
|  | lib8-48 | 0.32 | 3.8 nM | not inhibitory |
|  | lib2-6-4 | 0.20 | 3.1 nM | not inhibitory |
|  | lib6-23 | 0.35 | 3.4 nM | not inhibitory |
|  | lib7-21**** | 0.18 | 2.4 nM | not inhibitory |
|  | lib7-43**** | 0.33 | 3.3 nM | not inhibitory |
| B | lib4-12 | 0.15 | 0.4 nM | 109 nM |
|  |  | 0.08 | 0.2 nM | 108 nM |
|  |  |  |  | 69 nM |
|  | lib3-44 | 0.18 | 1.3 nM | 119 nM |
|  | lib3-42 | 0.16 | 0.6 nM | 22 nM |
| C | lib1-20-3** | 0.67 | 30 nM | not inhibitory |
|  | lib1-20-3-82** | 0.46 | 6.1 nM | not inhibitory |
|  | lib6-30** | 0.35 | 8.8 nM | not inhibitory |
| D | lib2-6-1* | 0.40 | 14.3 nM | 112 nM |
|  |  |  |  | 103 nM |
|  | lib2-6-1-81* | 0.39 | 10.7 nM | 201 nM |
|  |  |  |  | 298 nM |
|  | lib8-23* | 0.48 | 6.6 nM | not inhibitory |
|  | lib9-10* | 0.24 | 1.1 nM | not inhibitory |
| Orphans | lib3-45 | 0.08 | 1.9 nM | not inhibitory |
|  | lib1-20-5** | 0.42 | 46 nM | not inhibitory |
|  | lib1-20-12*** | 0.34 | 3.1 nM | NT |
|  | lib1-6-8*** | 0.12 | 4.7 nM | NT |
| Controls | lib5-9 |  | nonbinder | not inhibitory |
|  | random 64N6 |  | nonbinder | not inhibitory | ligands are 2'-NH2 pyrimidines unless otherwise noted
*2'-NH2-UTP, 2'-F-CTP,
**2'-F pyrimidines,
***2'-OH pyrimidines,
****2'-F-UTP, 2'-NH2-CTP

TABLE 5

DNA oligonucleotides used in Examples 5 and 6[a]

| Description | Sequence | SEQ ID NO. |
|---|---|---|
| 40N7 Template for RNA SELEX | TCGGGCGAGTCGTCTG[40N]CCGCATCGTCCTCCC | 43 |
| 5N7 5'-primer for PCR | TAATACGACTCACTATAGGGAGGACGATGCGG | 44 |
| 3N7 3'-primer for PCR | TCGGGCGAGTCGTCTG | 45 |
| 40D7 Starting material for DNA SELEX | GGGAGGACGATGCGG[40N]CAGACGACTCGCCCGA | 46 |
| 5D7 5'-primer for PCR | GGGAGGACGATGCGG | 47 |
| 3D7 3'-primer for PCR | (biotin)₃TCGGGCGAGTCGTCTG | 48 |
| 40N8 Template for RNA SELEX | GCCTGTTGTGAGCCTCCTGTCGAA[40N]TTGAGCGTTTATTCTTGTCTCCC | 49 |
| 5N8 5'-primer for PCR | TAATACGACTCACTATAGGGAGACAAGAATAAACGCTCAA | 50 |
| 3N8 3'-primer for PCR | GCCTGTTGTGAGCCTCCTGTCGAA | 51 |
| 40D8 Starting material for DNA SELEX | GGGAGACAAGAATAAACGCTCAA[40N]TTCGACAGGAGGCTCACAACAGGC | 52 |
| 5D8 5'-primer for PCR | GGGAGACAAGAATAAACGCTCAA | 53 |
| 3D8 3'-primer for PCR | (biotin)₃GCCTGTTGTGAGCCTCCTGTCGAA | 54 |

[a]DNA oligonucleotides 40N7 and 40N8 were used to generate the double-stranded DNA template for in vitro transcription. The 3'-primers 3N7 and 3N8 were also used to generate cDNA from the RNA repertoire. Synthetically synthesized DNA oligonucleotides 40D7 and 40D8 were used directly as the starting repertoire for the two single-stranded DNA SELEX experiments. PCR amplification of the selected repertoires used the appropriate 5'- or 3'-primer. The symbol 40N indicated a 40-nucleotide randomized region within the oligonucleotide.

TABLE 6

TGFβ1 40N7 DNA Selex Sequence of fifty randomly chosen clones.

| | | SEQ ID NO. |
|---|---|---|
| 5' GGGAGGACGATGCGG...40N...CAGACGACTCGCCCGA 3' | | 46 |
| Group A | | |
| 20(11 clones) CCAGGGGGGGTATGGGGGTGGTGCTACTTACTTGCGTCTT | | 55 |

TABLE 6-continued

TGFβ1 40N7 DNA Selex Sequence of fifty randomly chosen clones.

| | | SEQ ID NO. |
|---|---|---|
| 4 | CCAGGGGGGTATGGGGGTAGTGCTACTTACTTGCGTCTT | 56 |
| 5 | CCAGGGGGGTATGGGGGTAGTACTACTTACTTACGTCTT | 57 |
| 8 | CCAGGGGGGTATGGGGGTATACTACTTACTTACGTCTT | 58 |
| 13 | CCAGGGGGGTATGGGGGTAATACTACTTACTTACATCTT | 59 |
| 16 | CCAGGGGGGTATGGGGGTAATACTACTTACTTACGTCTT | 60 |
| 40 | CCAGGGGGGTATGGGGGTGGTGTTACTTACTTGCGTCTT | 61 |
| 48 | CCAGGGGGGTATGGGGGTGGTGCTTCTTACTTGCGTCTT | 62 |

Group B

| | | |
|---|---|---|
| 18 | CCAGGGGGGTATGGGGGTGGTGTACTTTTTCCTGCGTCTTC | 63 |
| 19 | CCAGGGGGGTATGGGGGTGGTTCGTTTTTCTTTGCGGCTT | 64 |
| 32 | CCAGGGGGGTGTGGGGGTGGTGTACTTTTTCTTGTCTTC | 65 |
| 46 | CCAGGGGGGTATGGGGGTGGTTTGGTATGTTGCGTCCGT | 66 |

Group C

| | | |
|---|---|---|
| 12(3 clones) | CCGGGGTGGGTATGGGGGTAATACTACTTACTTACGTCTT | 67 |
| 1 | CCGGGGGTGGGTAGGGGGGTAGTGCTACTTACTTACGTCTT | 68 |
| 3 | CCAGGGTCGGTGTGGGGTAGTACTACTTACTTGCGTCTT | 69 |
| 10 | CCAGGGTGGGTATGGGGGTAGTGCTACTTACTTGCGTCTT | 70 |
| 23 | CCGGGGTGGGTATGGGGGTGGTGCTACTTACTTGCGTCTT | 71 |
| 34 | CCTGGGTGGGTATGGGGGTGGTGCTACTTACTTGCGTCTT | 72 |

Group D

| | | |
|---|---|---|
| 2 | CCACGGGTGGGTGTGGGGTAGTGTGTCTCACTTTACATCAC | 73 |
| 6 | CCCGGGGTGGGTGTGGGGTAGTGTATTATATTTACAGCCT | 74 |
| 25 &38 | CCAGGGTCGGTGTGGGGTGGTGTACTTTTCCTGTCCTTC | 75 |
| 7 | CCAGGGTCGGTATGGGGTAGTGTACTTTTTAATGATCTTC | 76 |
| 9 | CCCGGGGGAGAGCGGTGGGTAGTGTTCTATAGTATTCGTGT | 77 |
| 11 | CCAGGGGGGTATGTTTTTAATACTACTTACTTACGTCTT | 78 |
| 17 | CCAGGGAGGGTATGGGGGTGGTGTTTCTAGTTTTGCGGCGT | 79 |
| 21 | CCAGGGTGGGCATGGGGGTGGTGTGGATTAATTCTTCGTCC | 80 |
| 24 | CCAGGGTCGGTGTGGGGTGGTGTTTTTATTTACTCGTCGC | 81 |
| 28 &30 | GGGGCGGCTTGGAAGAGGTTGCCGGTTGGAGTATTCGAGC | 82 |
| 29 | CCAGGTGTGGGGTGGTTTGGGTTTTCTTTCGTCGCC | 83 |
| 31 | CCAGGGTGGGTATGGGGGTTTAATTAATTCTTCGTCCCA | 84 |
| 35 | GGGGCGGCTTGGAAGAGGTTGCCGGTTGGAGTATTCGAGC | 85 |
| 36 | CCCGGGGTGGGTGTGGGTGGTGTGAATTAATTCTTCGTCC | 86 |
| 41 | CCCGGGGTGGGTGTGGGGTGGTGTATTATATTTGCGGCCT | 87 |
| 44 &45 | CCAGGGTCGGTGTGGGTGGTGTACTTTTTCCTGTCCTTC | 88 |
| 50 | GGGGCGGCTTGGAAGAGGTTGCCGGTTGGAGTATTCGAGC | 89 |

Bold typeface indicates a discrepancy with the most common sequence of that group.

TABLE 7

Starting DNA and PCR primers for the ssDNA SELEX experiment

| | SEQ ID NO. |
|---|---|
| Starting ssDNA:<br>5'-ATCCGCCTGATTAGCGATACT[-40N-]ACTTGAGCAAAATCACCTGCAGGGG-3' | 90 |
| PCR Primer 3N2*:<br>5'-BBBCCCCTGCAGGTGATTTTGCTCAAGT-3' | 91 |
| PCR Primer 5N2**:<br>5'-CCGAAGCTTAATACGACTCACTATAGGG<u>ATCCGCCTGATTAGCGATACT</u>-3' | 92 |

*B = biotin phosphoramidite (e.g., Glen Research, Sterling, VA)
**For rounds 10, 11, and 12, the truncated PCR primer 5N2 (underlined) was used to amplify the template.

TABLE 8

Unique Sequences of the ssDNA high affinity ligands to PDGF

| | | SEQ ID NO |
|---|---|---|
| | 5'-ATCCGCCTGATTAGCGATACT [40N] ACTTGAGCAAAATCACCTGCAGGGG-3' | 90 |
| *14 | AGGCTTGACAAAGGGCACCATGGCTTAGTGGTCCTAGT | 93 |
| *41 | CAGGGCACTGCAAGCAATTGTGGTCCCAATGGGCTGAGT | 94 |
| 6 | CCAGGCAGTCATGGTCATTGTTTACAGTCGTGGAGTAGGT | 95 |
| 23 | AGGTGATCCCTGCAAAGGCAGGATAACGTCCTGAGCATC | 96 |
| 2 | ATGTGATCCCTGCAGAGGGAGGANACGTCTGAGCATC | 97 |
| 34 | CACGTGATCCCATAAGGGCTGCGCAAAATAGCAGAGCATC | 98 |
| 8 | GGTGGACTAGAGGGCAGCAAACGATCCTTGGTTAGCGTCC | 99 |
| 1 | GGTGCGACGAGGCTTACACAAACGTACACGTTTCCCCGC | 100 |
| 5 | TGTCGGAGCAGGGCGTACGAAAACTTTACAGTTCCCCCG | 101 |
| *40 | AGTGGAACAGGGCACGGAGAGTCAAACTTTGGTTTCCCCC | 102 |
| 47 | GTGGGTAGGGATCGGTGGATGCCTCGTCACTTCTAGTCCC | 103 |
| 18 | GGGCGCCCTAAACAAAGGGTGGTCACTTCTAGTCCCAGGA | 104 |
| 30 | TCCGGGCTCGGGATTCGTGGTCACTTTCAGTCCCGGATATA | 105 |
| *20 | ATGGGAGGGCGCGTTCTTCGTGGTTACTTTTAGTCCCG | 106 |
| 35 | ACGGGAGGGCACGTTCTTCGTGGTTACTTTTAGTCCCG | 107 |
| 13 | GCTCGTAGGGGCGATTCTTTCGCCGTTACTTCCAGTCCT | 108 |
| 16 | GAGGCATGTTAACATGAGCATCGTCTCACGATCCTCAGCC | 109 |
| *36 | CCACAGGCTACGGCACGTAGAGCATCACCATGATCCTGTG | 110 |
| 50 | GCGGGCATGGCACATGAGCATCTCTGATCCCGCAATCCTC | 111 |
| 4 | ACCGGGCTACTTCGTAGAGCATCTCTGATCCCGGTGCTCG | 112 |
| 44 | AAAGGGCGAACGTAGGTCGAGGCATCCATTGGATCCCTTC | 113 |
| 24 | ACGGGCTCTGTCACTGTGGCACTAGCAATAGTCCCGTCGC | 114 |
| 7 | GGGCAGACCTTCTGGACGAGCATCACCTATGTGATCCCG | 115 |
| *26 | AGAGGGAAGTAGGCTGCCTGACTCGAGAGAGTCCTCCCG | 116 |
| 19 | AGGGGTGCGAAACACATAATCCTCGCGGATTCCCATCGCT | 117 |
| 48 | GGGGGGGCAATGGCGGTACCTCTGGTCCCCTAAATAC | 118 |
| 46 | GCGGCTCAAAGTCCTGCTACCCGCAGCACATCTGTGGTC | 119 |
| 25 | TTGGGCGTGAATGTCCACGGGTACCTCCGGTCCCAAAGAG | 120 |
| 31 | TCCGCGCAAGTCCCTGGTAAAGGGCAGCCCTAACTGGTC | 121 |
| 12 | CAAGTTCCCCACAAGACTGGGGCTGTTCAAACCGCTAGTA | 122 |
| 15 | CAAGTAGGGCGCGACACACGTCCGGGCACCTAAGGTCCCA | 123 |
| *38 | AAAGTCGTGCAGGGTCCCCTGGAAGCATCTCCGATCCCAG | 124 |

* Indicates a boundary experiment was performed.
Italics indicate the clones that were found to retain high affinity binding as minimal ligands.

TABLE 9

```
                                      HELIX I
                            ┌─────────────────────────────────────────┐
                                  HELIX II          HELIX III
                            ┌───────────────┐   ┌────────────────┐
SEQ ID NO:   Group A
    97          2                       =AGGG---AGGA--TACG------TCTG-AGC-ATCac3'  5'ATGTGAT-CCCTGCAG=
   112          4                     ACCGGG---CTAC--TTC-------GTAG-AGC-ATC----TCT-----GAT-CCCGGTGCTCG
                                                A
   115          7                       tGGG---CGACC-TTCT-----GGACG-AGC-ATCAC--CTAT--GTGAT-CCCG
   109         16                     ctGAGG---CATG--TTAA------CATG-AGC-ATCGT--CTC---ACGAT-CCTCAGCC
   110         36                    CCACAGG---CTACG-GCA------CGTAG-AGC-ATCA---CCA----TGAT-CCTGTG
   124         38              AAAGTCGTGCAGGG---TCC---CCT--------GGA-AGC-ATC----TCC-----GAT-CCCAGactt
   113         44                     AAAGGG---CGAAC-GTA------GGTCG-AGGCATCC---ATT----GGAT-CCCTTC
   111         50                      GCGGG---CATG--GCA-------CATG-AGC-ATC----TCT-----GAT-CCCGCAATCCTC
    96         23                        =AGG---CAGGATAAC-----GTCCTG-AGC-ATCac3'  5'AGGTGATCCCTGCAA=
    98         34                        =GGG---CTGC--GCAAAATA-GCAG-AGC-ATCac3'  5'CACGTGAT-CCCATAA=
             Group B
   108         13                     GCTCGTAGG--GGGCGA-TTCTT----TCGCC-GTT-ACT----TCC-----AGT-CCTac
    93         14                     tactAGG---CTT---GACA-------AAG-GGC-ACCAT--GGCTTAGTGGT-CCTAGTa
                                                C
   123         15                  ctCAAGTAGGG---CGGAC-ACAC-----GTCCG-GGC-ACC----TAA-----GGT-CCCAacttgag
   104         18                      ctGGG---CGCCCTAAACAA--AGGGTG-GTC-ACT----TCT-----AGT-CCCAGGA
   106         20                    ATGGGAGGG---CGCG--TTCTT-----CGTG-GTT-ACT----TTT-----AGT-CCCG
   120         25                      ctTTGGG---CGTG--AATGTC----CACG-GGT-ACC----TCC-----GGT-CCCAAAGAG
   105         30                      TCCGGG---CTCGG-GAT------TCGTG-GTC-ACT----TTC-----AGT-CCCGGATATA
   121         31                                                        5'TCCGCGCAAGT-CCCTGGTAA=
                                         =AGGG---CAG---CCCTAA-----CTG-GTC-acttgagc3'
   107         35                     ACGGGAGGG---CACG--TTCTT-----CGTG-GTT-ACT----TTT-----AGT-CCCG
    94         41                        =GGG---CTGAGTa3'  5'tactCAG-GGC-ACTGCAAGCAATTGTGGT-CCCAAT=
                                              A       T
   103         47                    GTGGGTGGGATCGGGG--ATG-------CCTC-GTC-ACT----TCT-----AGT-CCCact
```

TABLE 10

Frequency of base pairs in the helical regions of the consensus motif shown in FIG. 3

| Position[a] | Base pair[b] | | | | | | |
|---|---|---|---|---|---|---|---|
| | AT | TA | GC | CG | TG | GT | other |
| I-1 | 0 | 0 | 21 | 0 | 0 | 0 | 0 |
| I-2 | 0 | 0 | 21 | 0 | 0 | 0 | 0 |
| I-3 | 5 | 0 | 16 | 0 | 0 | 0 | 0 |
| I-4 | 3 | 5 | 1 | 4 | 1 | 0 | 7 |
| I-5 | 2 | 3 | 3 | 4 | 0 | 0 | 9 |
| II-1 | 0 | 1 | 2 | 17 | 0 | 0 | 1 |
| II-2 | 5 | 5 | 5 | 1 | 0 | 4 | 1 |
| II-3 | 3 | 4 | 7 | 6 | 0 | 0 | 1 |
| II-4 | 3 | 0 | 8 | 5 | 0 | 0 | 4 |
| III-1 | 21 | 0 | 0 | 0 | 0 | 0 | 0 |
| III-2 | 0 | 10 | 0 | 11 | 0 | 0 | 0 |
| III-3 | 0 | 7 | 0 | 13 | 1 | 0 | 0 |

[a]Helices are numbered with roman numerals as shown in FIG. 3. Individual base pairs are numbered with arabic numerals starting with position 1 at the helix junction and increasing with increased distance from the junction.
[b]We have included the TG and GT base pairs to the Watson-Crick base pairs for this analysis. There is a total of 21 sequences in the set.

TABLE 11

Affinities of the minimal DNA ligands to PDGF AA, PDGF AB and PDGF BB

| Ligand | $K_d$, nM | | |
|---|---|---|---|
| | PDGF AA[a] | PDGF AB[b] | PDGF BB[b] |
| 20t | 47 ± 4 | 0.147 ± 0.011 | 0.127 ± 0.031 |
| 36t | 72 ± 12 | 0.094 ± 0.011 | 0.093 ± 0.009 |
| 41t | 49 ± 8 | 0.138 ± 0.009 | 0.129 ± 0.011 |

[a]Data points shown in FIG. 5A were fitted to eq 1 (Example 7).
[b]Data points in FIGS. 5B and 5C were fitted to eq. 2. The dissociation constant ($K_d$) values shown are for the higher affinity binding component. The mole fraction of DNA that binds to PDGF AB or PDGF BB as the high affinity component ranges between 0.58 to 0.88. The $K_d$ values for the lower affinity interaction range between 13 to 78 nM.

TABLE 12

Starting RNA and PCR primers for the 2'-fluoropyrimidine RNA SELEX experiment

| Starting 2'-fluoropyrimidine RNA: | SEQ ID NO |
|---|---|
| Starting RNA:<br>5'-GGGAGACAAGAAUAACGCUCAA[-50 N-]UUCGACAGGAGGCUCACAACAGGC-3'<br>PCR Primer 1: | 125 |

TABLE 12-continued

Starting RNA and PCR primers for the 2'-fluoropyrimidine RNA SELEX experiment

| Starting 2'-fluoropyrimidine RNA: | SEQ ID NO |
|---|---|
| 5'-TAATACGACTCACTATAGGGAGACAAGAATAACGCTCAA-3' | 126 |
| PCR Primer 2: | |
| 5'-GCCTGTTGTGAGCCTCCTGTCGAA-3' | 127 |

TABLE 13

Sequences of the 2'-fluoropyrimidine RNA high affinity ligands to PDGF AB.

| | | SEQ ID NO. |
|---|---|---|
| 1 | CGGUGGCAUUUCUUCACUUCCUUCUCGCUUUCUCGCGUUGGGCNCGA | 128 |
| 2 | CCAACCUUCUGUCGGCGUUGCUUUUUGGACGGCACUCAGGCUCCA | 129 |
| 3 | UCGAUCGGUUGUGUGCCGGACAGCCUUAACCAGGGCUGGGACCGAGGCC | 130 |
| 4 | CUGAGUAGGGGAGGAAGUUGAAUCAGUUGUGGCGCCUCUCAUUCGC | 131 |
| 5 | CAGCACUUUCGCUUUUCAUCAUUUUCUUUCCACUGUUGGGCGCGGAA | 132 |
| 6 | UCAGUGCUGGCGUCAUGUCUCGAUGGGGAUUUUUCUUCAGCACUUUGCA | 133 |
| 7 | UCUACUUUCCAUUUCUCUUUUCUUCUCACGAGCGGGUUUCCAGUGAACCA | 134 |
| 8 | CGAUAGUGACUACGAUGACGAAGGCCGCGGGUUGGAUGCCCGCAUUGA | 135 |
| 10 | GUCGAUACUGGCGACUUGCUCCAUUGGCCGAUUAACGAUUCGGUCAG | 136 |
| 13 | GUGCAAACUUAACCCGGGAACCGCGCGUUUCGAUCGACUUUCCUUUCCA | 137 |
| 15 | AUUCCGCGUUCCGAUUAAUCCUGUGCUCGGAAAUCGGUAGCCAUAGUGCA | 138 |
| 16 | CGAACGAGGAGGGAGUGGCAAGGGAUGGUUGGAUAGGCUCUACGCUCA | 139 |
| 17 | GCGAAACUGGCGACUUGCUCCAUUGGCCGAUAUAACGAUUCGGUUCAU | 140 |
| 18 | CGAACGAGGAGGGAGUCGCAAGGGAUGGUUGGAUAGGCUCUACGCUCAA | 141 |
| 19 | CGAGAAGUGACUACGAUGACGAAGGCCGCGGGUUGAAUCCCUCAUUGA | 142 |
| 20 | AAGCAACGAGACCUGACGCCUGAUGUGACUGUGCUUGCACCCGAUUCUG | 143 |
| 21 | GUGAUUCUCAUUCUCAAUGCUUUCUCACAACUUUUUCCACUUCAGCGUGA | 144 |
| 22 | AAGCAACGAGACUCGACGCCUGAUGUGACUGUGCUUGCACCCGAUUCU | 145 |
| 23 | UCGAUCGGUUGUGUGCCGGACAGCUUUGACCAUGAGCUGGGACCGAGGCC | 146 |
| 24 | NGACGNGUGGACCUGACUAAUCGACUGAUCAAAGAUCCCGCCCAGAUGGG | 147 |
| 26 | CACUGCGACUUGCAGAAGCCUUGUGUGGCGGUACCCCCUUUGGCCUCG | 148 |
| 27 | GGUGGCAUUUCUUCAUUUUCCUUCUCGCUUUCUCCGCCGUUGGGCGCG | 149 |
| 29 | CCUGAGUAGGGGGGAAAGUUGAAUCAGUUGUGGCGCUCUACUCAUUCGCC | 150 |
| 30 | GUCGAAACUGGCGACUUGCUCCAUUGGCCGAUAUAACGAUUCGGUUCA | 151 |
| 31 | GCGAUACUGGCGACUUGCUCCAUUGGCCGAUAUAACGAUUCGGCUCAG | 152 |
| 32 | ACGUGGGGCACAGGACCGAGAGUCCCUCCGGCAAUAGCCGCUACCCCACC | 153 |
| 33 | CACAGCCUNANAGGGGGGAAGUUGAAUCAGUUGUGGCGCUCUACUCAUUCGC | 154 |
| 34 | ANGGGNUAUGGUGACUUGCUCCAUUGGCCGAUAUAACGAUUCGGUCAG | 155 |
| 35 | CCUGCGUAGGGNGGGAAGUUGAAUCAGUUGUGGCGCUCUACUCAUUCGCC | 156 |
| 39 | CGAACGAGGAGGGAGUGGCAAGGGAUGGUUGGAUAGGCUCUACGCUCA | 157 |
| 41 | GUGCAAACUUAACCCGGGAACCGCGCGUUUCGAUUCGCUUUCCNUAUUCCA | 158 |
| 42 | CGAACGAGGAGGGAGUGGCAAGGGACGGUNNAUAGGCUCUACGCUCA | 159 |
| 43 | UCGGUGUGGCUCAGAAACUGACACGCGUGAGCUUCGCACACAUCUGC | 160 |
| 44 | UAUCGCUUUUCAUCAAUUCCACUUUUUCACUCUNAACUUGGGCGUGCA | 161 |
| 45 | GUGCAAACUUAACCCGGGAACCGCGCGUUUCGAUCCUGCAUCCUUUUUCC | 162 |
| 46 | UCGNUCGGUUGUGUGCCGGCAGCUUUGUCCAGCGUUGGGCCGAGGCC | 163 |
| 47 | AGUACCCAUCUCAUCUUUUCCUUUCCUUUCUUCAAGGCACAUUGAGGGU | 164 |
| 49 | CCUGAGUAGGGGGGAAGUUGAACCAGUUGUGGCNGCCUACUCAUUCNCCA | 165 |
| 51 | CCNNCCUNCUGUCGGCGCUUGUCUUUUUGGACGGGCAACCCAGGGCUC | 166 |
| 52 | CCAACCUNCUGUCGGCGCUUGUCUUUUUGGACGAGCAACUCAAGGCUCGU | 167 |
| 53 | CCAGCGCAGAUCCCGGGCUGAAGUGACUGCCGGCAACGGCCGCUCCA | 168 |
| 54 | UUCCCGUAACAACUUUUCAUUUUCACUUUUCAUCCAACCAGUGAGCAGCA | 169 |
| 55 | UAUCGCUUUCAUCAAAUUCCACUCCUUCACUUCUUUAACUUGGGCGUGCA | 170 |

TABLE 14

```
Starting RNAs:
40N7:
5'GGGAGGACGAUGCGG[-40N-]CAGACGACUCGCCCGA 3'     (SEQ ID NO: 186)
SELEX PCR Primers:
5G7:
5'TAATACGACTCACTATAGGGAGGACGATGCGG 3'           (SEQ ID NO: 187)
    T7 Promoter
3G7:
5'TCGGGCGAGTCGTCTG 3'                           (SEQ ID NO: 188)
```

TABLE 15

Conditions and progress of the SELEX against hKGF

| Round | [RNA], M | [KGF], M | net % bound | Signal/noise | PF[a] | Spin[b] | B-Wash[c] (ml) | U-Wash[d] (ml) | SPKD[e], M | KD[f], nM |
|---|---|---|---|---|---|---|---|---|---|---|
| 1 | 1.00E−06 | 3.00E−07 | 4.4 | 11.8 | | | 4 | | 5.61E−06 | 30.0 |
| 2 | 4.00E−06 | 3.00E−07 | 1.5 | 4.2 | | | 5 | | 1.58E−05 | |
| 3 | 1.00E−06 | 1.00E−07 | 5.9 | 20.6 | | | 5 | | 8.52E−07 | |
| 4 | 1.00E−06 | 1.00E−07 | 14.3 | 12.8 | + | | 8 | | 3.21E−06 | 17.0 |
| 5 | 3.00E−07 | 1.00E−08 | 2.5 | 4.5 | + | | 8 | | 7.64E−08 | |
| 6 | 3.70E−08 | 3.70E−09 | 0.7 | 2.6 | + | + | 15 | 15 | 3.73E−07 | |
| 7 | 4.10E−09 | 4.10E−10 | 1.1 | 8.2 | + | + | 20 | 20 | 2.46E−08 | 0.7 |
| 8 | 4.60E−10 | 4.60E−11 | 1.5 | 8.8 | + | + | 25 | 25 | 2.04E−09 | 0.3 |
| 9 | 5.10E−11 | 5.10E−12 | 0.7 | 5.9 | + | + | 25 | 25 | 8.76E−10 | |
| 10 | 1.70E−11 | 1.70E−12 | 0.3 | 2.1 | + | + | 25 | 25 | 4.12E−10 | |
| 2'F SELEX | | | | | | | | | | |
| 1 | 1.00E−06 | 3.00E−07 | 2.9 | 11.0 | | | 4 | | 3.39E−06 | 30.0 |
| 2 | 4.00E−06 | 3.00E−07 | 2.2 | 9.9 | | | 5 | | 9.28E−06 | |
| 3 | 3.00E−06 | 3.00E−07 | 5.7 | 5.7 | | | 5 | | 2.15E−06 | |
| 4 | 2.50E−06 | 3.00E−07 | 3.9 | 11.7 | + | | 8 | | 4.98E−06 | 15.0 |
| 5 | 6.70E−07 | 3.00E−08 | 2.3 | 5.8 | + | | 8 | | 3.64E−06 | |
| 6 | 1.20E−08 | 1.23E−09 | 0.3 | 1.8 | + | + | 15 | 15 | 1.59E−07 | |
| 7 | 1.40E−09 | 1.40E−10 | 1.1 | 11.2 | + | + | 20 | 20 | 6.86E−09 | 0.6 |
| 8 | 1.50E−10 | 1.50E−11 | 0.4 | 4.8 | + | + | 25 | 25 | 5.36E−10 | 0.3 |
| 9 | 1.70E−11 | 1.70E−12 | 0.2 | 3.1 | + | + | 25 | 25 | 5.67E−10 | |
| 10 | 1.70E−11 | 1.70E−12 | 0.3 | 3.0 | + | + | 25 | 25 | 1.42E−10 | |

[a]Prefiltered RNA through nitrocellulose to counter select for nitrocellulose binding molecules
[b]Brief spinning of the binding reactions
[c]Volume of buffer used to wash the captured complexes
[d]Volume of 0.5M urea wash following the buffer wash
[e]Calcualted single point $K_D$ from the binding data at each round
[f]$K_D$ values obtained from binding curves

TABLE 16

Sequences of 2'-NH₂ and 2'-F KGF ligands

| Clone | 5' constant | random | 3' constant | SEQ ID NO: |
|---|---|---|---|---|
| 2'-NH₂ ligands: | | | | |
| 1N | GGGAGGACGAUGCGG | GAAGGGACGAUAAAGAGGAAUCGAACAACAAGUGGCUGGC | CAGACGACUCGCCCGA | 189 |
| 2N | GGGAGGACGAUGCGG | GCGGGAAGGUCCGAAGACCGGCGAAGAGGAACGAGAUUGCC | CAGACGACUCGCCCGA | 190 |
| 4N | GGGAGGACGAUGCGG | GUGGGAAGGAGGUACCGGAAUUGCUAAAGAUACCACGGCC | CAGACGACUCGCCCGA | 191 |
| 6N | GGGAGGACGAUGCGG | GCAGGGAGCAAUGAACUCAAGUCAAGCCGUGCACGUGGG | CAGACGACUCGCCCGA | 192 |
| 8N | GGGAGGACGAUGCGG | UAGCUGCUGUCAUGCAAGACACUAGAAGAGAUAAGAUGGGG | CAGACGACUCGCCCGA | 193 |
| 10N | GGGAGGACGAUGCGG | GGGCCGGAUUUGAACGGACGACUUCGGGUUAUGAGCCGACGU | CAGACGACUCGCCCGA | 194 |
| 11N | GGGAGGACGAUGCGG | UCCAGGGCUAGAAGUGUCGGGGUAGGAACAUAAAGGCGGC | CAGACGACUCGCCCGA | 195 |
| 14N | GGGAGGACGAUGCGG | AAGUUCUAACAAGUUAGUGGAAGGUUCCACUGAAUGUA | CAGACGACUCGCCCGA | 196 |
| 16N | GGGAGGACGAUGCGG | AUGGAGCUGAAAU | CAGACGACUCGCCCGA | 197 |
| 22N | GGGAGGACGAUGCGG | GUGGGAAGAUGAGCCGGUCGGCAGUAUGUGACACUGCGG | CAGACGACUCGCCCGA | 198 |
| 24N | GGGAGGACGAUGCGG | GAGGGAAUGAGGAAACAACUAGCAGAUAACCGAGCUGGC | CAGACGACUCGCCCGA | 199 |
| 25N | GGGAGGACGAUGCGG | AUGGAGCUGAAAU | CAGACGACUCGCCCGA | 200 |
| 27N | GGGAGGACGAUGCGG | UUGCUCUACAAUGACGCGGUGACUCCGCAGUUCUGGACA | CAGACGACUCGCCCGA | 201 |
| 28N | GGGAGGACGAUGCGG | GAGGGAGAGAAUGAACAGCGAAAACAGCGAAAUGCGUGUGG | CAGACGACUCGCCCGA | 202 |
| 29N | GGGAGGACGAUGCGG | GCGGGAAAGCUAAUGGAAGUGGAAUCAGUCACAGUGCGG | CAGACGACUCGCCCGA | 203 |
| 34N | GGGAGGACGAUGCGG | GCUUAGGGAAAUGGUUCUGAGGGGU | CAGACGACUCGCCCGA | 204 |
| 35N | GGGAGGACGAUGCGG | GAAGGGAACACGGAAUAAGACAAGUCGAACAAAGCCGAGGUG | CAGACGACUCGCCCGA | 205 |
| 36N | GGGAGGACGAUGCGG | AUGGAGCUGAAAU | CAGACGACUCGCCCGA | 206 |
| 37N | GGGAGGACGAUGCGG | GGAGACGUAGACGGGAACAUAGAACGAACAUCAACGCGUG | CAGACGACUCGCCCGA | 207 |
| 42N | GGGAGGACGAUGCGG | GAAGUGGAUAGAACAGUCAGAAAAUGUAAGCGUGAGGUG | CAGACGACUCGCCCGA | 208 |
| 43N | GGGAGGACGAUGCGG | GAAGGGUAGGAAGGUCAAGAGAGAAACAGCGCUUCGGGGGUG | CAGACGACUCGCCCGA | 209 |
| 47N | GGGAGGACGAUGCGG | GGCAAAGGAACAGAGCCCCUGGUGGGGGAAGGAUUCU | CAGACGACUCGCCCGA | 210 |
| 48N | GGGAGGACGAUGCGG | AGAACCAACAGAGCCCCUGGUGGGGGAAGGAUUCU | CAGACGACUCGCCCGA | 211 |
| 54N | GGGAGGACGAUGCGG | ACACACAAGGUGAAGGUCAGACGCGAAUUACGUGGGUGG | CAGACGACUCGCCCGA | 212 |
| 55N | GGGAGGACGAUGCGG | UCGUGGGGUGGGGGCAGCGUUGGGGAAUAAGUAACUGGUAACGGCUGGC | CAGACGACUCGCCCGA | 213 |
| 57N | GGGAGGACGAUGCGG | GGUGGUGGUUACCUGUAAUUAUAUUGAUCUGGCUUUAG | CAGACGACUCGCCCGA | 214 |
| 59N | GGGAGGACGAUGCGG | CCCCUUAGCUCAGUGGGUUAGAG | CAGACGACUCGCCCGA | 215 |
| 60N | GGGAGGACGAUGCGG | UAAGUGGAAUAGGGUUAAACAGCUGGAAAUAACGUAGGUGGC | CAGACGACUCGCCCGA | 216 |
| 65N | GGGAGGACGAUGCGG | GUAGGGAGUAGGACAGACAUAAACAGUGCAACCAUCGUGGC | CAGACGACUCGCCCGA | 217 |
| 69N | GGGAGGACGAUGCGG | AAACGGCGUGCAAAAGUGAGGGGGUAGGAUGUACCAUGGGU | CAGACGACUCGCCCGA | 218 |
| 71N | GGGAGGACGAUGCGG | GAGGGGAAAAUGAGACGACAGAAUUGACGGAAGUACUGGG | CAGACGACUCGCCCGA | 219 |
| 72N | GGGAGGACGAUGCGG | | CAGACGACUCGCCCGA | |
| 2'-F ligands: | | | | |
| 2F | GGGAGGACGAUGCGG | GCAUUGUCAAUACCUUGUUUUAUCCUUUCUAGCGGCC | CAGACGACUCGCCCGA | 220 |
| 3F | GGGAGGACGAUGCGG | AUCGUAAUGCCACUACACUUUCGAACCCACGUGGC | CAGACGACUCGCCCGA | 221 |
| 5F | GGGAGGACGAUGCGG | CGUCCCGUCACGCUGUCCUGAUAACCCUUCUGUGCC | CAGACGACUCGCCCGA | 222 |
| 6F | GGGAGGACGAUGCGG | GAUCCUUUGUGUGGCUCUGUUGACCCCCUCGUGUUCCCC | CAGACGACUCGCCCGA | 223 |
| 7F | GGGAGGACGAUGCGG | CGGGUACUCUUCGCCAGCUCCCAAGCGCGACCUGUGCC | CAGACGACUCGCCCGA | 224 |
| 8F | GGGAGGACGAUGCGG | UUUCGAAUAGGGCCAUUUCUCACUAGUCUACCCUGCC | CAGACGACUCGCCCGA | 225 |
| 9F | GGGAGGACGAUGCGG | AUAAUGGCUAGAACUAGCUACUCUGGCGUCCGUGCC | CAGACGACUCGCCCGA | 226 |
| 10F | GGGAGGACGAUGCGG | GACCAGAUGCCGAUUUUUCAGCAAUCCCCCGCUGCC | CAGACGACUCGCCCGA | 227 |
| 11F | GGGAGGACGAUGCGG | UGAUGGCGACCAGUCAAACCGUGCUUCUAUACUCCCCGC | CAGACGACUCGCCCGA | 228 |
| 12F | GGGAGGACGAUGCGG | GAAUAACAGGGCCAGAAUUCUCAUCUNNCUUCCCGUGACC | CAGACGACUCGCCCGA | 229 |
| 13F | GGGAGGACGAUGCGG | CACCUUAGACCUGUCCCCAAGGCGUGAAGUUGCUGUGCC | CAGACGACUCGCCCGA | 230 |

TABLE 16-continued

Sequences of 2'-NH, and 2'-F KGF ligands

| Clone | 5' constant | random | 3' constant | SEQ ID NO: |
|---|---|---|---|---|
| 14F | GGGAGGACGAUGCGG | UGGCUCCCAAUCUAAACUUUCUCCAUCGUAUCUGGGC | CAGACGACUCGCCCGA | 231 |
| 15F | GGGAGGACGAUGCGG | UCAUGGUGUCUUUCCACAGCUCUUCCCAUGAUCGCCCGGC | CAGACGACUCGCCCGA | 232 |
| 16F | GGGAGGACGAUGCGG | GAAUUCCCAGCGCUUGACUGAUACAAACNUUCCCGUGCG | CAGACGACUCGCCCGA | 233 |
| 19F | GGGAGGACGAUGCGG | CAA-NNNNNNCUCUCCUGGCGUUCCGCAACCGCCCC | CAGACGACUCGCCCGA | 234 |
| 20F | GGGAGGACGAUGCGG | AGUAUCCAGCCUGGAUUCAUAGUCAGUGCUCUCGUGCC | CAGACGACUCGCCCGA | 235 |
| 21F | GGGAGGACGAUGCGG | UCCUAGCAGCGAUUCAUCCCGUUCUCUCAGCGUUGCCC | CAGACGACUCGCCCGA | 236 |
| 23F | GGGAGGACGAUGCGG | CCUGAAGUACAGGCUCUAAACUCCAAGCGCGACGUCGC | CAGACGACUCGCCCGA | 237 |
| 23F | GGGAGGACGAUGCGG | CCCUACCACUUUUCCCUCUACUGUAUCCGUCCC | CAGACGACUCGCCCGA | 238 |
| 24F | GGGAGGACGAUGCGG | UGGUCCCUAGAUCUACAGCACUCUCAUCGCAUUGGGC | CAGACGACUCGCCCGA | 239 |
| 26F | GGGAGGACGAUGCGG | UCAAGCUAACAGUCUGGCAAUGGCCAUUAUGGCGCCC | CAGACGACUCGCCCGA | 240 |
| 27F | GGGAGGACGAUGCGG | CaGUCUGGAUCUCUAUGGAAUUUAGUCCUCAACUGUGCCC | CAGACGACUCGCCCGA | 241 |
| 28F | GGGAGGACGAUGCGG | GAUUCUUCGGCAAGUGAAAAAAUAUCCUGCUUCCCGAGC | CAGACGACUCGCCCGA | 242 |
| 29F | GGGAGGACGAUGCGG | GGACUCAACUAAGUCCCAUUUGCCUCGCUCCUCGUGCC | CAGACGACUCGCCCGA | 243 |
| 31F | GGGAGGACGAUGCGG | AACGGAGAUGCCCCUCAAMAUUUACCGUCUCGUUUGCGCCC | CAGACGACUCGCCCGA | 244 |
| 35F | GGGAGGACGAUGCGG | CGAAAUUAGCUCUUAUGACUCAGUUUCCUUGCCGCC | CAGACGACUCGCCCGA | 245 |
| 37F | GGGAGGACGAUGCGG | GCCCGAUCUACUGCAUUACCGAAACGAUUUCCCACUGUG | CAGACGACUCGCCCGA | 246 |
| 38F | GGGAGGACGAUGCGG | NGACUGAUUUUUCCCUUGNBCAGUGUAAUUUCCUGGCUGCCC | CAGACGACUCGCCCGA | 247 |
| 41F | GGGAGGACGAUGCGG | GGACUUUGACAGGCAUUGAUUUCGACCUGUCCCGUGGC | CAGACGACUCGCCCGA | 248 |
| 42F | GGGAGGACGAUGCGG | CGACACAAUAGCCUUUGAUCCCAUGAUGGCUCGCCGUGCC | CAGACGACUCGCCCGA | 249 |
| 43F | GGGAGGACGAUGCGG | UGUAGUUCCCUGAUGCCAUUCUUUCCAUGCGCACGC | CAGACGACUCGCCCGA | 250 |
| 44F | GGGAGGACGAUGCGG | UCGAGUGUUCUCCCUCGGUAACUAUUNNNNAUUUCGUGCC | CAGACGACUCGCCCGA | 251 |
| 45F | GGGAGGACGAUGCGG | GUCGUAUUCAUCCUCUGUUCGUUGUGCACCUGGCC | CAGACGACUCGCCCGA | 252 |
| 49F | GGGAGGACGAUGCGG | GGACUUUGACAGGCaUUGAUUUCGACGUGUUCCCGUGGC | CAGACGACUCGCCCGA | 253 |
| 50F | GGGAGGACGAUGCGG | UGAUCAAUCGGCGCUUUACUCUCUUGCGCUCACCGUGCC | CAGACGACUCGCCCGA | 254 |
| 51F | GGGAGGACGAUGCGG | CAGUUCCCUAGGUUUCAUCUUGCAGCAUUCGGGUNC | CAGACGACUCGCCCGA | 255 |
| 53F | GGGAGGACGAUGCGG | AUCAAAAGCACUCAUUCCCGUGCCGCUUCAUUGGUCCC | CAGACGACUCGCCCGA | 256 |
| 54F | GGGAGGACGAUGCGG | AAGAUCUCCCAACUGCUGUGCUAAUAAUUCUCCGGUCCC | CAGACGACUCGCCCGA | 257 |
| 55F | GGGAGGACGAUGCGG | UCCGUCAUAACGGCCAUAAACUGGAAUACUCCCUGGCC | CAGACGACUCGCCCGA | 258 |
| 56F | GGGAGGACGAUGCGG | GGACAAWYAGCGGUGUCUUUUCAUUNKAUCUCCGACRUCC | CAGACGACUCGCCCGA | 259 |
| 57F | GGGAGGACGAUGCGG | UGACAUUCGGCUGAUCCAAUCACCCAGCCACCGCGC | CAGACGACUCGCCCGA | 260 |
| 58F | GGGAGGACGAUGCGG | GAACUAAUGGCCGUGAUUAACCAAUGCAGGCUUCCUGCG | CAGACGACUCGCCCGA | 261 |
| 60F | GGGAGGACGAUGCGG | UGACAUGGAAUUUCUACGGGCCCGAUCCUGCCAGCCGUGUG | CAGACGACUCGCCCGA | 262 |

TABLE 17

$K_d$ values hKGF ligands

| Clone | $K_d$ in nM 1 | 2 | Clone | $K_d$ in nM 1 | 2 |
|---|---|---|---|---|---|
| 1N | 0.51 | | 2F | 1.77 | |
| 2N | 0.77 | | 3F | 4.47 | |
| 4N | 0.75 | | 5F | 2.53 | |
| 6N | 0.71 | | 6F | 0.05 (37) | 3.25 |
| 10N | 1.10 | | 7F | 3.69 | |
| 11N | 1.28 | | 8F | 2.63 | |
| 14N | 0.44 | | 9F | 0.83 | |
| 16N | 1.40 | | 10F | 0.47 | |
| 22N | 5.70 | | 11F | 3.74 | |
| 24N | 1.16 | | 12F | 1.38 | |
| 25N | 0.87 | | 13F | 0.03 (28) | |
| 27N | ND | | 14F | 0.006–0.03 (25–44) | |
| 28N | 2.54 | | 15F | 0.07 (33) | |
| 29N | 0.43 | | 16F | 0.83 (49) | 3.39 |
| 34N | 0.80 | | 19F | 1.5 | 0.94–2.57 |
| 35N | 2.32 | | 20F | 2.05 | 8.70 |
| 36N | 8.27 | | 21F | ND | 44.8 |
| 37N | ND | | 22F | 2.75 | |
| 42N | 0.78 | | 23F | 2.52 | |
| 43N | 0.79 | | 24F | 2.02 | |
| 47N | 1.76 | | 26F | 0.23 (43) | 2.55 |
| 48N | 1.34 | | 27F | 1.52 | |
| 54N | 5.35 | | 28F | ND | |
| 55N | 1.25 | | 29F | 3.24 | |
| 57N | 35.8 | | 31F | 1.0 | |
| 59N | 22.0 | | 35F | 1.1 | |
| 60N | 7.38 | | 37F | 0.46 | |
| 65N | 26.56 | | 38F | 0.33 | |
| 69N | 15.20 | | 41F | 1.44 | |
| 71N | 3.52 | | 42F | 0.9 | |
| 72N | 7.67 | | 43F | 1.13 | |
| random | 30 | | 44F | 1.32 | |
| | | | 45F | 4.7 | |
| | | | 49F | 1.0 | |
| | | | 50F | 0.12 (12) | 2.10 |
| | | | 51F | 1.27 | |
| | | | 53F | 0.70 | |
| | | | 54F | 1.23 | |
| | | | 55F | 2.52 | |
| | | | 56F | 0.07 (32) | 3.00 |
| | | | 57F | 1.20 | |
| | | | 58F | 2.52 | |
| | | | 60F | 2.10 | |
| | | | random | 30 | |

For biphasic curves, Kd1 is for the high affinity component.
Number in parentheses indicate the percent of the high affinity component.

TABLE 18

Binding Specificity of the 2'-F Ligand K14F

| Target | Ratio: $K_D$ Target/$K_D$ hKGF |
|---|---|
| human hKGF | 1 |
| rat hKGF | 1,254 |
| human aFGF | 38,650 |
| human bFGF | 1,071 |
| Human PDGF | 432 |

The ratios shown are averages of at least two determinations

TABLE 19

$IC_{50}$ values from the PC-3 assay

| Competitor | IC50, nM |
|---|---|
| hKGF | 0 |
| Heparin, 5,000 | 30 |
| 40N7F | >1000 |
| K6F | 4 |
| K13F | 30 |
| K14F | 10 |
| K15F | 20 |
| K56F | 1 |
| K10F | 30 |
| K37F | 20 |
| K38F | 0.6 |
| K43F | 80 |
| 40N7N | >1000 |
| K1N | 50 |
| K2N | 200 |
| K4N | 70 |
| K6N | 80 |
| K14N | 6 |
| K29N | 40 |
| K42N | 800 |
| K43N | 800 |

TABLE 20

Ki values of hKGF competitors on the PC3 and NIH3T3/FGFR-2 competition assay

| Cell line | Competitor | Ki, nM | R | |
|---|---|---|---|---|
| PC-3 | hKGF | 7.700 | 0.95519 | |
| | 2'F random | 930.000 | 0.99713 | |
| | 2'NH$_2$random | 673.000 | 0.85357 | |
| | Hep5000 | 6.500 | 0.99984 | |
| | K14F | 0.200 | 0.97735 | |
| | K6F | 0.160 | 0.95927 | |
| | K38F | 0.220 | 0.99013 | |
| | K56F | 0.160 | 0.95927 | |
| | K14N | 1.400 | 0.94698 | |
| NIH3T3/FGFR-2 | hKGF | 0.034 | 0.9933 | |
| | 2'F random | >10,000.000 | | |
| | 2'NH$_2$random | >10,000.000 | | |
| | Hep5000 | 26.300 | 0.97856 | partial comp. |
| | K14F | 2.700 | 0.99047 | |
| | K6F | 6.800 | 0.96202 | |
| | K38F | 20.000 | 0.98659 | |
| | K56F | 27.400 | 0.97582 | |
| | K14N | 10.600 | 0.97856 | partial comp. |

TABLE 21

IC50 values obtained with the gel shift assay

| Competitor | IC50, nM |
|---|---|
| KGF | 70 |
| bFGF | 1,500 |
| Lysozyme | 10,000 |

TABLE 22

Binding Specificity of Ligand K14F3'T

| | random RNA | | K14F3'T | | |
|---|---|---|---|---|---|
| Protein | [a]$K_d1$, nM | [b]$K_d2$, nM | $K_d1$, nM | $K_d2$, nM | [c]DF |
| hKGF | 20.1 | 0.0008 | 10.2 | | 1 |
| rKGF | 45.3 | 0.0041 | 70.0 | | 5 |

TABLE 22-continued

Binding Specificity of Ligand K14F3'T

| | random RNA | | K14F3'T | | |
|---|---|---|---|---|---|
| Protein | $^aK_d1$, nM | $^bK_d2$, nM | $K_d1$, nM | $K_d2$, nM | $^cDF$ |
| hbFGF | 0.0375 | 10.3 | | 10.0 | $1.2 \times 10^4$ |
| haFGF | | 16,000,000 | | 24,000,000 | $3 \times 10^{10}$ |
| hPDGF-AB | | 22.0 | | 50.0 | $6.2 \times 10^4$ |
| hTGFβ1 | | 10.4 | | 98.0 | $1.2 \times 10^5$ |
| hEGF | | 2,000 | | 256 | $3.2 \times 10^5$ |
| Thrombin | | 7,200,000 | | 22,700,000 | $2.8 \times 10^{10}$ |

$^a$High affinity dissociation constant from biphasic binding curves.
$^b$Low affinity dissociation constant from biphasic binding curves or affinity dissociation constant from monophasic binding curves.
$^c$Discrimination factor defined as the ratio of the highest affinity $K_d$ of 14F3'T for the corresponding protein over the affinity $K_d$ for hKGF.

TABLE 23

| | S1 | L1 | S2 | S1' | L3 | S2' | H | L | SEQ ID NO: |
|---|---|---|---|---|---|---|---|---|---|
| 143'T | GGGAGG | AC | GAUGCGGUGG | UCUCCC | AAUUCUAAACUUUCU | CCAUCGUAUC | | | 272 |
| T2 | GGGAGG | AC | GAUGCGGUGG | UCUCCC | AAUUCUAAACUUUCU | CCAUCGUA.. | − | + | 273 |
| T3 | GGGAGG | AC | ..UGCGGUGG | UCUCCC | AAUUCUAAACUUUCU | CCAUCGUA.. | − | − | 274 |
| T4 | GGGAGG | AC | GAUGCGGUGG | UCUCCC | ....CUAAACUUUCU | CCAUCGUAUC | + | + | 275 |
| T5 | GGGAGG | AC | GAUGCGGUGG | UCUCCC | AAUUCUA....UUUCU | CCAUCGUAUC | + | + | 276 |
| T6 | GGGAGG | AC | GAUGCGGUGG | UCUCCC | AAUUCUAAACU.... | CCAUCGUAUC | ± | + | 277 |
| T7 | GGGAGG | AC | GAUGCGGUGG | UCUCCC | AAUU...AACU.... | CCAUCGUAUC | − | − | 278 |
| T8 | ..GAGG | AC | GAUGCGGUGG | UCUCCC | AAUUCUAAACUUUCU | CCAUCGUAUC | − | + | 279 |
| T10 | GGGAGG | AC | GAUGCGGUGG | UCUCCC | AAUU.......UUCU | CCAUCGUAUC | − | − | 280 |
| T11 | GGGAGG | AC | GAUGCGGUGG | UCUCCC | AAUUCUA........ | CCAUCGUAUC | − | − | 281 |
| T12 | .GGAGG | AC | GAUGCGGUGG | UCUCCC | AAUUCUA....UUCU | CCAUCGUAUC | − | − | 282 |
| T13 | .GGAGG | AC | GAUGCGGUGG | UCUCC. | AAUUCUA....UUCU | CCAUCGUAUC | − | − | 283 |
| T14 | ..GAGG | AC | GAUGCGGUGG | UCUCCC | AAUUCUA....UUCU | CCAUCGUAUC | − | − | 284 |
| T15 | ..GAGG | AC | GAUGCGGUGG | UCUC.. | AAUUCUA....UUCU | CCAUCGUAUC | − | − | 285 |
| T16 | GGGAGG | .C | GAUGCGGUGG | UCUCCC | AAUUCUA....UUCU | CCAUCGUAUC | − | ± | 286 |
| T18 | GGGAGG | AC | GAUGCGGUGG | UCUCCC | AAUUCUA.....UCU | CCAUCGUAUC | + | + | 287 |
| T19 | GGGAGG | AC | GAUGCGGUGG | UCUCCC | AAUUCUA......CU | CCAUCGUAUC | − | − | 288 |
| T20 | GGGAGG | AC | GAUGCGGUGG | UCUCCC | AAUUCUA.......U | CCAUCGUAUC | − | − | 289 |
| T21 | GGGAGG | AC | GAUGCGGUGG | UCUCCC | AAUUCU.....UUCU | CCAUCGUAUC | + | + | 290 |
| T22 | GGGAGG | AC | GAUGC..UGG | UCUCCC | AAUUC......UUCU | CCAUCGUAUC | + | + | 291 |
| T29 | GGG.G. | AC | GAUGCGGUGG | .C.CCC | AAUUCUA....UUCU | CCAUCGUAUC | − | − | 292 |
| T30 | GGG... | AC | GAUGCGGUGG | ...CCC | AAUUCUA....UUCU | CCAUCGUAUC | − | − | 293 |
| T31 | .....G | AC | GAUGCGGUGG | ...CCC | AAUUCUA....UUCU | CCAUCGUAUC | − | − | 294 |
| T32 | ....GG | AC | GAUGCGGUGG | ...CCC | AAUUCUA....UUCU | CCAUCGUAUC | − | − | 295 |
| T33 | ...... | .. | GAUGCGGUGG | ...CCC | AAUUCUA....UUCU | CCAUCGUAUC | − | − | 296 |
| T34 | ...... | .. | GAUGCGGUGG | UCUCCC | AAUUCUA....UUCU | CCAUCGUAUC | − | − | 297 |
| T35 | ...... | .. | .....GGUGG | UCUCCC | AAUUCUA....UUCU | CCAUCGUAUC | − | − | 298 |
| T36 | GGGAGG | AC | GAUG...........  | ................ | .......... | | − | − | 299 |
| T37 | GGGAGG | AC | GAUGCGGUGG | UCUCCC | AAUUC......UCU | CCAUCGUAUC | − | − | 300 |
| T39 | GGGAGG | AC | GAUGCGGUG. | UCUCCC | AAUUC......UUCU | .CAUCGUAUC | − | − | 301 |
| T40 | GGGAGG | AC | GAUGCGG.GG | UCUCCC | AAUUC......UUCU | CC.UCGUAUC | − | − | 302 |
| T41 | GGGAGG | AC | GAUGCGG.G. | UCUCCC | AAUUC......UUCU | .C.UCGUAUC | − | − | 303 |
| T22mu | GGGAGU | AC | GAUGCGGUGG | UCUCCC | AAUUC......UUCU | CCAUCGUAUC | − | − | 304 |
| T35/36 equimolar amounts of T35 and T36 | | | | | | | − | − | |

We claim:

1. A purified and isolated non-naturally occurring modified single-stranded ribonucleic acid ligand to platelet-derived growth factor (PDGF) wherein said modified ligand is substantially homologous to and has substantially the same ability to bind PDGF as a modified ligand selected from the group consisting of the sequences set forth in Table 13 (SEQ ID NOS:128–170).

2. A purified and isolated non-naturally occurring modified single-stranded ribonucleic acid ligand to platelet-derived growth factor (PDGF) wherein said modified ligand has substantially the same structure and substantially the same ability to bind PDGF as a modified ligand selected from the group consisting of the sequences set forth in Table 13 (SEQ ID NOS:128–170).

3. A purified and isolated non-naturally occurring single-stranded deoxyribonucleic acid ligand to platelet-derived growth factor (PDGF) wherein said ligand is substantially homologous to and has substantially the same ability to bind PDGF as a ligand selected from the group consisting of the sequences set forth in Tables 8 and 9, and FIGS. 3, 4 and 9 (SEQ ID NOS: 93–124, 171–176).

4. A purified and isolated non-naturally occurring single stranded deoxyribonucleic acid ligand to platelet-derived growth factor (PDGF) wherein said ligand has substantially the same structure and substantially the same ability to bind PDGF as a ligand selected from the group consisting of the sequences set forth in Tables 8 and 9, and FIGS. 3, 4 and 9 (SEQ ID NOS: 93–124, 171–176).

5. A purified and isolated non-naturally occurring modified single-stranded ribonucleic acid ligand to human keratinocyte growth factor (hKGF) wherein said modified ligand is selected from the group consisting of SEQ ID NOS: 189–264, 268–304.

6. A purified and isolated non-naturally occurring modified single-stranded ribonucleic acid ligand to human keratinocyte growth factor (hKGF) wherein said modified ligand is substantially homologous to and has substantially the same ability to bind hKGF as a modified ligand selected from the group consisting of SEQ ID NOS: 189–264, 268–304.

7. A purified and isolated non-naturally occurring modified ribonucleic acid ligand to human keratinocyte growth factor (hKGF) wherein said modified ligand has substantially the same structure and substantially the same ability to bind hKGF as a modified ligand selected from the group consisting of SEQ ID NOS: 189–264, 268–304.

8. A purified and isolated non-naturally occurring modified ribonucleic acid ligand to basic fibroblast growth factor (bFGF) wherein said modified ligand has the sequence as shown in SEQ ID NO: 267.

* * * * *

SEQUENCE LISTING (1) GENERAL INFORMATION:

(iii) NUMBER OF SEQUENCES: 304

(2) INFORMATION FOR SEQ ID NO: 1:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 1:

GGGGGAGAAC GCGGAUCCNN NNNNNNNNNN NNNNNNNNNN NNNNNNNNNN        50

NNNNNNNNNN NNNNNNNNNN NNNNNNNNNN NNAAGCUUCG CUCUAGAUCU       100

CCCUUUAGUG AGGGUUA                                           117

(2) INFORMATION FOR SEQ ID NO: 2:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 2:

GGGGGAGAAC GCGGAUCCNN NNNNNNNNNN NNNNNNNNNN NNNNNNNNNN        50

NNNNNNNNAA GCUUCGCUCU AGAUCUCCCU UUAGUGAGGG UUA               93

(2) INFORMATION FOR SEQ ID NO: 3:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 3:

GGGGGAGAAC GCGGAUCCUG UCUCCACCGC CGAUACUGGG GUUCCUGGGG        50

CCCCUCCAUG GAGGAGGGGG GAGGGGGUGG UUCGGAGAAA GCUUCGCUCU       100

GAAUCUCCCU UUAGUGAGGG UUA                                    123

(2) INFORMATION FOR SEQ ID NO: 4:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GGGAGAACGC GGATCCNNNN NNNNNNNNNN NNNNNNNNNN NNNNNNNNNN        50

NNNNNNNNNN NNNNNNNNNN NNNNNNNNNN AAGCTTCGCT CTAGA             95

(2) INFORMATION FOR SEQ ID NO: 5:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GGGAGAACGC GGATCCNNNN NNNNNNNNNN NNNNNNNNNN NNNNNNNNNN        50

NNNNNNAAGC TTCGCTCTAG A        71

(2) INFORMATION FOR SEQ ID NO: 6:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

GGGGGAGAAC GCGGATCCTG TCTCCACCGC CGATACTGGG GTTCCTGGGG        50

CCCCTCCATG GAGGAGGGGG TGGTTCGGAG AAAGCTTCGC TCTAG        95

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

TAATACGACT CACTATAGGG GGAGTCTGCG GATCC        35

(2) INFORMATION FOR SEQ ID NO: 8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

TAATACGACT CACTATAGGG GGAGAACGCG GATCC        35

(2) INFORMATION FOR SEQ ID NO: 9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

TAACCCTCAC TAAAGGGAGA TCTAGAGCGA AGCTT        35

(2) INFORMATION FOR SEQ ID NO: 10:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GATTTAGGTG ACACTATAGA ATATGCATCA CTAGTAAGCT TTGCTCTAGA           50

(2) INFORMATION FOR SEQ ID NO: 11:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 11:

GGATCCCGGA GCTCCCTATA GTGAGTCGTA TTA                             33

(2) INFORMATION FOR SEQ ID NO: 12:

(i) SEQUENCE CHARACTERISTICS:
            (A) LENGTH: 125 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:   All pyri
                modified (xi) SEQUENCE DESCRIPTION: SEQ ID NO: 12:

GGGGGAGAAC GCGGAUCCGA GCAAUCCCAG GCGCAUAGCU UCCGAGUAGA           50

CAGGAGGGAG GGUGGAUGU GGCGUCUACU CGGUGUCGUG AAGCUUCGCU           100

CUAGAUCUCC CUUUAGUGAG GGUUA                                     125

(2) INFORMATION FOR SEQ ID NO: 13:

(i) SEQUENCE CHARACTERISTICS:
            (A) LENGTH: 125 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:   All pyri
                modified (xi) SEQUENCE DESCRIPTION: SEQ ID NO: 13:

GGGGGAGAAC GCGGAUCCGA GCAACCCCAG GCGCAUAGCU UCCGAGUAGA           50

CAGGAGGGAG GGUGGAUGU GGCGUCUACU CGGUGUCGUG AAGCUUCGCU           100

CUAGAUCUCC CUUUAGUGAG GGUUA                                     125

(2) INFORMATION FOR SEQ ID NO: 14:

(i) SEQUENCE CHARACTERISTICS:
            (A) LENGTH: 125 base pairs
            (B) TYPE: nucleic acid
            (C) STRANDEDNESS: single
            (D) TOPOLOGY: linear (ii) MOLECULE TYPE: RNA (ix) FEATURE:

(D) OTHER INFORMATION:    All pyri
            modified (xi) SEQUENCE DESCRIPTION: SEQ ID NO: 14:

GGGGGAGAAC GCGGAUCCGA GCAACCCCAG GCGCAUAGCU UCCGAGUAGA         50

CAGGCGGGAG GGUGGAUGU GGCGUCUACU CGGAGUCGUG AAGCUUCGCU         100

CUAGAUCUCC CUUUAGUGAG GGUUA                                   125

(2) INFORMATION FOR SEQ ID NO: 15:

(i) SEQUENCE CHARACTERISTICS:
        (A) LENGTH:  116 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:    All pyri
            modified (xi) SEQUENCE DESCRIPTION: SEQ ID NO: 15:

GGGGGAGAAC GCGGAUCCGG CAACCCCAGG CGCAUAGCUU CCGAGUAGAC         50

AGGCGGGAGG GGUGGAUGUG GCGUCACGAG GAAGCUUCGC UCUAGAUCUC        100

CCUUUAGUGA GGGUUA                                             116

(2) INFORMATION FOR SEQ ID NO: 16:

(i) SEQUENCE CHARACTERISTICS:
        (A) LENGTH:  123 base pairs
        (B) TYPE:  nucleic acid
        (C) STRANDEDNESS:  single
        (D) TOPOLOGY:  linear (ii) MOLECULE TYPE:  RNA (xi) SEQUENCE DESCRIPTION: SEQ ID NO: 16:

GGGGGAGAAC GCGGATCCGC AAUCCCAGGC GCAUAGCUUC CGAGUAGACA         50

GGAGGGAGGG GUGGAUGUGG CGUCUACUCG GCGUCGUGAA GCUUCGCUCU        100

AGAUCUCCCU UUAGUGAGGG UUA                                     123

(2) INFORMATION FOR SEQ ID NO: 17:

(i) SEQUENCE CHARACTERISTICS:
        (A) LENGTH:  117 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:    All pyri
            modified (xi) SEQUENCE DESCRIPTION: SEQ ID NO: 17:

GGGGGAGAAC GCGGAUCCGA GCAAUCCCAG GCGCAUAGCU UCCGAGUAGA         50

CAGGAGGGAG GGUGGAUGU GGCGUCUCGA GGAAGCUUCG CUCUAGAUCU        100

CCCUUUAGUG AGGGUUA                                            117

(2) INFORMATION FOR SEQ ID NO: 18:

(i) SEQUENCE CHARACTERISTICS:
    (A) LENGTH:  123 base pairs
    (B) TYPE:  nucleic acid
    (C) STRANDEDNESS:  single
    (D) TOPOLOGY:  linear (ii) MOLECULE TYPE:  RNA (ix) FEATURE:
    (D) OTHER INFORMATION:     All pyri
        modified (xi) SEQUENCE DESCRIPTION:  SEQ ID NO: 18:

```
GGGGGAGAAC GCGGAUCCGA GCAAGCCCUG GCAUAGCUUC CGAGUAGACA        50

GGAGGGAGGG GUGGAUGUGG CGUCUACUCG GUGUCGUGAA GCUUCGCUCU       100

AGAUCUCCCU UUAGUGAGGG UUA                                    123
```

(2) INFORMATION FOR SEQ ID NO: 19:

(i) SEQUENCE CHARACTERISTICS:
        (A) LENGTH:  115 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:     All pyri
            modified (xi) SEQUENCE DESCRIPTION:  SEQ ID NO: 19:

```
GGGGGAGAAC GCGGAUCCGG CAAUCCCAGG CGCAUAGCUU CCGAGUAGAC        50

AGGAGGGAGG GGUGGAUGUG GUGUACGAGG AAGCUUCGCU CUAGAUCUCC       100

CUUUAGUGAG GGUUA                                              115
```

(2) INFORMATION FOR SEQ ID NO: 20:

(i) SEQUENCE CHARACTERISTICS:
        (A) LENGTH:  116 base pairs
        (B) TYPE:  nucleic acid
        (C) STRANDEDNESS:  single
        (D) TOPOLOGY:  linear (ii) MOLECULE TYPE:  RNA (xi) SEQUENCE DESCRIPTION:  SEQ ID NO: 20:

```
GGGGGAGAAC GCGGAUCCGA GCAAUCCCAG GCGCAUAGCU UCCGAGUAGA        50

CAGGAGGGAG GGGUGGAUGU GGUGUCUCGA GAAGCUUCGC UCUAGAUCUC       100

CCUUUAGUGA GGGUUA                                             116
```

(2) INFORMATION FOR SEQ ID NO: 21:

(i) SEQUENCE CHARACTERISTICS:
        (A) LENGTH:  98 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:     All pyri
            modified (xi) SEQUENCE DESCRIPTION:  SEQ ID NO: 21:

```
GGGGGAGAAC GCGGAUCCAA GCUUCGAGUA GACAGGAGGG AGGGGUGGAU        50

GUGGAGUCUC GAGAAGCUUC GCUCUAGAUC UCCCUUUAGU GAGGGUUA          98

(2) INFORMATION FOR SEQ ID NO: 22:

(i) SEQUENCE CHARACTERISTICS:
        (A) LENGTH:  113 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:      All pyri
            modified (xi) SEQUENCE DESCRIPTION:  SEQ ID NO: 22:

GGGGGAGAAC GCGGAUCCGA GCAAUCCUAA GCAUAGCUUC GAGUAGACAG        50

GAGGGAGGGG UGGAUGUGGC GUCUCGAGAA GCUUCGCUCU AGAUCUCCCU        100

UUAGUGAGGG UUA                                                113

(2) INFORMATION FOR SEQ ID NO: 23:

(i) SEQUENCE CHARACTERISTICS:
        (A) LENGTH:  116 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:    All U's (ix) FEATURE:
        (D) OTHER INFORMATION:    All C's (xi) SEQUENCE DESCRIPTION:  SEQ ID NO: 23:

GGGGGAGAAC GCGGAUCCGA GCAAUCCCGG GCGCAUAGCU UCCGAGGAGA        50

CAGGCGGGAG GGUGGAUGU GGCGUCUCGA GAAGCUUCGC UCUAGAUCUC         100

CCUUUAGUGA GGGUUA                                             116

(2) INFORMATION FOR SEQ ID NO: 24:

(i) SEQUENCE CHARACTERISTICS:
        (A) LENGTH:  116 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:    All U's (ix) FEATURE:
        (D) OTHER INFORMATION:    All C's (xi) SEQUENCE DESCRIPTION:  SEQ ID NO: 24:

GGGGGAGAAC GCGGAUCCGA GCAAUCCCAG GCGCAUAGCU UCCGAGUAGA        50

CAGGCGGGAG GGUGGAUGU GGCGUCUCGA GAAGCUUCGC UCUAGAUCUC         100

CCUUUAGUGA GGGUUA                                             116

(2) INFORMATION FOR SEQ ID NO: 25:
```

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: RNA (ix) FEATURE:
    (D) OTHER INFORMATION: All pyri
        modified (xi) SEQUENCE DESCRIPTION: SEQ ID NO: 25:

GCUUCCGAGU AGACAGGAGG GAGGGGUGGA UGUGGCGUCU AC                42

(2) INFORMATION FOR SEQ ID NO: 26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 26:

CUUCCGAGUA GACAGGAGGG AGGGGUGGAU GUGGCGUCUA CUC               43

(2) INFORMATION FOR SEQ ID NO: 27:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyri
            modified (xi) SEQUENCE DESCRIPTION: SEQ ID NO: 27:

GGGGGAGAAC GCGGAUCCGG CAACCCCAGG CGCAUAGCUU CCGAGUAGAC        50

AGGCGGGAGG GGUGGAUGUG GCGUCACG                               78

(2) INFORMATION FOR SEQ ID NO: 28:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyri
            modified (xi) SEQUENCE DESCRIPTION: SEQ ID NO: 28:

GGGGGAGAAC GCGGAUCCUG AGAAGGACGU CGGGGUCAAC GGGGUGAGGU        50

GCAGCAGAAA GGGCCGGCAC CACAUGACGU AAAAGCUUCG CUCUAGAUCU       100

CCCUUUAGUG AGGGUUA                                           117

(2) INFORMATION FOR SEQ ID NO: 29:

```
    (i) SEQUENCE CHARACTERISTICS:
        (A) LENGTH:  108 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:     All pyri
            modified (xi) SEQUENCE DESCRIPTION: SEQ ID NO: 29:

GGGGGAGAAC GCGGAUCCUG AGAAGGACGU CGGGGUGAGG UGCAGCAGAA            50

AGGGCCGGCA CCACAUGACG UAAAAGCUUC GCUCUAGAUC UCCCUUUAGU           100

GAGGGUUA                                                         108

(2) INFORMATION FOR SEQ ID NO: 30:

(i) SEQUENCE CHARACTERISTICS:
        (A) LENGTH:  92 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:     All pyri
            modified (xi) SEQUENCE DESCRIPTION: SEQ ID NO: 30:

GGGGGAGAAC GCGGAUCCGG UGGGAAAGUC GGAUUAUGUG UGUAGAUUUG            50

UGUGCGAAAG CUUCGCUCUA GAUCUCCCUU UAGUGAGGGU UA                   92

(2) INFORMATION FOR SEQ ID NO: 31:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:     All pyri
            modified (xi) SEQUENCE DESCRIPTION: SEQ ID NO: 31:

GGAGAACGCG GAUCCUGAGA AGGACGUCGG GGUCAACGGG GUGAGGUGCA            50

GCAGAAAGGG CCGGCACCA                                             69

(2) INFORMATION FOR SEQ ID NO: 32:

(i) SEQUENCE CHARACTERISTICS:
        (A) LENGTH:  117 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:     All pyri
            modified (xi) SEQUENCE DESCRIPTION: SEQ ID NO: 32:
```

```
GGGGGAGAAC GCGGAUCCUG CUAGACCGAG GAUGCAAAGG GACAUGCAUU           50

AGGGAAACCU AUGUAUAAGA ACGCGGUCGC AGAAGCUUCG CUCUAGAUCU          100

CCCUUUAGUG AGGGUUA                                              117

(2) INFORMATION FOR SEQ ID NO: 33:

(i) SEQUENCE CHARACTERISTICS:
            (A) LENGTH: 83 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:    All pyri
                modified (xi) SEQUENCE DESCRIPTION: SEQ ID NO: 33:

GGGGGAGAAC GCGGAUCCUG CUAGACCGAG GAUGCAAAGG GACAUGCAUU           50

AGGGAAACCU AUGUAUAAGA ACGCGGUCGC AGA                            83

(2) INFORMATION FOR SEQ ID NO: 34:

(i) SEQUENCE CHARACTERISTICS:
            (A) LENGTH: 116 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:    All pyri
                modified (xi) SEQUENCE DESCRIPTION: SEQ ID NO: 34:

GGGGGAGAAC GCGGAUCCUG CUAGACCGAG GAUGCAAAGG GACAUGCAUU           50

AGGGAAACCU AUUAUAAGAA CGCGGUCGCA GAAGCUUCGC UCUAGAUCUC          100

CCUUUAGUGA GGGUUA                                              116

(2) INFORMATION FOR SEQ ID NO: 35:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:    All C's (ix) FEATURE:
            (D) OTHER INFORMATION:    All U's (xi) SEQUENCE DESCRIPTION: SEQ ID NO: 35:

GGGGGAGAAC GCGGAUCCUG UCUCCACCGC CGAUACUGGG GUUCCUGGGG           50

CCCCUCCAUG CAGGAGGGGG GUGGUUCGGA GAAAGCUUCG CUCUAGAUCU          100

CCCUUUAGUG AGGGUUA                                              117

(2) INFORMATION FOR SEQ ID NO: 36:

(i) SEQUENCE CHARACTERISTICS:
```

(A) LENGTH: 81 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:    All C's (ix) FEATURE:
        (D) OTHER INFORMATION:    All U's (xi) SEQUENCE DESCRIPTION: SEQ ID NO: 36:

GGGGGAGAAC GCGGAUCCUG UCUCCACCGC CGAUACUGGG GUUCCUGGGG           50

CCCCUCCAUG CAGGAGGGGG GUGGUUCGGA G                              81

(2) INFORMATION FOR SEQ ID NO: 37:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:    All C's (ix) FEATURE:
        (D) OTHER INFORMATION:    All U's (xi) SEQUENCE DESCRIPTION: SEQ ID NO: 37:

GGGGGAGAAC GCGGAUCCUG UCUCCACCGC CGAUACUGGG GUUCCUGGGG           50

CCGCUCCAUG CAGGAGGGGG GUGGUUCGGA GAAAGCUUCG CUCUAGAUCU          100

CCCUUUAGUG AGGGUUA                                             117

(2) INFORMATION FOR SEQ ID NO: 38:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:    All C's (ix) FEATURE:
        (D) OTHER INFORMATION:    All U's (xi) SEQUENCE DESCRIPTION: SEQ ID NO: 38:

GGGGGAGAAC GCGGAUCCUG UCUCCACCGC CGAUACUGGG GUUCCUGGGG           50

CCCCUCCAUG CAGGAGGGGU GGUUCGGAGA AAGCUUCGCU CUAGAUCUCC         100

CUUUAGUGAG GGUUA                                               115

(2) INFORMATION FOR SEQ ID NO: 39:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION:    All pyri
        modified (xi) SEQUENCE DESCRIPTION: SEQ ID NO: 39:

GGGGGAGAAC GCGGAUCCGG AAGUCUGGUC UUUGGGGAGU CCGCAUGGCC           50

CUGGCGAAAG CUUCGCUCUA GAUCUCCCUU UAGUGAGGGU UA                  92

(2) INFORMATION FOR SEQ ID NO: 40:

(i) SEQUENCE CHARACTERISTICS:
        (A) LENGTH:   111 base pairs
        (B) TYPE:   nucleic acid
        (C) STRANDEDNESS:   single
        (D) TOPOLOGY:   linear (ii) MOLECULE TYPE:   RNA (ix) FEATURE:
        (D) OTHER INFORMATION:    All pyri
            modified (xi) SEQUENCE DESCRIPTION: SEQ ID NO: 40:

GGGGGAGAAC GCGGAUCCAA GAAUGUUCGG CCGCACGAGG UGACAGUGGU           50

GCGGAUACGG ACCGAUUGGG UUUGCCAAGC UUCGCUCUAG AUCUCCCUUU          100

AGUGAGGGUU A                                                   111

(2) INFORMATION FOR SEQ ID NO: 41:

(i) SEQUENCE CHARACTERISTICS:
        (A) LENGTH:   117 base pairs
        (B) TYPE:   nucleic acid
        (C) STRANDEDNESS:   single
        (D) TOPOLOGY:   linear (ii) MOLECULE TYPE:   RNA (xi) SEQUENCE DESCRIPTION: SEQ ID NO: 41:

GGGGGAGAAC GCGGAUCCGG UCACCCGGGC AUAUAACAAU GCCGACACUG           50

GGUACCUGG GACGGGUGGG ACUGGACGGA AGAAGCUUCG CUCUAGAUCU          100

CCCUUUAGUG AGGGUUA                                             117

(2) INFORMATION FOR SEQ ID NO: 42:

(i) SEQUENCE CHARACTERISTICS:
        (A) LENGTH:   119 base pairs
        (B) TYPE:   nucleic acid
        (C) STRANDEDNESS:   single
        (D) TOPOLOGY:   linear (ii) MOLECULE TYPE:   RNA (xi) SEQUENCE DESCRIPTION: SEQ ID NO: 42:

GGGGGAGAAC GCGGAUCCAU AACCGGCUGC AUGGGAGGGA CAUCCUGGGA           50

AAGGACGGGU CGAGAUGACC UGAGCAGUUC CGGCAAGCUU CGCUCUAGAU         100

CUCCCUUUAG UGAGGGUUA                                           119

(2) INFORMATION FOR SEQ ID NO: 43:

(i) SEQUENCE CHARACTERISTICS:
        (A) LENGTH:   71 base pairs
        (B) TYPE:   nucleic acid
        (C) STRANDEDNESS:   single (D) TOPOLOGY:  linear (ii) MOLECULE TYPE:  DNA (xi) SEQUENCE DESCRIPTION:  SEQ ID NO: 43:

TCGGGCGAGT CGTCTGNNNN NNNNNNNNNN NNNNNNNNNN NNNNNNNNNN            50

NNNNNNCCGC ATCGTCCTCC C                                           71

(2) INFORMATION FOR SEQ ID NO: 44:

(i) SEQUENCE CHARACTERISTICS:
        (A) LENGTH:  32 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 44:

TAATACGACT CACTATAGGG AGGACGATGC GG                               32

(2) INFORMATION FOR SEQ ID NO: 45:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 45:

TCGGGCGAGT CGTCTG                                                 16

(2) INFORMATION FOR SEQ ID NO: 46:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 46:

GGGAGGACGA TGCGGNNNNN NNNNNNNNNN NNNNNNNNNN NNNNNNNNNN            50

NNNNNCAGAC GACTCGCCCG A                                           71

(2) INFORMATION FOR SEQ ID NO: 47:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 47:

GGGAGGACGA TGCGG                                                  15

(2) INFORMATION FOR SEQ ID NO: 48:

(i) SEQUENCE CHARACTERISTICS:
        (A) LENGTH:  19 base pairs
        (B) TYPE:  nucleic acid
        (C) STRANDEDNESS:  single (D) TOPOLOGY: linear (ii) MOLECULE TYPE: DNA (ix) FEATURE:
                (D) OTHER INFORMATION: N at positions 1-3 is biotin (xi) SEQUENCE DESCRIPTION: SEQ ID NO: 48:

NNNTCGGGCG AGTCGTCTG                                              19

(2) INFORMATION FOR SEQ ID NO: 49:

(i) SEQUENCE CHARACTERISTICS:
                (A) LENGTH: 87 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 49:

GCCTGTTGTG AGCCTCCTGT CGAANNNNNN NNNNNNNNNN NNNNNNNNNN            50

NNNNNNNNNN NNNNTTGAGC GTTTATTCTT GTCTCCC                          87

(2) INFORMATION FOR SEQ ID NO: 50:

(i) SEQUENCE CHARACTERISTICS:
                (A) LENGTH: 40 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 50:

TAATACGACT CACTATAGGG AGACAAGAAT AAACGCTCAA                       40

(2) INFORMATION FOR SEQ ID NO: 51:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 51:

GCCTGTTGTG AGCCTCCTGT CGAA                                        24

(2) INFORMATION FOR SEQ ID NO: 52:

(i) SEQUENCE CHARACTERISTICS:
                (A) LENGTH: 87 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 52:

GGGAGACAAG AATAAACGCT CAANNNNNNN NNNNNNNNNN NNNNNNNNNN            50

NNNNNNNNNN NNNTTCGACA GGAGGCTCAC AACAGGC                          87

(2) INFORMATION FOR SEQ ID NO: 53:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 53:

GGGAGACAAG AATAAACGCT CAA                                              23

(2) INFORMATION FOR SEQ ID NO: 54:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N at positions 1-3 is biotin (xi) SEQUENCE DESCRIPTION: SEQ ID NO: 54:

NNNGCCTGTT GTGAGCCTCC TGTCGAA                                          27

(2) INFORMATION FOR SEQ ID NO: 55:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 55:

GGGAGGACGA TGCGGCCAGG GGGGGTATGG GGGTGGTGCT ACTTACTTGC                 50

GTCTTCAGAC GACTCGCCCG A                                                71

(2) INFORMATION FOR SEQ ID NO: 56:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 56:

GGGAGGACGA TGCGGCCAGG GGGGGTATGG GGGTAGTGCT ACTTACTTGC                 50

GTCTTCAGAC GACTCGCCCG A                                                71

(2) INFORMATION FOR SEQ ID NO: 57:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 57:

GGGAGGACGA TGCGGCCAGG GGGGGTATGG GGGTAGTACT ACTTACTTAC                 50

GTCTTCAGAC GACTCGCCCG A                                                71

(2) INFORMATION FOR SEQ ID NO: 58:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 58:

```
GGGAGGACGA TGCGGCCAGG GGGGGTATGG GGGTATACTA CTTACTTACG          50

TCTTCAGACG ACTCGCCCGA                                           70
```

(2) INFORMATION FOR SEQ ID NO: 59:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 59:

```
GGGAGGACGA TGCGGCCAGG GGGGGTATGG GGGTAATACT ACTTACTTAC          50

ATCTTCAGAC GACTCGCCCG A                                         71
```

(2) INFORMATION FOR SEQ ID NO: 60:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 60:

```
GGGAGGACGA TGCGGCCAGG GGGGGTATGG GGGTAATACT ACTTACTTAC          50

GTCTTCAGAC GACTCGCCCG A                                         71
```

(2) INFORMATION FOR SEQ ID NO: 61:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 61:

```
GGGAGGACGA TGCGGCCAGG GGGGGTATGG GGGTGGTGTT ACTTACTTGC          50

GTCTTCAGAC GACTCGCCCG A                                         71
```

(2) INFORMATION FOR SEQ ID NO: 62:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 62:

GGGAGGACGA TGCGGCCAGG GGGGGTATGG GGGTGGTGCT TCTTACTTGC        50

GTCTTCAGAC GACTCGCCCG A                                       71

(2) INFORMATION FOR SEQ ID NO: 63:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 63:

GGGAGGACGA TGCGGCCAGG GGGGGTATGG GGGTGGTGTA CTTTTTCCTG        50

CGTCTTCCAG ACGACTCGCC CGA                                     73

(2) INFORMATION FOR SEQ ID NO: 64:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 64:

GGGAGGACGA TGCGGCCAGG GGGGGTATGG GGGTGGTTCG TTTTTCTTTG        50

CGGCTTCAGA CGACTCGCCC GA                                      72

(2) INFORMATION FOR SEQ ID NO: 65:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 65:

GGGAGGACGA TGCGGCCAGG GGGGGTGTGG GGGTGGTGTA CTTTTTCTTG        50

TCTTCCAGAC GACTCGCCCG A                                       71

(2) INFORMATION FOR SEQ ID NO: 66:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 66:

GGGAGGACGA TGCGGCCAGG GGGGGTATGG GGGTGGTTTG GTATGTTGCG        50

TCCGTCAGAC GACTCGCCCG A                                       71

(2) INFORMATION FOR SEQ ID NO: 67:

(i) SEQUENCE CHARACTERISTICS:

```
            (A) LENGTH: 71 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 67:

GGGAGGACGA TGCGGCCGGG GTGGGTATGG GGGTAATACT ACTTACTTAC          50

GTCTTCAGAC GACTCGCCCG A                                        71

(2) INFORMATION FOR SEQ ID NO:68 :

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 68:

GGGAGGACGA TGCGGCCGGG GGTGGGTAGG GGGGTAGTGC TACTTACTTA          50

CGTCTTCAGAC GACTCGCCC GA                                       72

(2) INFORMATION FOR SEQ ID NO: 69:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 69:

GGGAGGACGA TGCGGCCAGG GTCGGTGTGG GGGTAGTACT ACTTACTTGC          50

GTCTTCAGAC GACTCGCCCG A                                        71

(2) INFORMATION FOR SEQ ID NO: 70:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 70:

GGGAGGACGA TGCGGCCAGG GTGGGTATGG GGGTAGTGCT ACTTACTTGC          50

GTCTTCAGAC GACTCGCCCG A                                        71

(2) INFORMATION FOR SEQ ID NO: 71:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 71:

GGGAGGACGA TGCGGCCGGG GTGGGTATGG GGGTGGTGCT ACTTACTTGC          50
```

```
GTCTTCAGAC GACTCGCCCG A                                              71

(2) INFORMATION FOR SEQ ID NO: 72:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 72:

GGGAGGACGA TGCGGCCTGG GTGGGTATGG GGGTGGTGCT ACTTACTTGC                50

GTCTTCAGACG ACTCGCCCG A                                              71

(2) INFORMATION FOR SEQ ID NO: 73:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 73:

GGGAGGACGA TGCGGCCACG GGTGGGTGTG GGGTAGTGTG TCTCACTTTA                50

CATCACCAGA CGACTCGCCC GA                                             72

(2) INFORMATION FOR SEQ ID NO: 74:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 74:

GGGAGGACGA TGCGGCCCGG GGTGGGTGTG GGGTAGTGTA TTATATTTAC                50

AGCCTCAGAC GACTCGCCCG A                                              71

(2) INFORMATION FOR SEQ ID NO: 75:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 75:

GGGAGGACGA TGCGGCCAGG GTCGGTGTGG GGTGGTGTAC TTTTTCCTGT                50

CCTTCCAGAC GACTCGCCCG A                                              71

(2) INFORMATION FOR SEQ ID NO: 76:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear
```

(ii) MOLECULE TYPE: DNA (xi) SEQUENCE DESCRIPTION: SEQ ID NO: 76:

GGGAGGACGA TGCGGCCAGG GTCGGTATGG GGTAGTGTAC TTTTTAATGA          50

TCTTCCAGAC GACTCGCCCG A          71

(2) INFORMATION FOR SEQ ID NO: 77:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 77:

GGGAGGACGA TGCGGCCCGG GGGAGAGCGG TGGGTAGTGT TCTATAGTAT          50

TCGTGTCAGA CGACTCGCCC GA          72

(2) INFORMATION FOR SEQ ID NO: 78:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 78:

GGGAGGACGA TGCGGCCAGG GGGGGTATGT TTTTAATACT ACTTACTTAC          50

GTCTTCAGAC GACTCGCCCG A          71

(2) INFORMATION FOR SEQ ID NO: 79:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 79:

GGGAGGACGA TGCGGCCAGG GAGGGTATGG GGTGGTGTT TCTAGTTTTG          50

CGGCGTCAGA CGACTCGCCC GA          72

(2) INFORMATION FOR SEQ ID NO: 80:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 80:

GGGAGGACGA TGCGGCCAGG GTGGGCATGG GGTGGTGTG GATTAATTCT          50

TCGTCCCAGA CGACTCGCCC GA          72

(2) INFORMATION FOR SEQ ID NO: 81:

```
    (i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 81:

GGGAGGACGA TGCGGCCAGG GTCGGTGTGG GGTGGTGTTT TTATTTACTC          50

GTCGCCAGAC GACTCGCCCG A                                        71

(2) INFORMATION FOR SEQ ID NO: 82:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 82:

GGGAGGACGA TGCGGGGGGC GGCTTGGAAG AGGTTGCCGG TTGGAGTATT          50

CGAGCCAGAC GACTCGCCCG A                                        71

(2) INFORMATION FOR SEQ ID NO: 83:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 83:

GGGAGGACGA TGCGGCCAGG TGTGGGGTGG TTTGGGTTTT CTTTCGTCGC          50

CCAGACGACT CGCCCGA                                             67

(2) INFORMATION FOR SEQ ID NO: 84:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 84:

GGGAGGACGA TGCGGCCAGG GTGGGTATGG GGGTTTAATT AATTCTTCGT          50

CCCACAGACG ACTCGCCCGA                                          70

(2) INFORMATION FOR SEQ ID NO: 85:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 85:

GGGAGGACGA TGCGGGGGGC GGCTTGGAAG AGGTTGCCGG TTGGAGTATT          50
```

```
CGAGCCAGAC GACTCGCCCG A                                               71

(2) INFORMATION FOR SEQ ID NO: 86:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 86:

GGGAGGACGA TGCGGCCCGG GGTGGGTGTG GGGTGGTGTG AATTAATTCT                 50

TCGTCCCAGA CGACTCGCCC GA                                              72

(2) INFORMATION FOR SEQ ID NO: 87:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 87:

GGGAGGACGA TGCGGCCCGG GGTGGGTGTG GGGTGGTGTA TTATATTTGC                 50

GGCCTCAGAC GACTCGCCCG A                                               71

(2) INFORMATION FOR SEQ ID NO: 88:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 88:

GGGAGGACGA TGCGGCCAGG GTCGGTGTGG GTGGTGTACT TTTTCCTGTC                 50

CTTCCAGACG ACTCGCCCGA                                                 70

(2) INFORMATION FOR SEQ ID NO: 89:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 89:

GGGAGGACGA TGCGGGGGGC GGCTTGGAAG AGGTTGCCGG TTGGAGTATT                 50

CGAGCCAGAC GACTCGCCCG A                                               71

(2) INFORMATION FOR SEQ ID NO: 90:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear
```

(ii) MOLECULE TYPE: DNA (xi) SEQUENCE DESCRIPTION: SEQ ID NO: 90:

ATCCGCCTGA TTAGCGATAC TNNNNNNNNN NNNNNNNNNN NNNNNNNNNN          50

NNNNNNNNNN NACTTGAGCA AAATCACCTG CAGGGG                          86

(2) INFORMATION FOR SEQ ID NO: 91:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N at positions 1-3 is biotin (xi) SEQUENCE DESCRIPTION: SEQ ID NO: 91:

NNNCCCCTGC AGGTGATTTT GCTCAAGT                                   28

(2) INFORMATION FOR SEQ ID NO: 92:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 92:

CCGAAGCTTA ATACGACTCA CTATAGGGAT CCGCCTGATT AGCGATACT            49

(2) INFORMATION FOR SEQ ID NO: 93:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 93:

ATCCGCCTGA TTAGCGATAC TAGGCTTGAC AAAGGGCACC ATGGCTTAGT           50

GGTCCTAGTA CTTGAGCAAA ATCACCTGCA GGGG                            84

(2) INFORMATION FOR SEQ ID NO: 94:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 94:

ATCCGCCTGA TTAGCGATAC TCAGGGCACT GCAAGCAATT GTGGTCCCAA           50

TGGGCTGAGT ACTTGAGCAA AATCACCTGC AGGGG                           85

(2) INFORMATION FOR SEQ ID NO: 95:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 95:

ATCCGCCTGA TTAGCGATAC TCCAGGCAGT CATGGTCATT GTTTACAGTC            50

GTGGAGTAGG TACTTGAGCA AAATCACCTG CAGGGG                          86

(2) INFORMATION FOR SEQ ID NO: 96:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 96:

ATCCGCCTGA TTAGCGATAC TAGGTGATCC CTGCAAAGGC AGGATAACGT            50

CCTGAGCATC ACTTGAGCAA AATCACCTGC AGGGG                           85

(2) INFORMATION FOR SEQ ID NO: 97:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 97:

ATCCGCCTGA TTAGCGATAC TATGTGATCC CTGCAGAGGG AGGANACGTC            50

TGAGCATCAC TTGAGCAAAA TCACCTGCAG GGG                             83

(2) INFORMATION FOR SEQ ID NO: 98:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 98:

ATCCGCCTGA TTAGCGATAC TCACGTGATC CCATAAGGGC TGCGCAAAAT            50

AGCAGAGCAT CACTTGAGCA AAATCACCTG CAGGGG                          86

(2) INFORMATION FOR SEQ ID NO: 99:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

ATCCGCCTGA TTAGCGATAC TGGTGGACTA GAGGGCAGCA AACGATCCTT            50

GGTTAGCGTC CACTTGAGCA AAATCACCTG CAGGGG     86

(2) INFORMATION FOR SEQ ID NO: 100:

(i) SEQUENCE CHARACTERISTICS:
        (A) LENGTH:  85 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 100:

ATCCGCCTGA TTAGCGATAC TGGTGCGACG AGGCTTACAC AAACGTACAC     50

GTTTCCCCGC ACTTGAGCAA AATCACCTGC AGGGG     85

(2) INFORMATION FOR SEQ ID NO: 101:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 101:

ATCCGCCTGA TTAGCGATAC TTGTCGGAGC AGGGGCGTAC GAAAACTTTA     50

CAGTTCCCCC GACTTGAGCA AAATCACCTG CAGGGG     86

(2) INFORMATION FOR SEQ ID NO: 102:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:102:

ATCCGCCTGA TTAGCGATAC TAGTGGAACA GGGCACGGAG AGTCAAACTT     50

TGGTTTCCCC CACTTGAGCA AAATCACCTG CAGGGG     86

(2) INFORMATION FOR SEQ ID NO: 103:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 103:

ATCCGCCTGA TTAGCGATAC TGTGGGTAGG GATCGGTGGA TGCCTCGTCA     50

CTTCTAGTCC CACTTGAGCA AAATCACCTG CAGGGG     86

(2) INFORMATION FOR SEQ ID NO: 104:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 104:

ATCCGCCTGA TTAGCGATAC TGGGCGCCCT AAACAAAGGG TGGTCACTTC         50

TAGTCCCAGG AACTTGAGCA AAATCACCTG CAGGGG                        86

(2) INFORMATION FOR SEQ ID NO: 105:

(i) SEQUENCE CHARACTERISTICS:
        (A) LENGTH:  87 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 105:

ATCCGCCTGA TTAGCGATAC TTCCGGGCTC GGGATTCGTG GTCACTTTCA         50

GTCCCGGATA TAACTTGAGC AAAATCACCT GCAGGGG                       87

(2) INFORMATION FOR SEQ ID NO: 106:

(i) SEQUENCE CHARACTERISTICS:
        (A) LENGTH:  84 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 106:

ATCCGCCTGA TTAGCGATAC TATGGGAGGG CGCGTTCTTC GTGGTTACTT         50

TTAGTCCCGA CTTGAGCAAA ATCACCTGCA GGGG                          84

(2) INFORMATION FOR SEQ ID NO: 107:

(i) SEQUENCE CHARACTERISTICS:
        (A) LENGTH:  84 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 107:

ATCCGCCTGA TTAGCGATAC TACGGGAGGG CACGTTCTTC GTGGTTACTT         50

TTAGTCCCGA CTTGAGCAAA ATCACCTGCA GGGG                          84

(2) INFORMATION FOR SEQ ID NO: 108:

(i) SEQUENCE CHARACTERISTICS:
        (A) LENGTH:  86 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO: 108:

ATCCGCCTGA TTAGCGATAC TGCTCGTAGG GGGCGATTCT TTCGCCGTTA         50

CTTCCAGTCC TACTTGAGCA AAATCACCTG CAGGGG                        86

(2) INFORMATION FOR SEQ ID NO: 109:

(i) SEQUENCE CHARACTERISTICS:
    (A) LENGTH: 86 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 109:

ATCCGCCTGA TTAGCGATAC TGAGGCATGT TAACATGAGC ATCGTCTCAC           50

GATCCTCAGC CACTTGAGCA AAATCACCTG CAGGGG                         86

(2) INFORMATION FOR SEQ ID NO: 110:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 110:

ATCCGCCTGA TTAGCGATAC TCCACAGGCT ACGGCACGTA GAGCATCACC           50

ATGATCCTGT GACTTGAGCA AAATCACCTG CAGGGG                         86

(2) INFORMATION FOR SEQ ID NO: 111:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 111:

ATCCGCCTGA TTAGCGATAC TGCGGGCATG GCACATGAGC ATCTCTGATC           50

CCGCAATCCT CACTTGAGCA AAATCACCTG CAGGGG                         86

(2) INFORMATION FOR SEQ ID NO: 112:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 112:

ATCCGCCTGA TTAGCGATAC TACCGGGCTA CTTCGTAGAG CATCTCTGAT           50

CCCGGTGCTC GACTTGAGCA AAATCACCTG CAGGGG                         86

(2) INFORMATION FOR SEQ ID NO: 113:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 113:

-continued

```
ATCCGCCTGA TTAGCGATAC TAAAGGGCGA ACGTAGGTCG AGGCATCCAT        50

TGGATCCCTT CACTTGAGCA AAATCACCTG CAGGGG                       86
```

(2) INFORMATION FOR SEQ ID NO: 114:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 114:

```
ATCCGCCTGA TTAGCGATAC TACGGGCTCT GTCACTGTGG CACTAGCAAT        50

AGTCCCGTCG CACTTGAGCA AAATCACCTG CAGGGG                       86
```

(2) INFORMATION FOR SEQ ID NO: 115:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 115:

```
ATCCGCCTGA TTAGCGATAC TGGGCAGACC TTCTGGACGA GCATCACCTA        50

TGTGATCCCG ACTTGAGCAA AATCACCTGC AGGGG                        85
```

(2) INFORMATION FOR SEQ ID NO: 116:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 116:

```
ATCCGCCTGA TTAGCGATAC TAGAGGGGAA GTAGGCTGCC TGACTCGAGA        50

GAGTCCTCCC GACTTGAGCA AAATCACCTG CAGGGG                       86
```

(2) INFORMATION FOR SEQ ID NO: 117:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 117:

```
ATCCGCCTGA TTAGCGATAC TAGGGGTGCG AAACACATAA TCCTCGCGGA        50

TTCCCATCGC TACTTGAGCA AAATCACCTG CAGGGG                       86
```

(2) INFORMATION FOR SEQ ID NO: 118:

(i) SEQUENCE CHARACTERISTICS:
        (A) LENGTH: 83 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 118:

ATCCGCCTGA TTAGCGATAC TGGGGGGGCA ATGGCGGTAC CTCTGGTCCC          50

CTAAATACAC TTGAGCAAAA TCACCTGCAG GGG                            83

(2) INFORMATION FOR SEQ ID NO: 119:

(i) SEQUENCE CHARACTERISTICS:
          (A) LENGTH: 85 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 119:

ATCCGCCTGA TTAGCGATAC TGCGGCTCAA AGTCCTGCTA CCCGCAGCAC          50

ATCTGTGGTC ACTTGAGCAA AATCACCTGC AGGGG                          85

(2) INFORMATION FOR SEQ ID NO: 120:

(i) SEQUENCE CHARACTERISTICS:
          (A) LENGTH: 86 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 120:

ATCCGCCTGA TTAGCGATAC TTTGGGCGTG AATGTCCACG GGTACCTCCG          50

GTCCCAAAGA GACTTGAGCA AAATCACCTG CAGGGG                         86

(2) INFORMATION FOR SEQ ID NO: 121:

(i) SEQUENCE CHARACTERISTICS:
          (A) LENGTH: 85 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 121:

ATCCGCCTGA TTAGCGATAC TTCCGCGCAA GTCCCTGGTA AAGGGCAGCC          50

CTAACTGGTC ACTTGAGCAA AATCACCTGC AGGGG                          85

(2) INFORMATION FOR SEQ ID NO: 122:

(i) SEQUENCE CHARACTERISTICS:
          (A) LENGTH: 86 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 122:

ATCCGCCTGA TTAGCGATAC TCAAGTTCCC CACAAGACTG GGGCTGTTCA          50

AACCGCTAGT AACTTGAGCA AAATCACCTG CAGGGG                         86

(2) INFORMATION FOR SEQ ID NO: 123:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 123:

ATCCGCCTGA TTAGCGATAC TCAAGTAGGG CGCGACACAC GTCCGGGCAC          50

CTAAGGTCCC AACTTGAGCA AAATCACCTG CAGGGG                         86

(2) INFORMATION FOR SEQ ID NO: 124:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 124:

ATCCGCCTGA TTAGCGATAC TAAAGTCGTG CAGGGTCCCC TGGAAGCATC          50

TCCGATCCCA GACTTGAGCA AAATCACCTG CAGGGG                         86

(2) INFORMATION FOR SEQ ID NO: 125:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 125:

GGGAGACAAG AAUAACGCUC AANNNNNNNN NNNNNNNNNN NNNNNNNNNN          50

NNNNNNNNNN NNNNNNNNNN NNUUCGACAG GAGGCUCACA ACAGGC              96

(2) INFORMATION FOR SEQ ID NO: 126:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 126:

TAATACGACT CACTATAGGG AGACAAGAAT AACGCTCAA                      39

(2) INFORMATION FOR SEQ ID NO: 127:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 127:

GCCTGTTGTG AGCCTCCTGT CGAA                                      24

(2) INFORMATION FOR SEQ ID NO: 128:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F mod (xi) SEQUENCE DESCRIPTION: SEQ ID NO: 128:

```
GGGAGACAAG AAUAACGCUC AACGGUGGCA UUUCUUCACU UCCUUCUCGC          50

UUUCUCGCGU UGGGCNCGAU UCGACAGGAG GCUCACAACA GGC                 93
```

(2) INFORMATION FOR SEQ ID NO: 129:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 129:

```
GGGAGACAAG AAUAACGCUC AACCAACCUU CUGUCGGCGU UGCUUUUUGG          50

ACGGCACUCA GGCUCCAUUC GACAGGAGGC UCACAACAGG C                   91
```

(2) INFORMATION FOR SEQ ID NO:130:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F mod (xi) SEQUENCE DESCRIPTION: SEQ ID NO:130::

```
GGGAGACAAG AAUAACGCUC AAUCGAUCGG UUGUGUGCCG GACAGCCUUA          50

ACCAGGGCUG GGACCGAGGC CUUCGACAGG AGGCUCACAA CAGGC               95
```

(2) INFORMATION FOR SEQ ID NO: 131:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F mod (xi) SEQUENCE DESCRIPTION: SEQ ID NO: 131:

```
GGGAGACAAG AAUAACGCUC AACUGAGUAG GGGAGGAAGU UGAAUCAGUU          50
```

GUGGCGCCUC UCAUUCGCUU CGACAGGAGG CUCACAACAG GC                92

(2) INFORMATION FOR SEQ ID NO: 132:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 132:

GGGAGACAAG AAUAACGCUC AACAGCACUU UCGCUUUUCA UCAUUUUUUC        50

UUUCCACUGU UGGGCGCGGA AUUCGACAGG AGGCUCACAA CAGGC             95

(2) INFORMATION FOR SEQ ID NO: 133:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 133:

GGGAGACAAG AAUAACGCUC AAUCAGUGCU GGCGUCAUGU CUCGAUGGGG        50

AUUUUUCUUC AGCACUUUGC CAUUCGACAG GAGGCUCACA ACAGGC            96

(2) INFORMATION FOR SEQ ID NO: 134:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 134:

GGGAGACAAG AAUAACGCUC AAUCUACUUU CCAUUUCUCU UUUCUUCUCA        50

CGAGCGGGUU UCCAGUGAAC CAUUCGACAG GAGGCUCACA ACAGGC            96

(2) INFORMATION FOR SEQ ID NO: 135:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 135:

GGGAGACAAG AAUAACGCUC AACGAUAGUG ACUACGAUGA CGAAGGCCGC        50

GGGUUGGAUG CCCGCAUUGA UUCGACAGGA GGCUCACAAC AGGC            94

(2) INFORMATION FOR SEQ ID NO: 136:

(i) SEQUENCE CHARACTERISTICS:
        (A) LENGTH:  93 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 136:

GGGAGACAAG AAUAACGCUC AAGUCGAUAC UGGCGACUUG CUCCAUUGGC            50

CGAUUAACGA UUCGGUCAGU UCGACAGGAG GCUCACAACA GGC            93

(2) INFORMATION FOR SEQ ID NO: 137:

(i) SEQUENCE CHARACTERISTICS:
        (A) LENGTH:  95 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 137:

GGGAGACAAG AAUAACGCUC AAGUGCAAAC UUAACCCGGG AACCGCGCGU            50

UUCGAUCGAC UUUCCUUUCC AUUCGACAGG AGGCUCACAA CAGGC            95

(2) INFORMATION FOR SEQ ID NO: 138:

(i) SEQUENCE CHARACTERISTICS:
        (A) LENGTH:  96 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 138:

GGGAGACAAG AAUAACGCUC AAAUUCCGCG UUCCGAUUAA UCCUGUGCUC            50

GGAAAUCGGU AGCCAUAGUG CAUUCGACAG GAGGCUCACA ACAGGC            96

(2) INFORMATION FOR SEQ ID NO: 139:

(i) SEQUENCE CHARACTERISTICS:
        (A) LENGTH:  94 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 139:

```
GGGAGACAAG AAUAACGCUC AACGAACGAG GAGGGAGUGG CAAGGGAUGG        50

UUGGAUAGGC UCUACGCUCA UUCGACAGGA GGCUCACAAC AGGC              94

(2) INFORMATION FOR SEQ ID NO: 140:

(i) SEQUENCE CHARACTERISTICS:
        (A) LENGTH:  94 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 140:

GGGAGACAAG AAUAACGCUC AAGCGAAACU GGCGACUUGC UCCAUUGGCC        50

GAUAUAACGA UUCGGUUCAU UUCGACAGGA GGCUCACAAC AGGC              94

(2) INFORMATION FOR SEQ ID NO: 141:

(i) SEQUENCE CHARACTERISTICS:
        (A) LENGTH:  95 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 141:

GGGAGACAAG AAUAACGCUC AACGAACGAG GAGGGAGUCG CAAGGGAUGG        50

UUGGAUAGGC UCUACGCUCA AUUCGACAGG AGGCUCACAA CAGGC             95

(2) INFORMATION FOR SEQ ID NO: 142:

(i) SEQUENCE CHARACTERISTICS:
        (A) LENGTH:  94 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 142:

GGGAGACAAG AAUAACGCUC AACGAGAAGU GACUACGAUG ACGAAGGCCG        50

CGGGUUGAAU CCCUCAUUGA UUCGACAGGA GGCUCACAAC AGGC              94

(2) INFORMATION FOR SEQ ID NO: 143:

(i) SEQUENCE CHARACTERISTICS:
        (A) LENGTH:  95 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 143:
```

GGGAGACAAG AAUAACGCUC AAAAGCAACG AGACCUGACG CCUGAUGUGA         50

CUGUGCUUGC ACCCGAUUCU GUUCGACAGG AGGCUCACAA CAGGC             95

(2) INFORMATION FOR SEQ ID NO: 144:

(i) SEQUENCE CHARACTERISTICS:
        (A) LENGTH:  96 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 144:

GGGAGACAAG AAUAACGCUC AAGUGAUUCU CAUUCUCAAU GCUUUCUCAC         50

AACUUUUUCC ACUUCAGCGU GAUUCGACAG GAGGCUCACA ACAGGC            96

(2) INFORMATION FOR SEQ ID NO: 145:

(i) SEQUENCE CHARACTERISTICS:
        (A) LENGTH:  94 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 145:

GGGAGACAAG AAUAACGCUC AAAAGCAACG AGACUCGACG CCUGAUGUGA         50

CUGUGCUUGC ACCCGAUUCU UUCGACAGGA GGCUCACAAC AGGC              94

(2) INFORMATION FOR SEQ ID NO: 146:

(i) SEQUENCE CHARACTERISTICS:
        (A) LENGTH:  96 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 146:

GGGAGACAAG AAUAACGCUC AAUCGAUCGG UUGUGUGCCG GACAGCUUUG         50

ACCAUGAGCU GGGACCGAGG CCUUCGACAG GAGGCUCACA ACAGGC            96

(2) INFORMATION FOR SEQ ID NO: 147:

(i) SEQUENCE CHARACTERISTICS:
        (A) LENGTH:  96 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION: SEQ ID NO: 147:

GGGAGACAAG AAUAACGCUC AANGACGNGU GGACCUGACU AAUCGACUGA    50

UCAAAGAUCC CGCCCAGAUG GGUUCGACAG GAGGCUCACA ACAGGC    96

(2) INFORMATION FOR SEQ ID NO: 148:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 148:

GGGAGACAAG AAUAACGCUC AACACUGCGA CUUGCAGAAG CCUUGUGUGG    50

CGGUACCCCC UUUGGCCUCG UUCGACAGGA GGCUCACAAC AGGC    94

(2) INFORMATION FOR SEQ ID NO: 149:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 149:

GGGAGACAAG AAUAACGCUC AAGGUGGCAU UUCUUCAUUU UCCUUCUCGC    50

UUUCUCCGCC GUUGGGCGCG UUCGACAGGA GGCUCACAAC AGGC    94

(2) INFORMATION FOR SEQ ID NO: 150:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 150:

GGGAGACAAG AAUAACGCUC AACCUGAGUA GGGGGGAAAG UUGAAUCAGU    50

UGUGGCGCUC UACUCAUUCG CCUUCGACAG GAGGCUCACA ACAGGC    96

(2) INFORMATION FOR SEQ ID NO: 151:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 151:

GGGAGACAAG AAUAACGCUC AAGUCGAAAC UGGCGACUUG CUCCAUUGGC      50

CGAUAUAACG AUUCGGUUCA UUCGACAGGA GGCUCACAAC AGGC            94

(2) INFORMATION FOR SEQ ID NO: 152:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 152:

GGGAGACAAG AAUAACGCUC AAGCGAUACU GGCGACUUGC UCCAUUGGCC      50

GAUAUAACGA UUCGGCUCAG UUCGACAGGA GGCUCACAAC AGGC            94

(2) INFORMATION FOR SEQ ID NO: 153:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 153:

GGGAGACAAG AAUAACGCUC AAACGUGGGG CACAGGACCG AGAGUCCCUC      50

CGGCAAUAGC CGCUACCCCA CCUUCGACAG GAGGCUCACA ACAGGC          96

(2) INFORMATION FOR SEQ ID NO: 154:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 154:

GGGAGACAAG AAUAACGCUC AACACAGCCU NANAGGGGGG AAGUUGAAUC      50

AGUUGUGGCG CUCUACUCAU UCGCUUCGAC AGGAGGCUCA CAACAGGC        98

(2) INFORMATION FOR SEQ ID NO: 155:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:

(D) OTHER INFORMATION: All pyrimidines are 2'-F modified (xi) SEQUENCE DESCRIPTION: SEQ ID NO: 155:

GGGAGACAAG AAUAACGCUC AAANGGGNUA UGGUGACUUG CUCCAUUGGC        50

CGAUAUAACG AUUCGGUCAG UUCGACAGGA GGCUCACAAC AGGC              94

(2) INFORMATION FOR SEQ ID NO: 156:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 156:

GGGAGACAAG AAUAACGCUC AACCUGCGUA GGGNGGGAAG UUGAAUCAGU        50

UGUGGCGCUC UACUCAUUCG CCUUCGACAG GAGGCUCACA ACAGGC            96

(2) INFORMATION FOR SEQ ID NO: 157:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 157:

GGGAGACAAG AAUAACGCUC AACGAACGAG GAGGGAGUGG CAAGGGAUGG        50

UUGGAUAGGC UCUACGCUCA UUCGACAGGA GGCUCACAAC AGGC              94

(2) INFORMATION FOR SEQ ID NO: 158:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 158:

GGGAGACAAG AAUAACGCUC AAGUGCAAAC UUAACCCGGG AACCGCGCGU        50

UUCGAUUCGC UUUCCNUAUU CCAUUCGACA GGAGGCUCAC AACAGGC           97

(2) INFORMATION FOR SEQ ID NO: 159:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 159:

GGGAGACAAG AAUAACGCUC AACGAACGAG GAGGGAGUGG CAAGGGACGG          50

UNNAUAGGCU CUACGCUCAU UCGACAGGAG GCUCACAACA GGC                93

(2) INFORMATION FOR SEQ ID NO: 160:

(i) SEQUENCE CHARACTERISTICS:
              (A) LENGTH: 93 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 160:

GGGAGACAAG AAUAACGCUC AAUCGGUGUG GCUCAGAAAC UGACACGCGU          50

GAGCUUCGCA CACAUCUGCU UCGACAGGAG GCUCACAACA GGC                93

(2) INFORMATION FOR SEQ ID NO: 161:

(i) SEQUENCE CHARACTERISTICS:
              (A) LENGTH: 95 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 161:

GGGAGACAAG AAUAACGCUC AAUAUCGCUU UUCAUCAAUU CCACUUUUUC          50

ACUCUNUAAC UUGGGCGUGC AUUCGACAGG AGGCUCACAA CAGGC              95

(2) INFORMATION FOR SEQ ID NO: 162:

(i) SEQUENCE CHARACTERISTICS:
              (A) LENGTH: 96 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 162:

GGGAGACAAG AAUAACGCUC AAGUGCAAAC UUAACCCGGG AACCGCGCGU          50

UUCGAUCCUG CAUCCUUUUU CCUUCGACAG GAGGCUCACA ACAGGC             96

(2) INFORMATION FOR SEQ ID NO: 163:

(i) SEQUENCE CHARACTERISTICS:
              (A) LENGTH: 93 base pairs
              (B) TYPE: nucleic acid
              (C) STRANDEDNESS: single
              (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 163:

GGGAGACAAG AAUAACGCUC AAUCGNUCGG UUGUGUGCCG GCAGCUUUGU        50

CCAGCGUUGG GCCGAGGCCU UCGACAGGAG GCUCACAACA GGC              93

(2) INFORMATION FOR SEQ ID NO: 164:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 164:

GGGAGACAAG AAUAACGCUC AAAGUACCCA UCUCAUCUUU UCCUUUCCUU        50

UCUUCAAGGC ACAUUGAGGG UUUCGACAGG AGGCUCACAA CAGGC             95

(2) INFORMATION FOR SEQ ID NO: 165:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 165:

GGGAGACAAG AAUAACGCUC AACCUGAGUA GGGGGGGAAG UUGAACCAGU        50

UGUGGCNGCC UACUCAUUCN CCAUUCGACA GGAGGCUCAC AACAGGC           97

(2) INFORMATION FOR SEQ ID NO: 166:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 166:

GGGAGACAAG AAUAACGCUC AACCNNCCUN CUGUCGGCGC UUGUCUUUUU        50

GGACGGGCAA CCCAGGGCUC UUCGACAGGA GGCUCACAAC AGGC              94

(2) INFORMATION FOR SEQ ID NO: 167:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 167:

GGGAGACAAG AAUAACGCUC AACCAACCUN CUGUCGGCGC UUGUCUUUUU        50

GGACGAGCAA CUCAAGGCUC GUUUCGACAG GAGGCUCACA ACAGGC            96

(2) INFORMATION FOR SEQ ID NO: 168:

(i) SEQUENCE CHARACTERISTICS:
              (A) LENGTH: 93 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 168:

GGGAGACAAG AAUAACGCUC AACCAGCGCA GAUCCCGGGC UGAAGUGACU        50

GCCGGCAACG GCCGCUCCAU UCGACAGGAG GCUCACAACA GGC               93

(2) INFORMATION FOR SEQ ID NO: 169:

(i) SEQUENCE CHARACTERISTICS:
              (A) LENGTH: 96 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 169:

GGGAGACAAG AAUAACGCUC AAUUCCCGUA ACAACUUUUC AUUUUCACUU        50

UUCAUCCAAC CAGUGAGCAG CAUUCGACAG GAGGCUCACA ACAGGC            96

(2) INFORMATION FOR SEQ ID NO: 170:

(i) SEQUENCE CHARACTERISTICS:
              (A) LENGTH: 96 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-F modified (xi) SEQUENCE DESCRIPTION: SEQ ID NO: 170:

GGGAGACAAG AAUAACGCUC AAUAUCGCUU UCAUCAAAUU CCACUCCUUC        50

ACUUCUUUAA CUUGGGCGUG CAUUCGACAG GAGGCUCACA ACAGGC            96

(2) INFORMATION FOR SEQ ID NO: 171:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE:  DNA (ix) FEATURE:
           (D) OTHER INFORMATION:  N at positions 1 and 23
               base pair to each other and can be 1-4
               base pairs long.

(ix) FEATURE:
           (D) OTHER INFORMATION:  N at positions 5 and 10
               is any base pair.

(ix) FEATURE:
           (D) OTHER INFORMATION:  N at positions 6 and 9
               is any base pair.

(ix) FEATURE:
           (D) OTHER INFORMATION:  N at positions 7 and 8 is
               any base pair.

(xi) SEQUENCE DESCRIPTION:  SEQ ID NO: 171:

NGGCNNNNNN GRKYAYYRRT CCN                                          23

(2) INFORMATION FOR SEQ ID NO: 172:

(i) SEQUENCE CHARACTERISTICS:
          (A) LENGTH:  38 base pairs
          (B) TYPE:  nucleic acid
          (C) STRANDEDNESS:  single
          (D) TOPOLOGY:  linear (ii) MOLECULE TYPE:  DNA (ix) FEATURE:
           (D) OTHER INFORMATION:  Nucleotide 38 is an
               inverted orientation T (3'-3' linked)

(xi) SEQUENCE DESCRIPTION:  SEQ ID NO: 172:

TGGGAGGGCG CGTTCTTCGT GGTTACTTTT AGTCCCGT                           38

(2) INFORMATION FOR SEQ ID NO: 173:

(i) SEQUENCE CHARACTERISTICS:
          (A) LENGTH:  40 base pairs
          (B) TYPE:  nucleic acid
          (C) STRANDEDNESS:  single
          (D) TOPOLOGY:  linear (ii) MOLECULE TYPE:  DNA (ix) FEATURE:
           (D) OTHER INFORMATION:  Nucleotide 40 is an
               inverted orientation T (3'-3' linked)

(xi) SEQUENCE DESCRIPTION:  SEQ ID NO: 173:

CACAGGCTAC GGCACGTAGA GCATCACCAT GATCCTGTGT                         40

(2) INFORMATION FOR SEQ ID NO: 174:

(i) SEQUENCE CHARACTERISTICS:
          (A) LENGTH:  45 base pairs
          (B) TYPE:  nucleic acid
          (C) STRANDEDNESS:  single
          (D) TOPOLOGY:  linear (ii) MOLECULE TYPE:  DNA (ix) FEATURE:
           (D) OTHER INFORMATION:  Nucleotide 45 is an
               inverted orientation T (3'-3' linked)

(xi) SEQUENCE DESCRIPTION:  SEQ ID NO: 174:

TACTCAGGGC ACTGCAAGCA ATTGTGGTCC CAATGGGCTG AGTAT       45

(2) INFORMATION FOR SEQ ID NO: 175:

(i) SEQUENCE CHARACTERISTICS:
      (A) LENGTH:  36 base pairs
      (B) TYPE:  nucleic acid
      (C) STRANDEDNESS:  single
      (D) TOPOLOGY:  linear (ii) MOLECULE TYPE:  DNA (ix) FEATURE:
      (D) OTHER INFORMATION:  C at positions 8, 11,
          25 and 26 is 2'O-methyl-2'-deoxycytidine.

(ix) FEATURE:
      (D) OTHER INFORMATION:  G at positions 9, 10,
          17, 19 and 35 is 2'-O-methyl-2'-deoxyguanosine.

(ix) FEATURE:
      (D) OTHER INFORMATION:  A at positions 12, 24
          and 27 is 2'-O-methyl-2'-deoxyadenosine.

(ix) FEATURE:
      (D) OTHER INFORMATION:  U at position 34 is
          2'-O-methyl-2'-deoxyuridine.

(ix) FEATURE:
      (D) OTHER INFORMATION:  U at positions 6 and 22 is
          2'-fluoro-2'-deoxyuridine.

(ix) FEATURE:
      (D) OTHER INFORMATION:  C at positions 23, 32 and
          33 is 2'-fluoro-2'-deoxycytidine.

(ix) FEATURE:
      (D) OTHER INFORMATION:  Nucleotide 36 is an
          inverted orientation T (3'-3' linked).

(xi) SEQUENCE DESCRIPTION:  SEQ ID NO: 175:

CAGGCUACGG CACGTAGAGC AUCACCATGA TCCUGT       36

(2) INFORMATION FOR SEQ ID NO: 176:

(i) SEQUENCE CHARACTERISTICS:
      (A) LENGTH:  32 base pairs
      (B) TYPE:  nucleic acid
      (C) STRANDEDNESS:  single
      (D) TOPOLOGY:  linear (ii) MOLECULE TYPE:  DNA (ix) FEATURE:
      (D) OTHER INFORMATION:  C at position 8 is 2'-
          O-methyl-2'-deoxycytidine.

(ix) FEATURE:
      (D) OTHER INFORMATION:  G at positions 9, 17
          and 31 is 2'-O-methyl-2'-deoxyguanosine.

(ix) FEATURE:
      (D) OTHER INFORMATION:  A at position 22 is
          2'-O-methyl-2'-deoxyadenine.

(ix) FEATURE:
      (D) OTHER INFORMATION:  U at position 30 is 2'-
          O-methyl-2'-deoxyuridine.

(ix) FEATURE:
      (D) OTHER INFORMATION:  U at positions 6 and
          20 is 2'-fluoro-2'-deoxyuridine.

(ix) FEATURE:
      (D) OTHER INFORMATION:  C at positions 21, 28
          and 29 is 2'-fluoro-2'-deoxycytidine.

(ix) FEATURE:
              (D) OTHER INFORMATION:  N at positions 10 and 23
                    is pentaethylene glycol phosphoramidite
                    spacer.

(ix) FEATURE:
              (D) OTHER INFORMATION:  Nucleotide 32 is an
                    inverted orientation T (3'-3' linked)

(xi) SEQUENCE DESCRIPTION:  SEQ ID NO: 176:

CAGGCUACGN CGTAGAGCAU CANTGATCCU GT                                           32

(2) INFORMATION FOR SEQ ID NO: 177:

(i) SEQUENCE CHARACTERISTICS:
              (A) LENGTH:  39 base pairs
              (B) TYPE:  nucleic acid
              (C) STRANDEDNESS:  single
              (D) TOPOLOGY:  linear (ii) MOLECULE TYPE:  DNA (ix) FEATURE:
              (D) OTHER INFORMATION:  Nucleotide 39 is an
                    inverted orientation T (3'-3' linked)

(xi) SEQUENCE DESCRIPTION:  SEQ ID NO: 177:

CAGTCCGTGG TAGGGCAGGT TGGGGTGACT TCGTGGAAT                                    39

(2) INFORMATION FOR SEQ ID NO: 178:

(i) SEQUENCE CHARACTERISTICS:
              (A) LENGTH:  37 base pairs
              (B) TYPE:  nucleic acid
              (C) STRANDEDNESS:  single
              (D) TOPOLOGY:  linear (ii) MOLECULE TYPE:  DNA (ix) FEATURE:
              (D) OTHER INFORMATION:  T at positions 13, 14,
                    16 and 17 is substituted with IdU.

(xi) SEQUENCE DESCRIPTION:  SEQ ID NO: 178:

TGGGAGGGCG CGTTCTTCGT GGTTACTTTT AGTCCCG                                      37

(2) INFORMATION FOR SEQ ID NO: 179:

(i) SEQUENCE CHARACTERISTICS:
              (A) LENGTH:  37 base pairs
              (B) TYPE:  nucleic acid
              (C) STRANDEDNESS:  single
              (D) TOPOLOGY:  linear (ii) MOLECULE TYPE:  DNA (ix) FEATURE:
              (D) OTHER INFORMATION:  T at position 20 is substituted with
                    IdU.

(xi) SEQUENCE DESCRIPTION:  SEQ ID NO: 179:

TGGGAGGGCG CGTTCTTCGT GGTTACTTTT AGTCCCG                                      37

(2) INFORMATION FOR SEQ ID NO: 180:

(i) SEQUENCE CHARACTERISTICS:
              (A) LENGTH:  37 base pairs
              (B) TYPE:  nucleic acid
              (C) STRANDEDNESS:  single
              (D) TOPOLOGY:  linear (ii) MOLECULE TYPE: DNA (ix) FEATURE:
    (D) OTHER INFORMATION: T at position 23 is substitu (xi) SEQUENCE DESCRIPTION: SEQ ID NO: 180:

TGGGAGGGCG CGTTCTTCGT GGTTACTTTT AGTCCCG                37

(2) INFORMATION FOR SEQ ID NO: 181:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: T at position 24 is substitu (xi) SEQUENCE DESCRIPTION: SEQ ID NO: 181:

TGGGAGGGCG CGTTCTTCGT GGTTACTTTT AGTCCCG                37

(2) INFORMATION FOR SEQ ID NO: 182:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: T at position 27 is substitu (xi) SEQUENCE DESCRIPTION: SEQ ID NO: 182:

TGGGAGGGCG CGTTCTTCGT GGTTACTTTT AGTCCCG                37

(2) INFORMATION FOR SEQ ID NO: 183:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: T at positions 28-30 is subs (xi) SEQUENCE DESCRIPTION: SEQ ID NO: 183:

TGGGAGGGCG CGTTCTTCGT GGTTACTTTT AGTCCCG                37

(2) INFORMATION FOR SEQ ID NO: 184:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: T at position 33 is substitu (xi) SEQUENCE DESCRIPTION: SEQ ID NO: 184:

TGGGAGGGCG CGTTCTTCGT GGTTACTTTT AGTCCCG                    37

(2) INFORMATION FOR SEQ ID NO: 185:

(i) SEQUENCE CHARACTERISTICS:
        (A) LENGTH:  7 amino acids
        (B) TYPE:  amino acid
        (C) STRANDEDNESS:
        (D) TOPOLOGY:  linear (ii) MOLECULE TYPE:  Peptide (ix) FEATURE:
        (D) OTHER INFORMATION: Xaa at position 5 is a modif
            that could not be identified.

(xi) SEQUENCE DESCRIPTION:  SEQ ID NO: 185:

Lys Lys Pro Ile Xaa Lys Lys
                 5

(2) INFORMATION FOR SEQ ID NO: 186:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (xi) SEQUENCE DESCRIPTION:  SEQ ID NO: 186:

GGGAGGACGA UGCGGNNNNN NNNNNNNNNN NNNNNNNNNN NNNNNNNNNN      50

NNNNNCAGAC GACUCGCCCG A                                     71

(2) INFORMATION FOR SEQ ID NO: 187:

(i) SEQUENCE CHARACTERISTICS:
        (A) LENGTH:  32 base pairs
        (B) TYPE:  nucleic acid
        (C) STRANDEDNESS:  single
        (D) TOPOLOGY:  linear (ii) MOLECULE TYPE:  RNA (xi) SEQUENCE DESCRIPTION:  SEQ ID NO: 187:

TAATACGACT CACTATAGGG AGGACGATGC GG                         32

(2) INFORMATION FOR SEQ ID NO: 188:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  RNA (xi) SEQUENCE DESCRIPTION:  SEQ ID NO: 188:

TCGGGCGAGT CGTCTG                                           16

(2) INFORMATION FOR SEQ ID NO: 189:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 189:

GGGAGGACGA UGCGGGAAGG GACGAUAAAG AGGAAUCGAA CAACAAGUGG            50

CUGGCCAGAC GACUCGCCCG A                                          71

(2) INFORMATION FOR SEQ ID NO: 190:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 190:

GGGAGGACGA UGCGGGCGGG AAGGUCCGAA GACCGGCGAA AGGAACGAGA            50

UUGCCCAGAC GACUCGCCCG A                                          71

(2) INFORMATION FOR SEQ ID NO:191:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO:191:

GGGAGGACGA UGCGGGUGGU GAAGAGGUAC CGGAAUUGCU AAAGAUACCA            50

GGCCCAGACG ACUCGCCCGA                                            70

(2) INFORMATION FOR SEQ ID NO: 192:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO:192:

GGGAGGACGA UGCGGGCAGG GAGCAAUGAA CUCAAGUCAA GCCGGUGCAC            50

GUGGGCAGAC GACUCGCCCG A                                          71

(2) INFORMATION FOR SEQ ID NO:193:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All pyrimidines are 2'-NH2 modified (xi) SEQUENCE DESCRIPTION: SEQ ID NO:193:

GGGAGGACGA UGCGGUAGCU GCUGUCAUGC AAGACACUAG AAGAUUAAGA          50

UGGGGCAGAC GACUCGCCCG A          71

(2) INFORMATION FOR SEQ ID NO:194:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO:194:

GGGAGGACGA UGCGGGGGCC GGAUUUGAAC CGACGACUUC GGGUUAUGAG          50

CCCGACGUCA GACGACUCGC CCGA          74

(2) INFORMATION FOR SEQ ID NO: 195:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 195:

GGGAGGACGA UGCGGUCCAG GGAUUGAAGU GUCGGGUAG GAACAUAAAG          50

GCGGCCAGAC GACUCGCCCG A          71

(2) INFORMATION FOR SEQ ID NO: 196:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 196:

GGGAGGACGA UGCGGAAGUU CUAACAAGUU AGUGGAAGGU UCCACUUGAA          50

UGUACAGACG ACUCGCCCGA          70

(2) INFORMATION FOR SEQ ID NO: 197:

(i) SEQUENCE CHARACTERISTICS:
        (A) LENGTH: 44 base pairs
        (B) TYPE: nucleic acid
        (C) STRANDEDNESS: single

```
            (D) TOPOLOGY:  linear (ii) MOLECULE TYPE:  RNA (ix) FEATURE:
            (D) OTHER INFORMATION:  All pyrimidines are 2'-NH2 modified (xi) SEQUENCE DESCRIPTION:  SEQ ID NO: 197:

GGGAGGACGA UGCGGAUGGA GCUGAAAUCA GACGACUCGC CCGA                    44

(2) INFORMATION FOR SEQ ID NO: 198:

(i) SEQUENCE CHARACTERISTICS:
            (A) LENGTH:  71 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-NH2 modified (xi) SEQUENCE DESCRIPTION:  SEQ ID NO: 198:

GGGAGGACGA UGCGGGUGGG AAGAUGAGCC GGUCGGCAGU AAUGUGACAC              50

UGCGGCAGAC GACUCGCCCG A                                             71

(2) INFORMATION FOR SEQ ID NO: 199:

(i) SEQUENCE CHARACTERISTICS:
            (A) LENGTH:  70 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-NH2 modified (xi) SEQUENCE DESCRIPTION:  SEQ ID NO: 199:

GGGAGGACGA UGCGGGAGGG AAUGAGGAAA CAACUAGCAG AUAACCGAGC              50

UGGCCAGACG ACUCGCCCGA                                               70

(2) INFORMATION FOR SEQ ID NO: 200:

(i) SEQUENCE CHARACTERISTICS:
            (A) LENGTH:  44 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-NH2 modified (xi) SEQUENCE DESCRIPTION:  SEQ ID NO: 200:

GGGAGGACGA UGCGGAUGGA GCUGAAAUCA GACGACUCGC CCGA                    44

(2) INFORMATION FOR SEQ ID NO: 201:

(i) SEQUENCE CHARACTERISTICS:
            (A) LENGTH:  71 base pairs
            (B) TYPE:  nucleic acid
            (C) STRANDEDNESS:  single
            (D) TOPOLOGY:  linear (ii) MOLECULE TYPE:  RNA
```

(ix) FEATURE:
      (D) OTHER INFORMATION: All pyrimidines are 2'-NH2 modified (xi) SEQUENCE DESCRIPTION: SEQ ID NO: 201:

GGGAGGACGA UGCGGUUGCU CUACAAUGAC GCGGUGACUC CGCAGUUCUU         50

GGACACAGAC GACUCGCCCG A                                        71

(2) INFORMATION FOR SEQ ID NO: 202:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 202:

GGGAGGACGA UGCGGGAGGG GAGAAGAAUG CAGGAAACAG CGAAAUGCGU         50

GUGGCCAGAC GACUCGCCCG A                                        71

(2) INFORMATION FOR SEQ ID NO: 203:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 203:

GGGAGGACGA UGCGGGCGGG AAGAGCUAAU GGAAGUGGAA UCAGUCACAG         50

UGCGGCAGAC GACUCGCCCG A                                        71

(2) INFORMATION FOR SEQ ID NO: 204:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 204:

GGGAGGACGA UGCGGGCUUA GGGAAAUGGU UCUGAGGUGG UCAGACGACU         50

CGCCCGA                                                        57

(2) INFORMATION FOR SEQ ID NO: 205:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All pyrimidines are 2'-NH2 modified (xi) SEQUENCE DESCRIPTION: SEQ ID NO: 205:

GGGAGGACGA UGCGGGAAGG GAACAGGAUA AGACAAGUCG AACAAAGCCG        50

AGGUGCAGAC GACUCGCCCG A                                       71

(2) INFORMATION FOR SEQ ID NO: 206:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 206:

GGGAGGACGA UGCGGAUGGA GCUGAAAUCA GACGACUCGC CCGA              44

(2) INFORMATION FOR SEQ ID NO: 207:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 207:

GGGAGGACGA UGCGGGGAGA CGUAGACGGG AACAUAGAAC GAACAUCAAC        50

GCGGCCAGAC GACUCGCCCG A                                       71

(2) INFORMATION FOR SEQ ID NO: 208:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO:208:

GGGAGGACGA UGCGGGAAGU GGAUAGAACA GUCAGAAAUG UAAGCGUGAG        50

GUGCAGACGA CUCGCCCGA                                          69

(2) INFORMATION FOR SEQ ID NO: 209:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-NH2 modified (xi) SEQUENCE DESCRIPTION: SEQ ID NO: 209:

GGGAGGACGA UGCGGGAAGG GUAGGAAGGU CAAGAGGAAA CAGCGCUUCG         50

GGGUGCAGAC GACUCGCCCG A                                       71

(2) INFORMATION FOR SEQ ID NO: 210:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2 modified (xi) SEQUENCE DESCRIPTION: SEQ ID NO: 210:

GGGAGGACGA UGCGGGGCAA AGGAAGUUGG AAUCGGGACU AAGUAGUGUG         50

UGGCCAGACG ACUCGCCCGA                                         70

(2) INFORMATION FOR SEQ ID NO: 211:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2 modified (xi) SEQUENCE DESCRIPTION: SEQ ID NO: 211:

GGGAGGACGA UGCGGAGAAC CAACAGAGCC CCCUGGUGGU GGGGGAAGGA         50

UUCUCAGACG ACUCGCCCGA                                         70

(2) INFORMATION FOR SEQ ID NO: 212:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-NH2 modified (xi) SEQUENCE DESCRIPTION: SEQ ID NO: 212:

GGGAGGACGA UGCGGACACA CAAGUGAAGG UCAGACGCGA AUUACGUGGG         50

UGGGCAGACG ACUCGCCCGA                                         70

(2) INFORMATION FOR SEQ ID NO: 213:

(i) SEQUENCE CHARACTERISTICS:
        (A) LENGTH:  82 base pairs
        (B) TYPE:  nucleic acid
        (C) STRANDEDNESS:  single
        (D) TOPOLOGY:  linear (ii) MOLECULE TYPE: RNA (ix) FEATURE:
    (D) OTHER INFORMATION: All pyrimidines are 2'-NH2 modified (xi) SEQUENCE DESCRIPTION: SEQ ID NO: 213:

GGGAGGACGA UGCGGUCGUG GGGUGGGUGG GGGCAGCGUU GGAAUAAGUA         50

ACUGGUAACG GCUGGCCAGA CGACUCGCCC GA                           82

(2) INFORMATION FOR SEQ ID NO: 214:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 214:

GGGAGGACGA UGCGGGGUGG GUGGUUACCU GUAAUUAUAU UGAUUCUGGC         50

UUUAGCAGAC GACUCGCCCG A                                       71

(2) INFORMATION FOR SEQ ID NO: 215:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 215:

GGGAGGACGA UGCGGCCCCU UAGCUCAGUG GUUAGAGCAG ACGACUCGCC         50

CGA                                                           53

(2) INFORMATION FOR SEQ ID NO: 216:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 216:

GGGAGGACGA UGCGGUAACG UGGAAUAGGG UUAAACAGCU GGAAUAACG          50

UAGGUGGCCA GACGACUCGC CCGA                                    74

(2) INFORMATION FOR SEQ ID NO: 217:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 217:

GGGAGGACGA UGCGGGUAGG GAGUAGGACA GACAUAACAG UGCAACCAUC            50

GUGGCCAGAC GACUCGCCCG A                                          71

(2) INFORMATION FOR SEQ ID NO: 218:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 218:

GGGAGGACGA UGCGGAAACG GCGUGGCAAA AGUGAGGGGG UAGGAUGUAC            50

CAUGGGUCAG ACGACUCGCC CGA                                        73

(2) INFORMATION FOR SEQ ID NO: 219:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 219:

GGGAGGACGA UGCGGGAGGG GAAAAUGAGA CCGACAGAUU GACGGAAGUA            50

CUGGGCAGAC GACUCGCCCG A                                          71

(2) INFORMATION FOR SEQ ID NO:220:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-fluor (xi) SEQUENCE DESCRIPTION: SEQ ID NO: 220:

GGGAGGACGA UGCGGGCAUU CGUCAAUACC UUGUUUUAUU CCUUUUCUAG            50

CGGCCCAGAC GACUCGCCCG A                                          71

(2) INFORMATION FOR SEQ ID NO: 221:

(i) SEQUENCE CHARACTERISTICS:
            (A) LENGTH: 71 base pairs
            (B) TYPE: nucleic acid
            (C) STRANDEDNESS: single (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 221:

GGGAGGACGA UGCGGAUCGU AAUCGCCACU ACUACUUUCC GAACCCGCAC            50

GUGGCCAGAC GACUCGCCCG A                                          71

(2) INFORMATION FOR SEQ ID NO: 222:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 222:

GGGAGGACGA UGCGGCGUCC CGAGUCACGC UGUCCUGAUA ACCUUCUCUG            50

UGCCCAGACG ACUCGCCCGA                                            70

(2) INFORMATION FOR SEQ ID NO:223:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 223:

GGGAGGACGA UGCGGGAUCC UUUGUGGGCU CUUGUUGACC CCCUCGUUGU            50

CCCCCCCAGA CGACUCGCCC GA                                         72

(2) INFORMATION FOR SEQ ID NO: 224:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 224:

GGGAGGACGA UGCGGCGGGU ACUCUUCGCC AGCUCCUCCA AGCGCGACCU            50

GUGCCCAGAC GACUCGCCCG A                                          71

(2) INFORMATION FOR SEQ ID NO: 225:

(i) SEQUENCE CHARACTERISTICS:
        (A) LENGTH: 72 base pairs
        (B) TYPE: nucleic acid

```
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 225:

GGGAGGACGA UGCGGUUUCG AAUAGGGCCA UUUCUCACUA GCUAUCCUAC          50

CCUGCCCAGA CGACUCGCCC GA                                       72

(2) INFORMATION FOR SEQ ID NO: 226:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 226:

GGGAGGACGA UGCGGAUAAU GGCUAGAACU AGCUCGCAUC UUGGUGUCCG          50

GUGCCCAGAC GACUCGCCCG A                                        71

(2) INFORMATION FOR SEQ ID NO: 227:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 227:

GGGAGGACGA UGCGGGACCA GAUGGCGGAU UUUUCAGCAA UCCUCCCCCG          50

CUGCCCAGAC GACUCGCCCG A                                        71

(2) INFORMATION FOR SEQ ID NO: 228:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 228:

GGGAGGACGA UGCGGUGAUG GCGACCAGUC AAACCGGUGC UUUUACUCCC          50

CCGCCAGACG ACUCGCCCGA                                          70

(2) INFORMATION FOR SEQ ID NO: 229:

(i) SEQUENCE CHARACTERISTICS:
        (A) LENGTH:  72 base pairs
```

(B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-fluor (xi) SEQUENCE DESCRIPTION:  SEQ ID NO: 229:

GGGAGGACGA UGCGGGAAUU AACAGGGCCA GAAUUCUCAU CUNNCUUCCC            50

GUGACCCAGA CGACUCGCCC GA                                         72

(2) INFORMATION FOR SEQ ID NO: 230:

(i) SEQUENCE CHARACTERISTICS:
            (A) LENGTH:  70 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-fluor (xi) SEQUENCE DESCRIPTION:  SEQ ID NO: 230:

GGGAGGACGA UGCGGCACCU UAGACCUGUC CUCCAAGCGU GAGUUGCUGU            50

GGCCCAGACG ACUCGCCCGA                                            70

(2) INFORMATION FOR SEQ ID NO: 231:

(i) SEQUENCE CHARACTERISTICS:
            (A) LENGTH:  70 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-fluor (xi) SEQUENCE DESCRIPTION:  SEQ ID NO: 231:

GGGAGGACGA UGCGGUGGUC UCCCAAUUCU AAACUUUCUC CAUCGUAUCU            50

GGGCCAGACG ACUCGCCCGA                                            70

(2) INFORMATION FOR SEQ ID NO: 232:

(i) SEQUENCE CHARACTERISTICS:
            (A) LENGTH:  71 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-fluor (xi) SEQUENCE DESCRIPTION:  SEQ ID NO:232:

GGGAGGACGA UGCGGUCAUG GUGUCUUUCC ACAGCUCUUC CCAUGAUCGC            50

CCGGCCAGAC GACUCGCCCG A                                          71

(2) INFORMATION FOR SEQ ID NO: 233:

(i) SEQUENCE CHARACTERISTICS:

(A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 233:

GGGAGGACGA UGCGGGAAUU CCCAGCGCUU GACUGAUACA AACNUUCCCG           50

UGCCCCAGAC GACUCGCCCG A                                          71

(2) INFORMATION FOR SEQ ID NO:234:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 234:

GGGAGGACGA UGCGGCAANN NNNNNCUCUC UCCUGGCGUU CCGCAACCCG           50

CCCCCAGACG ACUCGCCCGA                                            70

(2) INFORMATION FOR SEQ ID NO: 235:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 235:

GGGAGGACGA UGCGGAGUAU UCCAGCCUGG AUUCAUAGUC AGUGCUCUCC           50

GUGCCCAGAC GACUCGCCCG A                                          71

(2) INFORMATION FOR SEQ ID NO: 236:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 236:

GGGAGGACGA UGCGGUCCUA GCAGCGAUUC AUCCCCGUUC UCUCAGCGUU           50

GCCCCCAGAC GACUCGCCCG A                                          71

(2) INFORMATION FOR SEQ ID NO: 237:

(i) SEQUENCE CHARACTERISTICS:
       (A) LENGTH: 71 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-fluor (xi) SEQUENCE DESCRIPTION: SEQ ID NO:237:

GGGAGGACGA UGCGGCCUGA AGUACAGGCU CUAAACUCCA AGCGCGACCG          50

UCCGCCAGAC GACUCGCCCG A                                        71

(2) INFORMATION FOR SEQ ID NO: 238:

(i) SEQUENCE CHARACTERISTICS:
       (A) LENGTH: 68 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-fluor (xi) SEQUENCE DESCRIPTION: SEQ ID NO: 238:

GGGAGGACGA UGCGGCCCUA CCACUUUUUC CCUCUACUGU UAUCCUGUCC          50

CCCAGACGAC UCGCCCGA                                            68

(2) INFORMATION FOR SEQ ID NO: 239:

(i) SEQUENCE CHARACTERISTICS:
       (A) LENGTH: 70 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-fluor (xi) SEQUENCE DESCRIPTION: SEQ ID NO: 239:

GGGAGGACGA UGCGGUGGUC UCCCUAGAUC UACAGCACUU CCAUCGCAUU          50

GGGCCAGACG ACUCGCCCGA                                          70

(2) INFORMATION FOR SEQ ID NO: 240:

(i) SEQUENCE CHARACTERISTICS:
       (A) LENGTH: 69 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-fluor (xi) SEQUENCE DESCRIPTION: SEQ ID NO: 240:

GGGAGGACGA UGCGGUCAAG CUUAACAGUC UGGCAAUGGC CAUUAUGGCG          50

CCCCAGACGA CUCGCCCGA                                           69

(2) INFORMATION FOR SEQ ID NO: 241:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 241:

GGGAGGACGA UGCGGCAGUC UGGAUCUCUA UUGGAAUUUA GUCCUCAACU         50

GUGCCCCAGA CGACUCGCCC GA                                      72

(2) INFORMATION FOR SEQ ID NO: 242:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 242:

GGGAGGACGA UGCGGGAUUC UUUCGGCAAG UGAAAAAUAU CCUUGCUUCC         50

CGAGCCAGAC GACUCGCCCG A                                       71

(2) INFORMATION FOR SEQ ID NO: 243:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 243:

GGGAGGACGA UGCGGGGACU UCAACUAAGU CCUCAUUUGC CUCGCUCCUC         50

GUGCCCAGAC GACUCGCCCG A                                       71

(2) INFORMATION FOR SEQ ID NO: 244:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 244:

GGGAGGACGA UGCGGAACGG AGAUGUCCCC UCAAMAUUUA CCGUCUCCGU         50

UUGCGCCCCA GACGACUCGC CCGA                                    74

```
(2) INFORMATION FOR SEQ ID NO: 245:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO:245:

GGGAGGACGA UGCGGCGAAA UUAGCUUCUU AUGACUCACG UUUCCUUGCC          50

GCCCCAGACG ACUCGCCCGA                                          70

(2) INFORMATION FOR SEQ ID NO: 246:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 246:

GGGAGGACGA UGCGGGCCCG AUCUACUGCA UUACCGAAAC GAUUUCCCCA          50

CUGUGCAGAC GACUCGCCCG A                                        71

(2) INFORMATION FOR SEQ ID NO: 247:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 247:

GGGAGGACGA UGCGGNGACU GAUUUUUCCU UGNCAGUGUA AUUUCCUGGC          50

UGCCCCAGAC GACUCGCCCG A                                        71

(2) INFORMATION FOR SEQ ID NO: 248:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 248:

GGGAGGACGA UGCGGGGACU UUGACAGGCA UUGAUUUCGA CCUGUUCCCC          50

GUGGCCAGAC GACUCGCCCG A                                        71
```

(2) INFORMATION FOR SEQ ID NO: 249:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 249:

```
GGGAGGACGA UGCGGCGACA CAAUAGCCUU UGAUCCCAUG AUGGCUCGCC          50

GUGCCCAGAC GACUCGCCCG A                                        71
```

(2) INFORMATION FOR SEQ ID NO: 250:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 250:

```
GGGAGGACGA UGCGGUGUAG UUUCCCUGUA UGCCAUUCUU UCCCAUGCCG          50

CACGCCAGAC GACUCGCCCG A                                        71
```

(2) INFORMATION FOR SEQ ID NO: 251:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 251:

```
GGGAGGACGA UGCGGUCGAG UGUUCUCCUU CGGUAACUAU UNNNNAUUUC          50

GUGCCCAGAC GACUCGCCCG A                                        71
```

(2) INFORMATION FOR SEQ ID NO: 252:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 252:

```
GGGAGGACGA UGCGGGUCGU AUUCAUCUCC UUGUUCUGUU UCGUUGCACC          50

UGGCCCAGAC GACUCGCCCG A                                        71
```

(2) INFORMATION FOR SEQ ID NO: 253:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 253:

```
GGGAGGACGA UGCGGGGACU UUGACAGGCA UUGAUUUCGA CGUGUUCCCC          50

GUGGCCAGAC GACUCGCCCG A                                        71
```

(2) INFORMATION FOR SEQ ID NO: 254:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 254:

```
GGGAGGACGA UGCGGUGAUC AAUCGGCGCU UUACUCUUGC GCUCACCGUG          50

CCCCAGACGA CUCGCCCGA                                           69
```

(2) INFORMATION FOR SEQ ID NO: 255:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 255:

```
GGGAGGACGA UGCGGCAGUC UCCCUAGGUU UCAUCUCUGC AGCAUUCCGG          50

GGUNCCAGAC GACUCGCCCG A                                        71
```

(2) INFORMATION FOR SEQ ID NO: 256:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 256:

```
GGGAGGACGA UGCGGAUCAA AAGCACUCAU UCCCGUGCUC GCUUCAUUGG          50
```

```
UCCCCCAGAC GACUCGCCCG A                                               71

(2) INFORMATION FOR SEQ ID NO: 257:

(i) SEQUENCE CHARACTERISTICS:
        (A) LENGTH:  74 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 257:

GGGAGGACGA UGCGGAAGAU CUCCCAACUG CUGUGGCUAA UAAUUCUCUC                 50

CGCGUCCCCA GACGACUCGC CCGA                                            74

(2) INFORMATION FOR SEQ ID NO: 258:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 258:

GGGAGGACGA UGCGGUCCGU CAUAACGGCC AUAAACUGCG AAUACUCCCU                 50

GGCCCAGACG ACUCGCCCGA                                                 70

(2) INFORMATION FOR SEQ ID NO: 259:

(i) SEQUENCE CHARACTERISTICS:
        (A) LENGTH:  73 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 259:

GGGAGGACGA UGCGGGGACA AWYAGCGGUG UCUUUUCAUU UNKAUCCUCC                 50

GACRUCCCAG ACGACUCGCC CGA                                             73

(2) INFORMATION FOR SEQ ID NO: 260:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 260:

GGGAGGACGA UGCGGUGACU AUCUGGCUCG AUCCAAUCAC CCGAGCCCAC                 50
```

CGCGCCAGAC GACUCGCCCG A                                              71

(2) INFORMATION FOR SEQ ID NO: 261:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 261:

GGGAGGACGA UGCGGGAACU AAUGGCCGUG AUUAACCAAU GCAGGCUUCC                50

UGCGCCAGAC GACUCGCCCG A                                              71

(2) INFORMATION FOR SEQ ID NO: 262:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 262:

GGGAGGACGA UGCGGUGACA UGGAAUUUUC UACGGGCCCG AUCCUGCCAG                50

CCGUGUGCAG ACGACUCGCC CGA                                            73

(2) INFORMATION FOR SEQ ID NO: 263:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 m (xi) SEQUENCE DESCRIPTION: SEQ ID NO: 263:

GGAANYAANR CRR                                                       13

(2) INFORMATION FOR SEQ ID NO: 264:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 m (xi) SEQUENCE DESCRIPTION: SEQ ID NO: 264:

GGAANYTGA                                                             9

(2) INFORMATION FOR SEQ ID NO: 265:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 2 cytosine (ix) FEATURE:
        (D) OTHER INFORMATION: All U's are 2'NH2 2 uracil (xi) SEQUENCE DESCRIPTION: SEQ ID NO: 265:

```
GGGAGACAAG AAUAACGCUC AAGUAGACUA AUGUGUGGAA GACAGCGGGU          50

GGUUCGACAG GAGGCUCACA ACAGGC                                    76
```

(2) INFORMATION FOR SEQ ID NO: 266:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 2 cytosine (ix) FEATURE:
        (D) OTHER INFORMATION: All U's are 2'NH2

(xi) SEQUENCE DESCRIPTION: SEQ ID NO: 266:

```
GGUGUGUGGA AGACAGCGGG UGGUUC                                    26
```

(2) INFORMATION FOR SEQ ID NO: 267:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's and C's are 2'- deox
            and 2'-deoxy-2' aminocytidine residues (ix) FEATURE:
        (D) OTHER INFORMATION: A at positions 14 and 17 is
            methyladenosine (ix) FEATURE:
        (D) OTHER INFORMATION: G at positions 5, 6, 22, 23,
            2'-deoxy-2'-O-methylguanosine (ix) FEATURE:
        (D) OTHER INFORMATION: T at positions 1-4 and 31-35
            deoxythymidine (xi) SEQUENCE DESCRIPTION: SEQ ID NO:267:

```
TTTTGGUGUG UGGAAGACAG CGGGUGGUUC TTTTT                          35
```

(2) INFORMATION FOR SEQ ID NO: 268:

(i) SEQUENCE CHARACTERISTICS:

```
        (A) LENGTH: 27 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 268:

GGGAGGSGSG GUYUCYYRRY UYYYSYS                                            27

(2) INFORMATION FOR SEQ ID NO: 269:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 269:

RGGRRGRAYY RSBRSYYYYY BSYBSY                                             26

(2) INFORMATION FOR SEQ ID NO: 270:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 m (xi) SEQUENCE DESCRIPTION: SEQ ID NO: 270:

GGGAAGGAAY AARCRRGACC C                                                  21

(2) INFORMATION FOR SEQ ID NO: 271:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 m (xi) SEQUENCE DESCRIPTION: SEQ ID NO: 271:

GGAAYGAYGA Y                                                             11

(2) INFORMATION FOR SEQ ID NO: 272:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: RNA
```

(ix) FEATURE:
          (D) OTHER INFORMATION: All pyrimidines are 2'-fluor (xi) SEQUENCE DESCRIPTION: SEQ ID NO: 272:

GGGAGGACGA UGCGGUGGUC UCCCAAUUCU AAACUUUCUC CAUCGUAUC                49

(2) INFORMATION FOR SEQ ID NO: 273:

(i) SEQUENCE CHARACTERISTICS:
         (A) LENGTH: 47 base pairs
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All pyrimidines are 2'-fluor (xi) SEQUENCE DESCRIPTION: SEQ ID NO: 273:

GGGAGGACGA UGCGGUGGUC UCCCAAUUCU AAACUUUCUC CAUCGUA                  47

(2) INFORMATION FOR SEQ ID NO: 274:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All pyrimidines are 2'-fluor (xi) SEQUENCE DESCRIPTION: SEQ ID NO: 274:

GGGAGGACUG CGGUGGUCUC CCAAUUCUAA ACUUUCUCCA UCGUA                    45

(2) INFORMATION FOR SEQ ID NO: 275:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All pyrimidines are 2'-fluor (xi) SEQUENCE DESCRIPTION: SEQ ID NO: 275:

GGGAGGACGA UGCGGUGGUC UCCCCUAAAC UUUCUCCAUC GUAUC                    45

(2) INFORMATION FOR SEQ ID NO: 276:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All pyrimidines are 2'-fluor (xi) SEQUENCE DESCRIPTION: SEQ ID NO: 276:

GGGAGGACGA UGCGGUGGUC UCCCAAUUCU AUUCUCCAUC GUAUC                    45

(2) INFORMATION FOR SEQ ID NO: 277:

(i) SEQUENCE CHARACTERISTICS:
        (A) LENGTH:   45 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 277:

GGGAGGACGA UGCGGUGGUC UCCCAAUUCU AAACUCCAUC GUAUC                45

(2) INFORMATION FOR SEQ ID NO: 278:

(i) SEQUENCE CHARACTERISTICS:
        (A) LENGTH:   42 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 278:

GGGAGGACGA UGCGGUGGUC UCCCAAUUAA CUCCAUCGUA UC                   42

(2) INFORMATION FOR SEQ ID NO: 279:

(i) SEQUENCE CHARACTERISTICS:
        (A) LENGTH:   47 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 279:

GAGGACGAUG CGGUGGUCUC CCAAUUCUAA ACUUUCUCCA UCGUAUC              47

(2) INFORMATION FOR SEQ ID NO: 280:

(i) SEQUENCE CHARACTERISTICS:
        (A) LENGTH:   42 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 280:

GGGAGGACGA UGCGGUGGUC UCCCAAUUUU CUCCAUCGUA UC                   42

(2) INFORMATION FOR SEQ ID NO: 281:

(i) SEQUENCE CHARACTERISTICS:
        (A) LENGTH:   41 base pairs
        (B) TYPE:  nucleic acid
        (C) STRANDEDNESS:  single (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 281:

GGGAGGACGA UGCGGUGGUC UCCCAAUUCU ACCAUCGUAU C                    41

(2) INFORMATION FOR SEQ ID NO: 282:

(i) SEQUENCE CHARACTERISTICS:
        (A) LENGTH:  44 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 282:

GGAGGACGAU GCGGUGGUCU CCCAAUUCUA UUCUCCAUCG UAUC                 44

(2) INFORMATION FOR SEQ ID NO: 283:

(i) SEQUENCE CHARACTERISTICS:
        (A) LENGTH:  43 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 283:

GGAGGACGAU GCGGUGGUCU CCAAUUCUAU UCUCCAUCGU AUC                  43

(2) INFORMATION FOR SEQ ID NO: 284:

(i) SEQUENCE CHARACTERISTICS:
        (A) LENGTH:  43 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION:  SEQ ID NO: 284:

GAGGACGAUG CGGUGGUCUC CCAAUUCUAU UCUCCAUCGU AUC                  43

(2) INFORMATION FOR SEQ ID NO: 285:

(i) SEQUENCE CHARACTERISTICS:
        (A) LENGTH:  41 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 285:

GAGGACGAUG CGGUGGUCUC AAUUCUAUUC UCCAUCGUAU C               41

(2) INFORMATION FOR SEQ ID NO: 286:

(i) SEQUENCE CHARACTERISTICS:
        (A) LENGTH:  44 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 286:

GGGAGGCGAU GCGGUGGUCU CCCAAUUCUA UUCUCCAUCG UAUC            44

(2) INFORMATION FOR SEQ ID NO: 287:

(i) SEQUENCE CHARACTERISTICS:
        (A) LENGTH:  44 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 287:

GGGAGGACGA UGCGGUGGUC UCCCAAUUCU AUCUCCAUCG UAUC            44

(2) INFORMATION FOR SEQ ID NO: 288:

(i) SEQUENCE CHARACTERISTICS:
        (A) LENGTH:  43 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 288:

GGGAGGACGA UGCGGUGGUC UCCCAAUUCU ACUCCAUCGU AUC             43

(2) INFORMATION FOR SEQ ID NO: 289:

(i) SEQUENCE CHARACTERISTICS:
        (A) LENGTH:  42 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluor (xi) SEQUENCE DESCRIPTION: SEQ ID NO: 289:

GGGAGGACGA UGCGGUGGUC UCCCAAUUCU AUCCAUCGUA UC              42

(2) INFORMATION FOR SEQ ID NO: 290:

```
      (i) SEQUENCE CHARACTERISTICS:
          (A) LENGTH:  44 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-fluor (xi) SEQUENCE DESCRIPTION:  SEQ ID NO: 290:

GGGAGGACGA UGCGGUGGUC UCCCAAUUCU UUCUCCAUCG UAUC                     44

(2) INFORMATION FOR SEQ ID NO: 291:

(i) SEQUENCE CHARACTERISTICS:
          (A) LENGTH:  43 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-fluor (xi) SEQUENCE DESCRIPTION:  SEQ ID NO: 291:

GGGAGGACGA UGCGGUGGUC UCCCAAUUCU UCUCCAUCGU AUC                      43

(2) INFORMATION FOR SEQ ID NO: 292:

(i) SEQUENCE CHARACTERISTICS:
          (A) LENGTH:  41 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-fluor (xi) SEQUENCE DESCRIPTION:  SEQ ID NO: 292:

GGGGACGAUG CGGUGGCCCC AAUUCUAUUC UCCAUCGUAU C                        41

(2) INFORMATION FOR SEQ ID NO: 293:

(i) SEQUENCE CHARACTERISTICS:
          (A) LENGTH:  39 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-fluor (xi) SEQUENCE DESCRIPTION:  SEQ ID NO: 293:

GGGACGAUGC GGUGGCCCAA UUCUAUUCUC CAUCGUAUC                           39

(2) INFORMATION FOR SEQ ID NO: 294:

(i) SEQUENCE CHARACTERISTICS:
          (A) LENGTH:  37 base pairs
          (B) TYPE:  nucleic acid
          (C) STRANDEDNESS:  single
          (D) TOPOLOGY:  linear (ii) MOLECULE TYPE:  RNA
```

(ix) FEATURE:
        (D) OTHER INFORMATION: All pyrimidines are 2'-fluor (xi) SEQUENCE DESCRIPTION: SEQ ID NO: 294:

GACGAUGCGG UGGCCCAAUU CUAUUCUCCA UCGUAUC                                37

(2) INFORMATION FOR SEQ ID NO: 295:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 295:

GGACGAUGCG GUGGCCCAAU UCUAUUCUCC AUCGUAUC                               38

(2) INFORMATION FOR SEQ ID NO: 296:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 296:

GAUGCGGUGG CCCAAUUCUA UUCUCCAUCG UAUC                                   34

(2) INFORMATION FOR SEQ ID NO: 297:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 297:

GAUGCGGUGG UCUCCCAAUU CUAUUCUCCA UCGUAUC                                37

(2) INFORMATION FOR SEQ ID NO: 298:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 298:

GGUGGUCUCC CAAUUCUAUU CUCCAUCGUA UC                                     32

(2) INFORMATION FOR SEQ ID NO: 299:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 299:

GGGAGGACGA UG                                                12

(2) INFORMATION FOR SEQ ID NO: 300:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 300:

GGGAGGACGA UGCGGUGGUC UCCCAAUUCU CUCCAUCGUA UC              42

(2) INFORMATION FOR SEQ ID NO: 301:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 301:

GGGAGGACGA UGCGGUGUCU CCCAAUUCUU CUCAUCGUAU C               41

(2) INFORMATION FOR SEQ ID NO: 302:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluor (xi) SEQUENCE DESCRIPTION: SEQ ID NO: 302:

GGGAGGACGA UGCGGGGUCU CCCAAUUCUU CUCCUCGUAU C               41

(2) INFORMATION FOR SEQ ID NO: 303:

(i) SEQUENCE CHARACTERISTICS:
        (A) LENGTH: 39 base pairs
        (B) TYPE: nucleic acid -continued

```
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-fluor (xi) SEQUENCE DESCRIPTION:  SEQ ID NO: 303:

GGGAGGACGA UGCGGGUCUC CCAAUUCUUC UCUCGUAUC                              39

(2) INFORMATION FOR SEQ ID NO: 304:

(i) SEQUENCE CHARACTERISTICS:
          (A) LENGTH:  43 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-fluor (xi) SEQUENCE DESCRIPTION:  SEQ ID NO: 304:

GGGAGUACGA UGCGGUGGUC UCCCAAUUCU UCUCCAUCGU AUC                         43
```